(12) United States Patent
Skog et al.

(10) Patent No.: US 11,396,676 B2
(45) Date of Patent: Jul. 26, 2022

(54) SEQUENCING AND ANALYSIS OF EXOSOME ASSOCIATED NUCLEIC ACIDS

(71) Applicant: Exosome Diagnostics, Inc., Waltham, MA (US)

(72) Inventors: Johan Skog, Lincoln, MA (US); Sudipto Chakrabortty, Waltham, MA (US); Dalin Chan, Brighton, MA (US); Michael Valentino, Waltham, MA (US); Vasisht Tadigotla, Newton, MA (US); Robert Kitchen, Somerville, MA (US); Dominik Grimm, Schondorf am Ammersee (DE); Wei Yu, Belmont, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 527 days.

(21) Appl. No.: 16/342,572

(22) PCT Filed: Oct. 23, 2017

(86) PCT No.: PCT/US2017/057916
§ 371 (c)(1),
(2) Date: Apr. 17, 2019

(87) PCT Pub. No.: WO2018/076018
PCT Pub. Date: Apr. 26, 2018

(65) Prior Publication Data
US 2020/0208213 A1 Jul. 2, 2020

Related U.S. Application Data

(60) Provisional application No. 62/536,545, filed on Jul. 25, 2017, provisional application No. 62/410,974, filed on Oct. 21, 2016.

(51) Int. Cl.
*C12Q 1/68* (2018.01)
*C12Q 1/6874* (2018.01)
(Continued)

(52) U.S. Cl.
CPC ....... *C12Q 1/6874* (2013.01); *C12N 15/1096* (2013.01); *G01N 1/28* (2013.01); *G01N 33/54326* (2013.01)

(58) Field of Classification Search
None
See application file for complete search history.

(56) References Cited

U.S. PATENT DOCUMENTS 5,219,727 A  6/1993 Wang et al.
5,538,871 A  7/1996 Nuovo et al.
(Continued)

FOREIGN PATENT DOCUMENTS

JP  2016-510992 A  4/2016
WO  WO 2003/023065 A1  3/2003
(Continued)

OTHER PUBLICATIONS

Miranda et al. (Kidney International, 2010, 78:191-199) (Year: 2010).*

(Continued)

*Primary Examiner* — Stephanie K Mummert
(74) *Attorney, Agent, or Firm* — Cooley LLP; Ivor R. Elrifi; Matthew Pavao

(57) ABSTRACT

The invention provides a series of steps that prepare nucleic acids (RNA and/or DNA) isolated from extracellular vesicles for sequencing. This enables a wide diversity of RNAs and/or DNAs, to be efficiently detected. These can then be used to identify various attributes such as gene expression, alternative splicing, and the detection of both somatic and germline mutations including single nucleotide
(Continued)

variants (SNV) and structural variations (insertions/deletions, fusions, inversions).

20 Claims, 43 Drawing Sheets

(51) Int. Cl.
  *C12N 15/10* (2006.01)
  *G01N 1/28* (2006.01)
  *G01N 33/543* (2006.01)

(56) References Cited

U.S. PATENT DOCUMENTS

| | | |
|---|---|---|
| 5,556,773 A | 9/1996 | Yourno |
| 5,639,606 A | 6/1997 | Willey |
| 5,639,611 A | 6/1997 | Wallace et al. |
| 6,004,755 A | 12/1999 | Wang |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,994,960 B1 | 2/2006 | Foote et al. |
| 7,074,563 B2 | 7/2006 | Köster |
| 7,186,512 B2 | 3/2007 | Martienssen et al. |
| 7,198,893 B1 | 4/2007 | Köster et al. |
| 7,198,923 B1 | 4/2007 | Abrignani et al. |
| 7,364,848 B2 | 4/2008 | Van Beuningen et al. |
| 7,378,245 B2 | 5/2008 | Liu |

FOREIGN PATENT DOCUMENTS

| | | | |
|---|---|---|---|
| WO | WO 2006/113590 A2 | 10/2006 | |
| WO | WO 2009/100029 A1 | 8/2009 | |
| WO | WO 2014/107571 A1 | 7/2014 | |
| WO | WO 2014/164486 A1 | 10/2014 | |
| WO | WO 2015/122967 A1 | 8/2015 | |
| WO | WO 2016/007755 A1 | 1/2016 | |
| WO | WO-2016081941 A1 * | 5/2016 | ......... G01N 33/6893 |

OTHER PUBLICATIONS

Sukhishvili et al. (Macromolecules, 2006, 39(26):8873-8881) (Year: 2006).*

Trejo-Becerril et al. (PLoS One, 2012, 7(12):e52754, p. 1-12) (Year: 2012).*

Skog et al. (Nature Cell Biology, 2008, 10(12):1470-1476) (Year: 2008).*

Noerholm et al. (BMC Cancer, 2012, 12:22, p. 1-11) (Year: 2012).*

Abravaya, et al. 1995. Detection of point mutations with a modified ligase chain reaction (Gap-LCR). Nucleic Acids Res. 23:675-82.

Al-Nedawi, et al. 2008. Intercellular transfer of the oncogenic receptor EGFRvIII by microvesicles derived from tumour cells. Nat Cell Biol. 10:619-24.

Armstrong, J. 2016. A Method for Surveying the Long-RNA Lanscape of Exosomes. Cofactor Genomics. <https://cofactorgenomics.com/a-method-for-surveying-the-long-rna-landscape-of-exosomes/>.

Balzar, et al. 1999, The biology of the 17-1A antigen (Ep-CAM). J Mol Med. 77:699-712.

Chen, et al. 2010. Microfluidic isolation and transcriptome analysis of serum microvesicles. Lab Chip. 10(4): 505-511.

Cheruvanky, et al. 2007. Rapid isolation of urinary exosomal biomarkers using a nanomembrane ultrafdtration concentrator. Am J Physiol Renal Physiol. 292:F1657-61.

Cotton, et al. 1988. Reactivity of cytosine and thymine in single-base-pair mismatches with hydroxylamine and osmium tetroxide and its application to the study of mutations. Proc Natl Acad Sci U S A. 85:4397-401.

Enderle, et al. 2016. Poster: XP055437400. Development of a Single-Step Isolation Platform to Analyze Exosomal RNA and Cell-Free DNA in Plasma from Cancer Patients. p. 474.

Enderle, et al. 2015. Characterization of RNA from Exosomes and Other Extracellular Vesicles Isolated by a Nocel Spin Column-Based Method. PLoS One, 10(8): e0136133.

Enderle, et al. 2016. Exosomes as a platform for liquid biopsy in immune oncology. Oncotarget. p. 8839.

Fischer and Lerman. 1979a. Length—independent separation of DNA restriction fragments in two-dimentional gel electrophoresis. Cell. 16:191-200.

Fischer and Lerman. 1979b. Two-dimentional electrophoretic separation of restriction enzyme fragments of DNA. Methods Enzymol. 68:183-91.

Guatelli, et al. 1990. Isothermal, in vitro amplification of nucleic acids by a multienzyme reaction modeled after retroviral replication. Proc Natl Acad Sci U S A. 87:1874-8.

Guidelines V1 Exiqon. A guide to the whole transcriptome and mRNA Sequencing Service Exiqon Services Whole Transcriptome and mRNA NGS Services Guidelines. 2014. XP055437277.

Hahn. 1993. Molecular biology of double-minute chromosomes. Bioessays. 15:477-84.

Kan and Dozy. 1978. Antenatal diagnosis of sickle-cell anaemia by DNA analysis of amniotic-fluid cells. The Lancet. 312(8096): 910-912.

Kan and Dozy. 1978. Polymorphism of DNA sequence adjacent to human ß-globin structural gene: relationship to sickle mutation. PNAS. 75(11): 5631-5635.

Kwoh, et al. 1989. Transcription-based amplification system and detection of amplified human immunodeficiency virus type 1 with a bead-based sandwich hybridization format. Proc Natl Acad Sci U S A. 86:1173-7.

Landergren, et al. 1988. A ligase-mediated gene detection technique. Science. 241:1077-80.

Li, et al. 2008. Replacing PCR with COLD-PCR enriches variant DNA sequences and redefines the sensitivity of genetic testing. Nat Med. 14:579-84.

Li, et al. 2006. BEAMing up for detection and quantification of rare sequence variants. Nat Methods. 3(2): 95-97.

Miele, et al. 1983. Autocatalytic replication of a recombinant RNA, J Mol Biol. 171:281-95.

Miranda, et al. 2010. Nucleic acids within urinary exosomes/microvesicles are potential biomarkers for renal disease. Kidney International. 78(2): 191-199.

Myers, et al. 1985. Detection of single base substitutions by ribonuclease cleavage at mismatches in RNA:DNA duplexes. Science. 230:1242-6.

Nagrath, et al. 2007. Isolation of rare circulating tumour cells in cancer patients by microchip technology. Nature. 450:1235-9.

Nilsson, et al. 2009. Prostate cancer-derived urine exosomes: a novel approach to biomarkers for prostate cancer. British Journal of Cancer. 100: 1603-1607.

Nakazawa, et al. 1994. UV and skin cancer: specific p53 gene mutation in normal skin as a biologically relevant exposure measurement. Proc Natl Acad Sci USA. 91:360-4.

Ogawa, et al. 2016. Next-Generation Sequencing of Protein-Coding and Long Non-Protein-Coding RNAs in Two Types of Exosomes Derived from Human While Saliva. Biol. Pharm. Bull. 39(9): 1496-1507.

Orita, et al. 1989. Detection of polymorphisms of human DNA by gel electrophoresis as single-strand conformation polymorphisms. Proc Natl Acad Sci U S A. 86:2766-70.

Raposo, et al. 1996. B lymphocytes secrete antigen-presenting vesicles. J Exp Med. 183:1161-72.

Saugstad, et al. 2017. Analysis of Extracellular RNA in Cerebrospinal Fluid. Journal of Extracellular Vesicles 6: 1-18.

Shao, et al. 2012. Diagnostic technologies for circulating tumour cells and exosomes. Bioscience Reports. 36(1): e00292-e00292.

Shendure, et al. 2012. The Expanding scope of DNA sequencing. Nature Biotechnology. 30(11): 1084-1094.

Skog, et al. 2008. Glioblastoma microvesicles transport RNA and proteins that promote tumour growth and provide diagnostic biomarkers. Nat Cell Biol. 10:1470-6.

Steemers, et al. 2006. Whole-genome genotyping with the single-base extension assay. Nat Methods. 3:31-3.

(56) References Cited

OTHER PUBLICATIONS

Taylor and Gercel-Taylor. 2008. MicroRNA signatures of tumor-derived exosomes as diagnostic biomarkers of ovarian cancer. Gynecol Oncol. 110:13-21.
Velculescu, et al. 1995. Serial Analysis of Gene Expression. Science. 270(5235): 484-487.
Went, et al. 2004. Frequent EpCam protein expression in human carcinomas. Hum Pathol. 35:122-8.
Yang, et al. 2017. RNA Sequencing to Highlight the Heterogeneity in Circulating Exosomes from Patients with Esophageal Squamous Cell Carcinoma. Abstract only. Journal of Clinical Oncology 35(15): e15546.

* cited by examiner

| GO categories | Counts | P value |
|---|---|---|
| organelle organization | 1868 | 6.00E-110 |
| cellular macromolecule metabolic process | 3655 | 3.63E-108 |
| macromolecular complex subunit organization | 1398 | 8.28E-99 |
| cellular component organization or biogenesis | 2825 | 1.17E-95 |
| cellular nitrogen compound metabolic process | 2912 | 1.45E-95 |
| gene expression | 2470 | 3.09E-95 |
| cellular metabolic process | 4211 | 4.82E-95 |
| mRNA metabolic process | 463 | 1.23E-89 |
| cellular component organization | 2755 | 6.32E-89 |
| macromolecule metabolic process | 3816 | 3.13E-86 |
| metabolic process | 4704 | 4.58E-85 |
| nitrogen compound metabolic process | 2982 | 3.95E-84 |
| nucleobase-containing compound metabolic process | 2547 | 1.17E-83 |
| nucleic acid metabolic process | 2323 | 4.37E-82 |

FIGURE 11

SEQUENCING AND ANALYSIS OF EXOSOME ASSOCIATED NUCLEIC ACIDS

RELATED APPLICATION

This application is a national stage application, filed under 35 U.S.C. 371, of International Application No. PCT/US2017/057916, filed on Oct. 23, 2017, which claims priority to, and the benefit of, U.S. Provisional Application No. 62/410,974, filed Oct. 21, 2016 and U.S. Provisional Application No. 62/536,545, filed Jul. 25, 2017, the disclosure of each of which is herein incorporated by reference in their entirety.

FIELD OF THE INVENTION

The present invention is in the technical field of molecular biology. More particularly, the present invention is in the technical field of molecular diagnostics. In molecular biology, molecules in the form of nucleic acids, such as RNA and DNA, can be isolated from human sample material, such as tissue and various biofluids, and further analyzed with a wide range of methodologies.

BACKGROUND

Comprehensive nucleic acid sequencing, including RNA sequencing, of exosomes and other extracellular vesicles from biofluids holds the promise for extremely sensitive diagnostics and thus detecting disease, patient stratification and monitoring therapy response. The term exosome is here used to depict any extracellular membrane bound vesicle released by cells.

There is a fundamental lack of understanding regarding the long RNA cargo within exosomes isolated from either in vitro or ex vivo systems. Previous studies investigating the RNA cargo of exosomes have largely focused on the small RNA fraction. The relatively small proportion and poor transcript coverage of annotated long RNAs reported in these studies led many to conclude that exosomes carry only short fragments of protein-coding and non-coding RNA and raised questions regarding their potential functional capability in regulation of gene expression and intercellular communication through exosomes.

Current methods of isolating DNA and/or DNA and nucleic acids including at least RNA from extracellular vesicles include ultracentrifugation, ultrafiltration, e.g., using 100 kDa filters, polymer precipitation techniques, and/or filtration based on size. However, there exists a need for alternative methods that are efficient and effective for isolating extracellular vesicles and, optionally, extracting the nucleic acids contained therein, preferably extracellular vesicle RNA, as well as sequencing the nucleic acids contained therein, for use in a variety of applications, including diagnostic purposes.

Accordingly, there is a need for reliable sequencing and analysis of nucleic acids with extracellular vesicles. The present disclosure is directed to these, and other, important ends.

SUMMARY OF THE INVENTION

The present invention provides methods for sequencing nucleic acids from a biological sample comprising providing a biological sample; contacting the biological sample with a solid capture surface under conditions sufficient to retain cell-free DNA and extracellular vesicles from the biological sample on or in the capture surface; contacting the capture surface with a lysis reagent while the cell-free DNA and the extracellular vesicles are on or in the capture surface, thereby releasing the DNA and RNA from the capture surface and producing a homogenate; extracting the DNA, the RNA, or both from the homogenate; selectively removing ribosomal DNA or RNA sequences from the homogenate, or from the extracted DNA, the extracted RNA or both; reverse transcribing the RNA into cDNA; constructing a double-stranded DNA library from the extracted DNA, the reverse-transcribed cDNA, or both the extracted DNA and the reverse-transcribed cDNA; optionally amplifying the DNA, the RNA, or both the DNA and RNA from the library; selectively enriching for nucleic acid sequences from cDNA or double-stranded DNA library; and sequencing the library comprising the cDNA, the double-stranded DNA, or both the cDNA and the double-stranded DNA.

In some embodiments, the method further comprises, before or after selectively removing the ribosomal DNA or RNA sequences, a step of pretreating the homogenate, the extracted RNA, or the extracted DNA and RNA with DNase, such as DNase I and/or modified DNase I. In other embodiments, the method further comprises selectively removing ribosomal DNA or RNA sequences from RNA, cDNA, double-stranded DNA at any step during library construction.

In some embodiments, the method comprises simultaneous sequencing of both RNA and DNA from the biological sample.

In some embodiments, the method further comprises, before or after extracting the DNA, the RNA, or both from the homogenate, a step of adding a spike of exogenous RNA or DNA to the homogenate, and/or to the extracted DNA, the extracted RNA, or both the extracted DNA and RNA. In some embodiments, the method further comprises, before or after extracting the DNA, the RNA, or both from the homogenate, a step of pretreating the homogenate with DNase, such as DNase I, followed by a step of adding into the homogenate a spike of exogenous RNA. In some embodiments, the method further comprises, before or after extracting the DNA, the RNA, or both from the homogenate, a step of adding a spike of exogenous RNA or DNA at a dilution of 1:100, 1:1000, 1:10,000, 1:100,000, 1:1,000,000, 1:10,000,000 to the homogenate, and/or to the extracted RNA, the extracted DNA, or both the extracted DNA and RNA.

In some embodiments, selectively removing ribosomal RNA, cDNA, double-stranded DNA comprises using enzymatic reagents such as, RNase H or restriction enzyme digest; utilizing hybridization-based biotinylated probe enrichment and streptavidin conjugated paramagnetic beads. In some embodiments, selectively enriching for nucleic acid sequences from RNA, cDNA, and/or double-stranded DNA library utilizing PCR-based approaches, complementary oligonucleotides, and/or hybridization-based biotinylated probe enrichment and streptavidin conjugated paramagnetic beads. In some embodiments, RNA, cDNA, and/or double-stranded DNA molecules are tagged with unique molecular indices (unique molecular tags, unique identifiers, random barcodes), which enables identification of template, de-duplication, error correction, and copy number enumeration. The unique molecular indices can be appended via primer annealing, adapter ligation, and enzymatic approaches.

In some embodiments, the nucleic acid comprises long RNA having more than 200 nucleotides, such as more than 300 nucleotides, or even more than 500 nucleotides.

In some embodiments, the biological sample contains a volume as low as about 0.5 mL, such as a volume of about 0.5 mL to about 20 mL, about 0.5 mL to about 10 mL, about 0.5 mL to about 5 mL, about 0.5 mL to about 4 mL, or even about 0.5 mL to about 2 mL. In some embodiments, the biological sample is selected from the group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the biological sample is blood, plasma or serum.

In some embodiments, the solid capture surface is a membrane, such as a column membrane, or is a bead. The solid capture surface can be a membrane comprising regenerated cellulose. The solid capture surface can be a membrane having a pore size in a range between 2-5 µm, or of at least 3 µm. The solid capture surface can comprise more than one membrane, such as at least two membranes, or even at least three membranes. The solid capture surface can comprise three membranes, wherein the three membranes are directly adjacent to one another.

In some embodiments, the solid capture surface is magnetic. In some embodiments, the solid capture surface is a bead which is an ion exchange (IEX) bead, is positively charged, or is negatively charged. The solid capture surface can be functionalized with quaternary amine, sulfate, sulfonate, tertiary amine, or a combination thereof. The solid capture surface can be functionalized with quaternary ammonium $R-CH_2-N^+(CH_3)_3$.

In some embodiments, the solid capture surface comprises an IEX bead which is a magnetic, high capacity IEX bead, such as a strong ferromagnetic, high capacity bead, or even a strong ferromagnetic, high capacity, iron oxide-containing magnetic polymer. The solid capture surface can comprise an IEX bead having no surface exposed to the liquid that is prone to oxidization. The solid capture surface can comprise an IEX bead having a high ratio of bead charge to exposed surface.

In some embodiments, the extracting step further comprises adding protein precipitation buffer to the homogenate prior to extraction of the DNA, the RNA, or both the DNA and RNA from the homogenate. In some embodiments, the extracting step further comprises an enzymatic digestion. The extracting step can comprise a proteinase digestion. In some embodiments, the extracting step is performed with or without previous elution of material from the solid surface. In some embodiments, the extracting step comprises a digestion using proteinase. DNAse, RNase, or a combination thereof. In some embodiments, the extracting step further comprises a protein precipitation buffer which comprises a transition metal ion, a buffering agent, or both a transition metal ion and a buffering agent.

In some embodiments, the method further comprises processing the biological sample by filtering the biological sample, such as by filtering using a 0.8 µm filter. In some embodiments, the method further comprises a centrifugation step after contacting the biological sample with the capture surface. In some embodiments, the method further comprises washing the capture surface after contacting the biological sample with the capture surface.

In some embodiments, the method further comprises adding a nucleic acid control spike-in to the homogenate.

In some embodiments, the method further comprises steps of binding of protein precipitated-eluate to a silica column; and eluting the extraction from the silica column. In some embodiments, the method is used for high throughput isolation of nucleic acids from the biological samples. In some embodiments, the method comprises using one or multiple chemicals to enhance the binding of small RNAs to the solid surface, such as optimal concentration of isopropanol, sodium acetate and glycogen. In some embodiments, the method utilizes an optimal combination of binding conditions selected from the group consisting of encompass concentration of cations, concentration of anions, detergents, pH, time and temperature, and any combination thereof.

Various aspects and embodiments of the invention will now be described in detail. It will be appreciated that modification of the details may be made without departing from the scope of the invention. Further, unless otherwise required by context, singular terms shall include pluralities and plural terms shall include the singular.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

FIG. 11 tabulates the top gene ontology categories found to be represented in plasma exosomal long RNA.

DETAILED DESCRIPTION OF THE INVENTION

The present invention provides a series of steps that prepare nucleic acids (RNA and/or DNA) isolated from exosomes for sequencing. This enables a wide diversity of RNAs and/or DNAs, to be efficiently detected. These can then be used to identify various attributes such as gene expression, alternative splicing, fusion transcripts, circular RNA and the detection of both somatic and germline mutations including single nucleotide variants (SNV) and structural variations (insertions/deletions, fusions, inversions).

In an embodiment, the present invention provides the ability to combine multiple workflows, e.g., separate processing conditions for RNA and DNA, into a single workflow to allow for analysis of exosomal samples in a more efficient way.

In an embodiment, the present invention provides a workflow that specifically enriches the samples for targets of interest, enabling deeper sequence coverage. The workflow provides the ability to target capture cDNA or dsDNA in a particular sample by, e.g., enriching the sample for a subset of genes of interest and/or by depleting other genes which are not of interest.

According to an embodiment, the present invention provides a platform specifically designed to include both short and long RNA transcripts from exosomes into the RNA sequencing workflow. As used herein, the term "long RNA" refers to RNA having greater than 200 nucleotides, such as more than 300 nucleotides, or even more than 500 nucleotides and can include long non-coding RNA. mRNA, and circular RNA.

According to an embodiment, the present invention provides a platform to process DNA, either alone or in mixture with RNA (both short and long RNA transcripts) from exosomes into a sequencing workflow.

Figure 16:
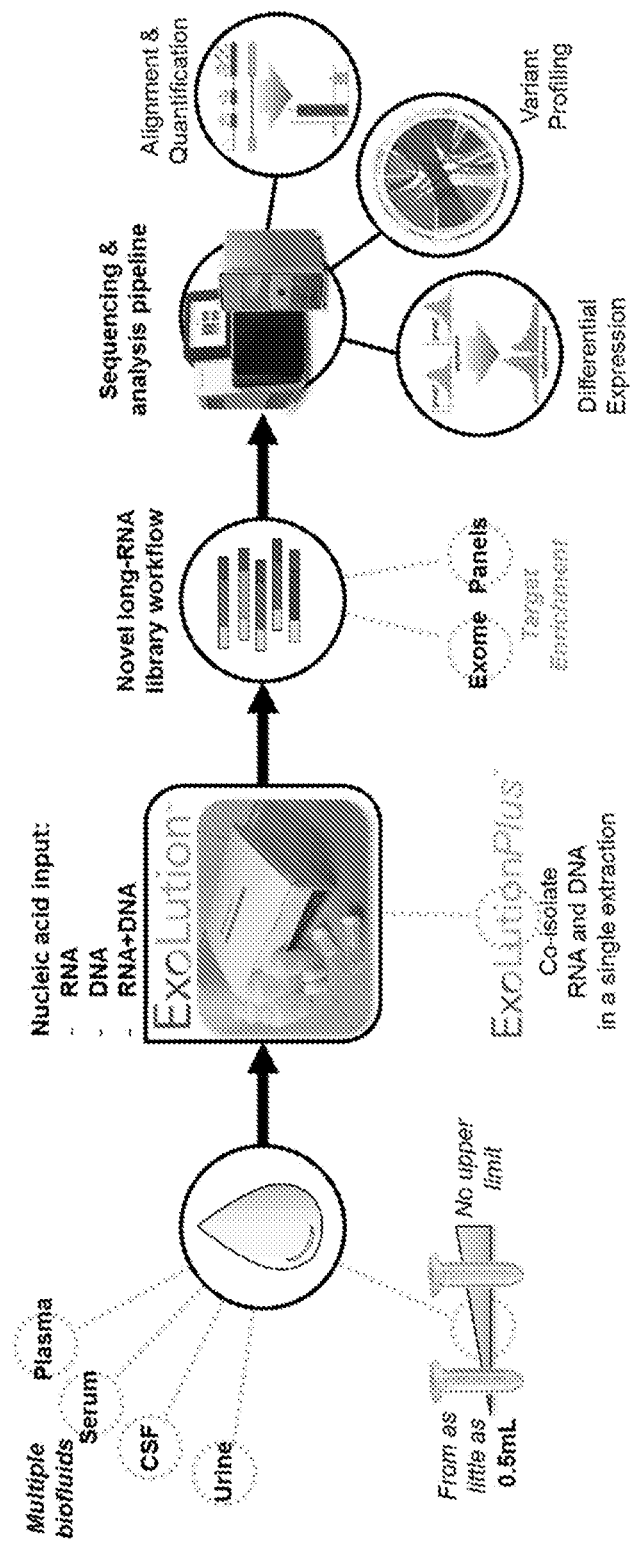
FIG. 16 provides an overview of RNASeq pipeline.

The volume of the biofluid serving as input for the sequencing workflow can be as low as ≥0.5 ml with no upper limit (FIG. 16).

Starting with a biological sample as described herein, e.g., human plasma, serum, blood, urine, cerebrospinal fluid, and the like, nucleic acids are isolated from exosomes and other cell-free sources. Alternatively, the nucleic acids can originate from tissue sources such as reference standards and FFPE materials.

Figure 17:
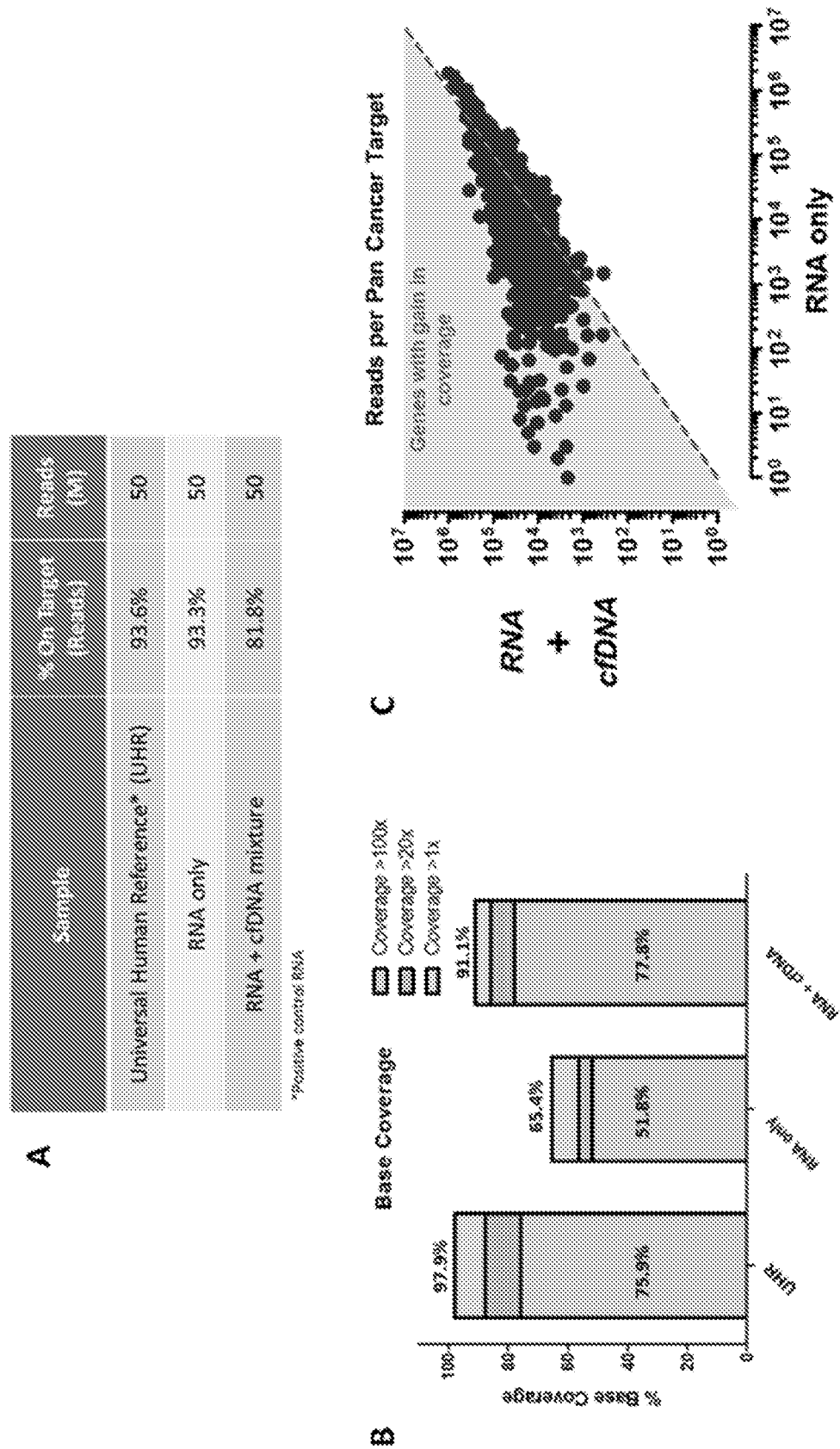
FIG. 17 shows the mapping metrics (FIG. 17A), the base coverage of UHR, RNA only, and RNA+cfDNA as % of base coverage (FIG. 17B), and a plot of reads per pan cancer target (FIG. 17C).

Exosomal derived nucleic acids can include RNA or DNA, either individually or as a mixture of RNA and DNA, as shown in FIGS. 17 (RNA & RNA+DNA) and 18 (DNA & RNA+DNA) which illustrate the sequencing of these nucleic acid combinations. Exosomal derived nucleic acids can include material either contained within or bound to the outer surface of exosomes. The DNA component can be exosomal or other cell-free sources (cfDNA).

In an embodiment, the isolation methods for exosomes for the further purification of extracellular vesicles having associated nucleic acids described herein also include: 1) Ultracentrifugation, often in combination with sucrose density gradients or sucrose cushions to float the relatively low-density exosomes. Isolation of exosomes by sequential differential centrifugations, combined with sucrose gradient ultracentrifugation, can provide high enrichment of exosomes. 2) The use of volume-excluding polymer selected from the group consisting of polyethylene glycol, dextran, dextran sulfate, dextran acetate, polyvinyl alcohol, polyvinyl acetate, or polyvinyl sulfate; and wherein the molecular weight of the volume-excluding polymer is from 1000 to 35000 daltons performed in conjunction with the additive sodium chloride from 0-1M. 3) Size exclusion chromatography, for example, Sephadex™ G200 column matrix. 4) Selective immunoaffinity or charge-based capture using paramagnetic beads (including immuno-precipitation), for example, by using antibodies directed against the surface antigens including but not limited to EpCAM, CD326, KSA, TROP1. The selection antibodies can be conjugated to paramagnetic microbeads. 5) Direct precipitation with chaotropic agents such as guanidinium thiocyanate.

Following exosome isolation, samples are subjected to the methods as described. Briefly, in an embodiment, the workflow starts with exosome RNA isolation and is followed by DNase treatment for applications where DNA could interfere in the analysis.

In another embodiment, following exosome RNA isolation, the sample can either be treated with DNase or left untreated. In some embodiments, DNase treatment is useful for applications where DNA could interfere in the analysis. In other embodiments, the sample is left untreated where DNA contribution is of interest in the analysis.

DNase treatments contemplated herein include wildtype DNase I as well as its protein engineered or otherwise modified forms. Commercially available examples include, without limitation, ArcticZymes: Heat & Run gDNA removal kit; New England Biolabs: DNase I; Sigma Aldrich: DNase I; ThermoFisher Scientific: Turbo DNase; and ThermoFisher Scientific: Ambion DNase 1.

In some embodiments, a spike-in of synthetic RNA or DNA standard, also referred to herein as a "synthetic spike-in" is performed, either before or after the DNase step as a quality control metric, or at any step prior to sequencing library preparation. Exogenous materials such as synthetic nucleic acids, can serve as sample quality control reagents, quantification reagents, can enable limit of detection, dynamic range and technical reproducibility studies and/or can enable studies detecting particular sequences.

Commercially available synthetic spike-ins include, without limitation, Dharmacon: Solaris RNA spike-in control kit; Exiqon: RNA spike-in kit; Horizon Diagnostics: Reference standards, Lexogen: spike-in RNA variant control mixes; Thermo Fisher Scientific: ERCC RNA spike-in control mixes; and Qbeta RNA spike-in, yeast or *Arabidopsis* RNA.

In some embodiments, the synthetic spike-ins is added to the sample at different dilutions. In some embodiments, the dilution of the spike-ins to be added to the sample can be in the range of 1:1000 to 1:10,000,000, including, without limitation, dilutions of 1:1000, 1:10,000, 1:100,000, 1:1,000,000 and even 1:10,000,000. The specific dilution of spike-ins to be added to the sample is determined based on the quantity and/or the quality and/or source of the nucleic acids present in the sample.

Next, the sample can either be subjected to a reverse transcription reaction or untreated. In some embodiments, the RNA within a sample is reverse transcribed when it is of interest to convert the RNA to cDNA. In some embodiments, only first stand synthesis is conducted when only single stranded cDNA is desired. In some embodiments, both first strand and second strand synthesis is conduced when double stranded DNA is desired. In some embodiments, the sample is untreated when it is of interest to only investigate DNA fractions within the sample. In some embodiments, the cDNA processing steps include, for example but not limited to retaining strand information by treating with uracil-N-glycosylase and/or by orientation of NGS adapter sequences, cleavage of RNA, fragmentation of RNA, incorporation of non-canonical nucleotides, annealing or ligation of adapter sequences, second strand synthesis, etc.

In some embodiments, the sample is subjected to fragmentation or untreated. Fragmentation can be achieved using enzymatic or non-enzymatic processes or by physical shearing of the material with RNA or dsDNA. In some embodiments, fragmentation of the RNA and/or dsDNA is conducted by heat denaturation in the presence of divalent cations. The specific duration of fragmentation time of the sample is determined based on the quantity and/or the quality and/or source of the nucleic acids present in the sample. In some embodiments, the duration of fragmentation time ranges from 0 minute to 30 minutes.

In some embodiments, sequencing adaptors are added to the material using ligation based approaches following end-repair and polyadenylation. In some embodiments, sequencing adaptors are added to the material using PCR-based approaches. Nucleic acids within the sample, which have gone through any of the embodiments described above and now have sequence adaptors will hereto be described as 'library' when referring to the entire collection of nucleic acid fragments within the sample or 'library fragment' when referring to the fragment of nucleic acid that has been incorporated within the context of the sequence adaptors. Inclusion of unique molecular index (UMI), unique identifier, or molecular tag in the adapter sequence provides an added benefit for read de-duplication and enhanced estimation of the input number of nucleic acid molecules in the sample.

In some embodiments, using bead-based separation techniques, the library can be subjected to a process whereby composition of the library can be further modified to: 1) remove unwanted products (including but not restricted to; residual adaptors, primers, buffers, enzymes, adaptor dimers); 2) be of a certain size range (by altering the bead or bead buffer reagent to sample ratio, low and/or high molecular weight products can be either included or excluded in the sample); 3) concentrate the sample by elution in minimal volume. This process is commonly referred to as a 'clean up' step or the sample is 'cleaned up' and will hereto be referred to as such. Bead-based separation techniques can include but are not limited to paramagnetic beads. Bead-based clean up can be conducted once or multiple times if required or desired.

Commercially available paramagnetic beads useful according to the methods herein include, without limitation, Beckman Coulter: Agencourt AMPure XP; Beckman Coulter: Agencourt RNAclean XP; Kapa Biosystems: Kapa Pure beads; Omega Biosystems: MagBind TotalPure NGS beads; and ThermoFisher Scientific: Dynabeads.

In some embodiments, the beads are subjected to a hydration step, wherein the dried beads are covered in a hydrating liquid such as water, and in particular, nuclease-free water, resuspended, and allowed to incubate at a temperature in the range of about 20° C. to about 40° C., such as about 20° C. to about 25° C., and for a time from about 1 minute to about 10 minutes, such as about 5 minutes to about 10 minutes. In a preferred embodiment, the beads are allowed to incubate at room temperature for 5 minutes to rehydrate.

In some embodiments, following bead-based clean up, the library is amplified en masse using universal primers that target the adaptor sequence. The number of amplification cycles can be modified to produce enough product that is required for downstream processing steps. In some embodiments, fewer cycles will be used in order to minimize introduction of possible biases. In some embodiments, more cycles will be used to produce a library with higher concentration of molecules. In some embodiments, an optional round of qPCR is performed to determine the optimal number of cycles for PCR amplification of the library. Following library amplification, bead-based clean up is repeated again as described above.

Next library quantity and quality is quantified using, but not limited to, fluorometric techniques such as Qubit dsDNA HS assay and/or Agilent Bioanalyzer HS DNA assay.

Figure 18:
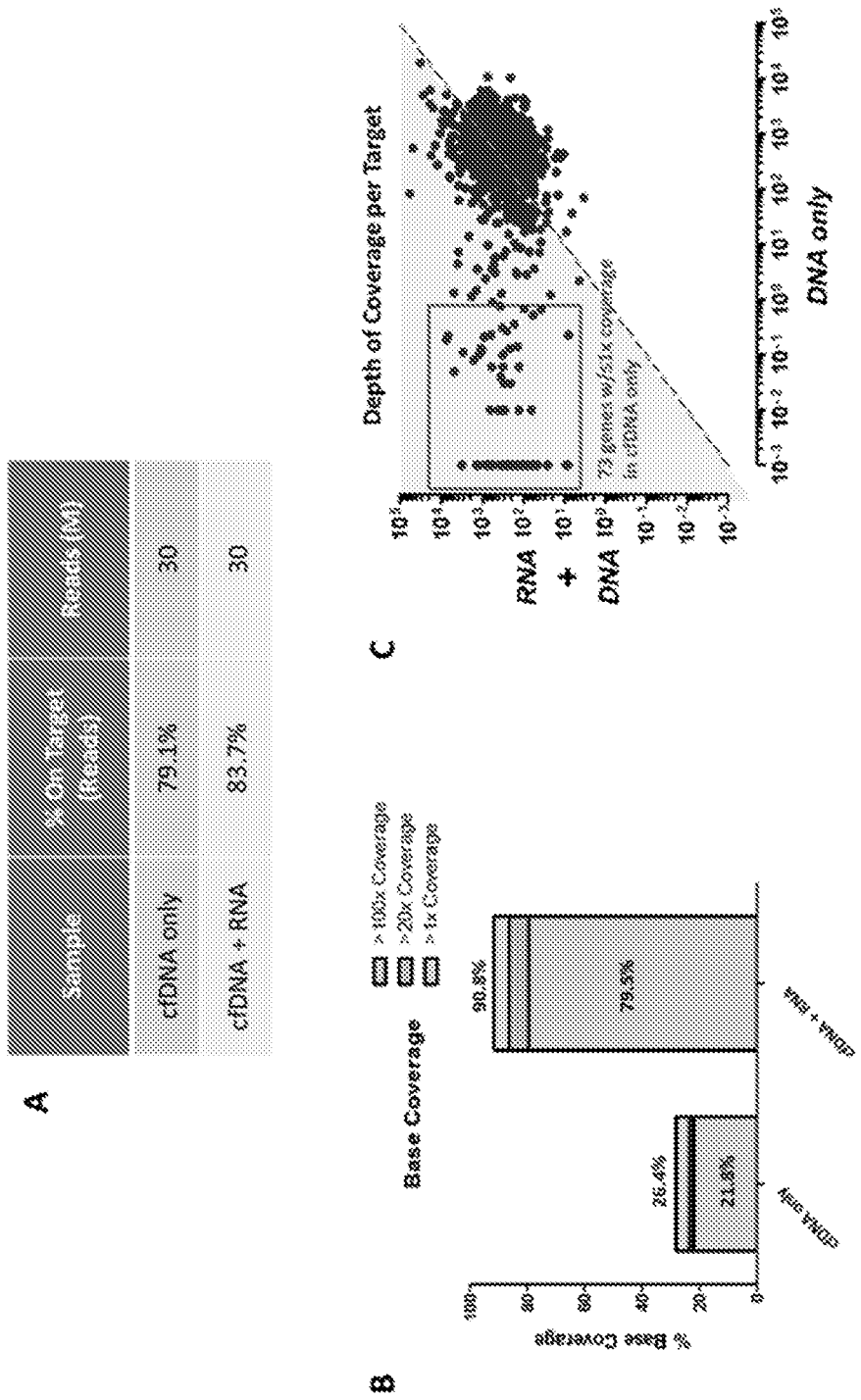
FIG. 18 shows the mapping metrics (FIG. 18A), the base coverage of cfDNA and cfDNA+RNA as % of base coverage (FIG. 18B) and a plot of depth of coverage per target (FIG. 18C).
Figure 19:
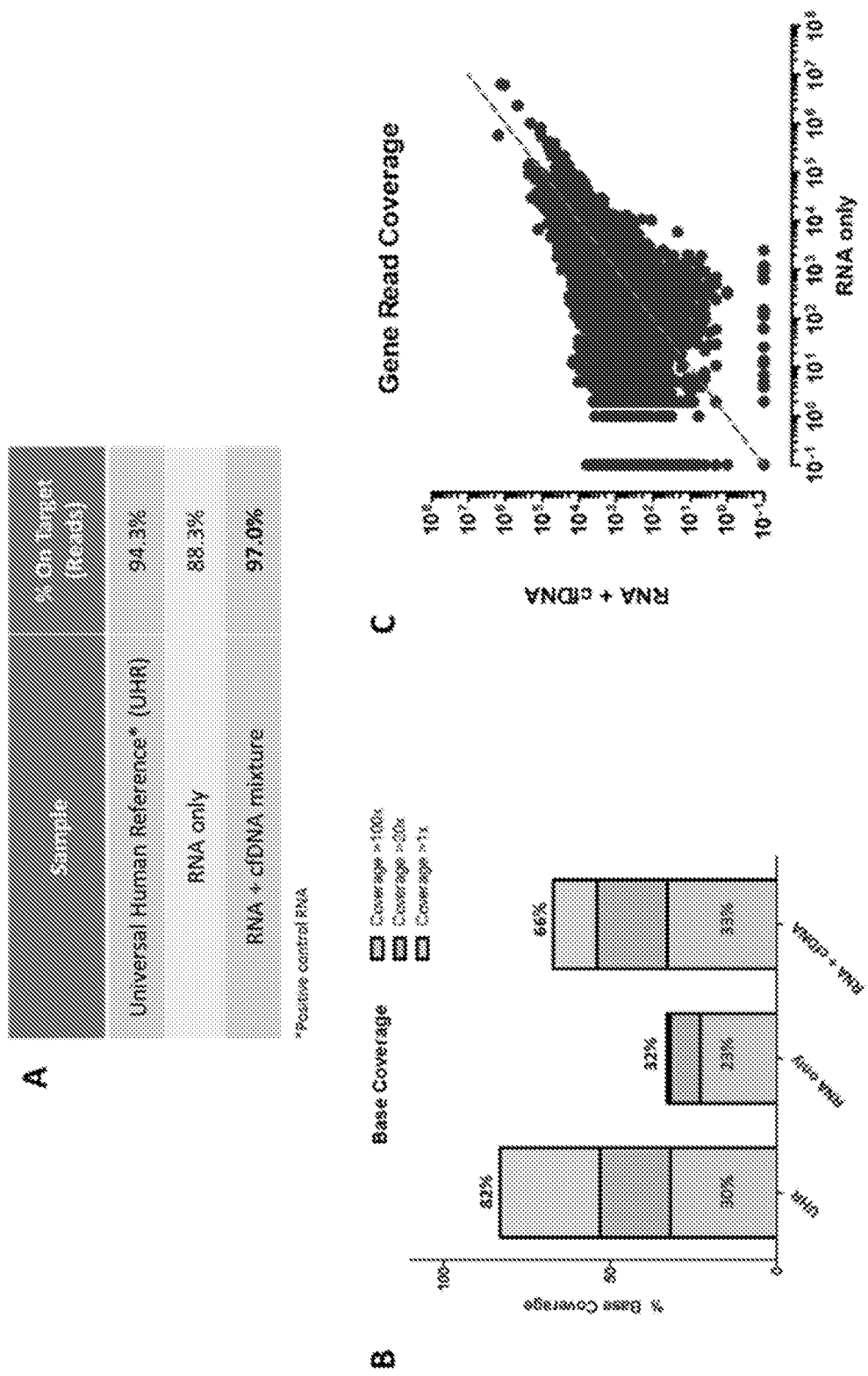
FIG. 19 shows the mapping metrics (FIG. 19A), the base coverage of UHR, RNA only, and RNA+cfDNA as % of base coverage (FIG. 19B), and a plot of gene read coverage (FIG. 19C).
Figure 20:
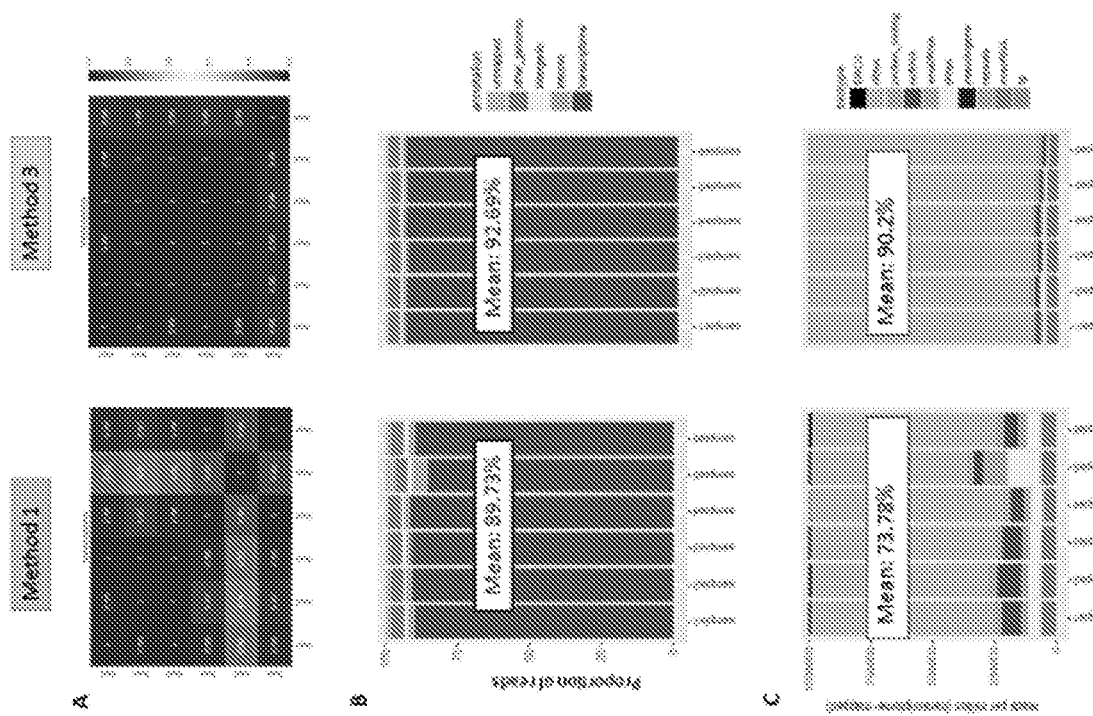
FIG. 20 plots three independent RNAseq library preparation workflows optimized for liquid biopsy.

In some embodiments, an aliquot of the sample can be taken to a hybridization-based enrichment process (refer to FIGS. 17-19). This process utilizes hybridization of nucleotide probes complementary to genome sequence regions of interest contained within the sample followed by a series of washes utilizing buffers that select for the sequence of interest, while washing away unwanted material. Probe-sequence hybrids can be selected for utilizing, but not limited to, streptavidin-biotin chemistries. The process can be used to enrich any portion or mixture of genomic or transcriptomic sequence including but not limited to exonic regions, untranslated regions (UTR), intergenic regions and intronic regions, which can cover the full gene coding region or specific hotspot location within or outside the gene. Hybridization probe panels can be used to enrich any number of target sequences from small numbers of targets (1 or 20) to many targets (>1,000) including, but not limited to, the total protein coding transcriptome with ~20,000 genes (see FIG. 4), total non-coding transcriptome including long non-coding, long intergenic non-coding, repeats such as Alu, HerV, Line, etc, antisense and small noncoding transcriptome or any combination of the above, large panels targeting broad disease or disease related pathways, Pathological state with >1.000 genes or fewer (see FIGS. 17-18), and moderate panels targeted focused diseases or disease related pathways with 50-500 genes (e.g. solid tumor). In some embodiments, the samples will not be enriched, in which case the total sample will be sequenced (FIGS. 20-22). Exemplary commercial hybridization kits include, for example, Agilent's SureSelect Exome V2; ArcherDx's Comprehensive Solid Tumor; Asuragen Quantidex NGS Pan Cancer Kit; ClonTech's SMARTer Target RNA Capture; IDT's Pan-Cancer Panel; Illumina's Trusight RNA Pan-Cancer Panel; Illumina's TruSight Tumor 170; Illumina's RNA Access; New England BioLabs's NEBNext Direct Cancer HotSpot Panel; NuGEN's Ovation Fusion Panel Target Enrichment System V2; Roche's SeqCap EZ Exome v3.0 Kit; and Roche's Avenio ctDNA Expanded Kit.

In some embodiments when total sample is being analyzed, ribosomal sequence (cDNA, RNA, or cfDNA) can sometimes affect the detection of low abundant transcripts, in which case it is desirable to remove or deplete the sample of ribosomal sequences (see FIG. 21), also referred to herein as "ribodepletion". The selective removal of abundant but undesirable sequences, including but not limited to ribosomal sequences and/or globin gene sequences can be accomplished at level of RNA sequence, which is appropriate when only RNA has been isolated and is being analyzed, or at the dsDNA (library) level, which is appropriate when cDNA and/or cfDNA is being analyzed. Ribosomal sequence specific depletion can be accomplished using enzymatic reagents similar to, but not limited to, RNase H or restriction enzyme digest. Depletion can also be achieved utilizing hybridization-based biotinylated probe enrichment and streptavidin conjugated paramagnetic beads to specifically capture and remove ribosomal sequences.

In some embodiments, ribosomal depletion can also include one or more additional cycles of primer annealing, such as one additional cycle, two additional cycles, three additional cycles, or five or more additional cycles.

In some embodiments, following hybridization-based target enrichment or ribosomal depletion processes, the remaining sample material will be amplified using universal primers that recognize the sequencing adaptors. PCR-based amplification will use as many cycles as required to generate a sufficient amount of product for subsequent steps, without using excess cycles that potentially introduce bias into the material.

In some embodiments, following hybridization-based target enrichment and/or ribosomal depletion processes, the remaining sample material will be cleaned up using a bead-based paramagnetic approaches as described above. Cleaning can occur either before, after, or both before and after additional amplification cycles as described above.

In some embodiments, this is followed by quantification of library quantity and quality using, but not limited to, fluorometric techniques such as Qubit dsDNA HS assay and/or Agilent Bioanalyzer HS DNA assay. The libraries can then be normalized, multiplexed and subjected to sequencing on any next generation sequencing platform.

Figure 24:
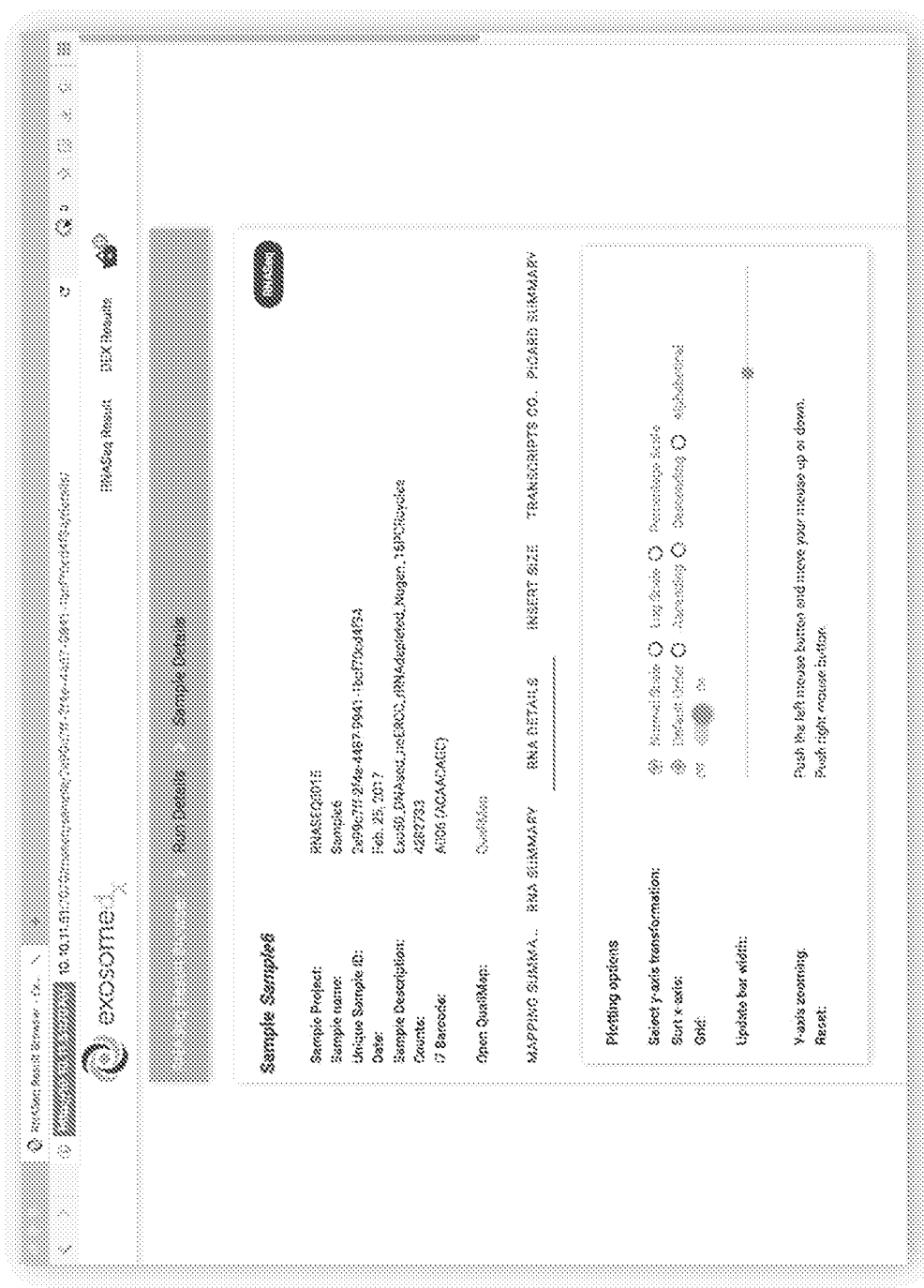
FIG. 24 is an RNASeq browser to display QC metrics and analysis results.
Figure 25:
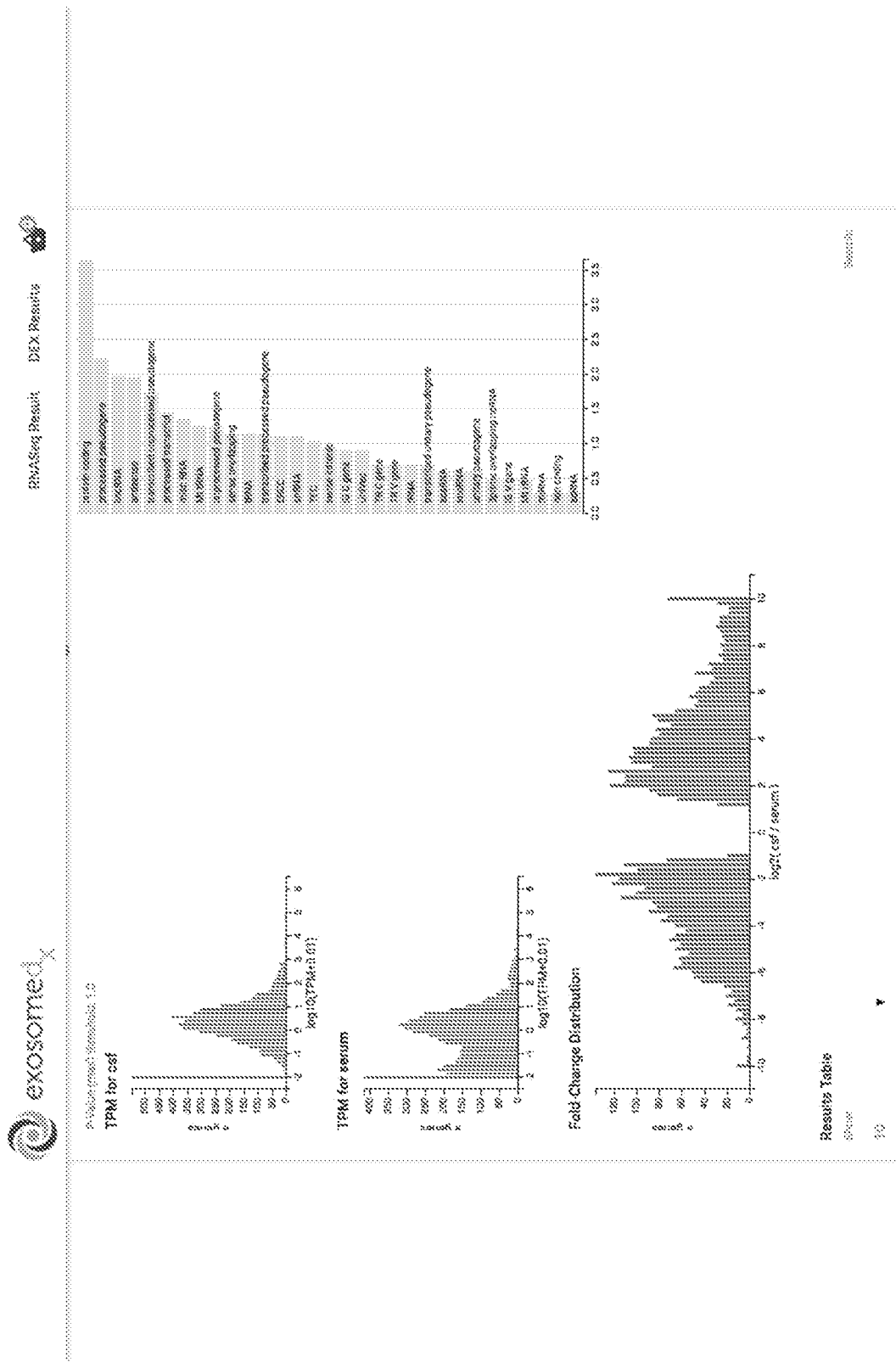
FIG. 25 is a differential expression browser to display and evaluate the results of differential expression analyses.

In some embodiments, the sequencing data is then demultiplexed if necessary and transcript/gene counts are generated by either mapping against an existing genome or transcriptome reference sequence or against de novo assembled genomes or transcripts (see FIG. 16, FIG. 24). The UMI tags on each sequence can then be used to identify fragments that arise due to PCR duplication. The counts are normalized among others for library size, GC-bias, sequence-bias, sequencing depth. These counts can then be used to perform gene expression analysis, differential expression analysis between samples pertaining to different conditions (e.g. tumor/normal) to generate a list of potential biomarkers but not limited to the said application that can discriminate between the sample types (FIG. 25). The reference aligned data can be used for profiling sequence variation such as but not limited to single nucleotide polymorphisms, insertions/deletions, fusions, inversions and repeat expansions.

Sample Isolation

The present invention provides methods of sequencing and/or analyzing nucleic acids including at least RNA from extracellular vesicles by capturing the cell-free DNA and the extracellular vesicles to a surface, subsequently lysing the extracellular vesicles to release the nucleic acids, particularly RNA, contained therein, and eluting the DNA and/or DNA and nucleic acids including at least RNA from the capture surface.

Microvesicles are shed by eukaryotic cells, or budded off of the plasma membrane, to the exterior of the cell. These membrane vesicles are heterogeneous in size with diameters ranging from about 10 nm to about 5000 nm. All membrane vesicles shed by cells <0.8 µm in diameter are referred to herein collectively as "extracellular vesicles" or "microvesicles." These extracellular vesicles include microvesicles, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles."

Exosomes are known to contain RNA types including mRNA (messenger RNA) and miRNA (micro RNA). However, there is a fundamental lack of understanding regarding the long RNA cargo within exosomes isolated from either in vitro or ex vivo systems. Previous studies investigating the RNA cargo of exosomes have largely focused on the small RNA fraction. The relatively small proportion and poor transcript coverage of annotated long RNAs reported in these studies led many to conclude that exosomes carry only short fragments of protein-coding and non-coding RNA and raised questions regarding their potential functional capability in regulation of gene expression and intercellular communication through exosomes.

As shown herein, there is a wide diversity of RNA in plasma exosomes. RNA types that have been identified according to the methods herein include the RNA types identified in FIG. 5. In some embodiments, the RNA types identified by the methods herein include, without limitation, ribosomal RNA, SINE RNA, LINE RNA, Alu RNA, HERVs, globin RNA, as well as other types of long non-coding RNAs and/or repeat sequences as described elsewhere, such as at gencodegenes.org/gencode_biotypes.html.

The methods and kits isolate and extract nucleic acids, e.g., DNA and/or DNA and nucleic acids including at least RNA from a sample using the following general procedure. First, the nucleic acids in the sample, e.g., the DNA and/or the DNA and the extracellular vesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from the extracellular vesicles is then isolated from the protein-precipitated eluate using any of a variety of art-recognized techniques, such as, for example, binding to a silica column followed by washing and elution.

In some embodiments, the elution buffer comprises a denaturing agent, a detergent, a buffer substance, and/or combinations thereof to maintain a defined solution pH. In some embodiments, the elution buffer includes a strong denaturing agent. In some embodiments, the elution buffer includes a strong denaturing agent and a reduction agent.

In some embodiments, the elution buffer contains guanidine thiocyanate (GTC), a denaturing agent that disrupts vesicle membranes, inactivates nucleases, and adjusts ionic strength for solid phase adsorption.

In some embodiments, the elution buffer contains a detergent such as, for example, Tween, Triton X-100, etc., to assist in the disruption of extracellular vesicle membranes and to support efficient elution of the biomarkers from the capture surface.

In some embodiments, the elution buffer contains a reducing agent such as β-Mercaptoethanol (BME), to reduce intramolecular disulfide bonds Cys-Cys and to assist in denaturing proteins especially RNases present in the eluate.

In some embodiments, the elution buffer contains GTC, a detergent, and a reducing agent.

In some embodiments, the transition metal ion in the protein precipitation buffer is zinc. In some embodiments, the zinc is present in the protein precipitation buffer as zinc chloride.

In some embodiments, the buffering agent in the protein precipitation buffer is sodium acetate (NaAc). In some embodiments, the buffering agent is NaAc at pH ≤6.0.

In some embodiments, the protein precipitation buffer includes zinc chloride and NaAc buffering agent at pH ≤6.0.

Current methods of isolating DNA and/or DNA and nucleic acids including at least RNA from extracellular vesicles include hazardous substances, ultracentrifugation, ultrafiltration, e.g., using 100 kD filters, polymer precipitation techniques, and/or filtration based on size. However, there exists a need for alternative methods that are efficient and effective for isolating extracellular vesicles and, optionally, extracting the nucleic acids contained therein, for example, in some embodiments, extracellular vesicle RNA, for use in a variety of applications, including diagnostic purposes.

The isolation and extraction methods and/or kits provided herein use a spin-column based purification process using an affinity membrane that binds cell free DNA and/or microvesicles. The methods and kits of the disclosure allow for the capability to run large numbers of clinical samples in parallel, using volumes from 0.2 up to 4 mL on a single column. The cell-free DNA isolated using the procedures provided herein is highly pure. The isolated RNA is highly pure, protected by a vesicle membrane until lysis, and intact vesicles can be eluted from the membrane. The procedure is able to deplete substantially all cell-free DNA from plasma input, and is equal to or better in DNA yield when compared to commercially available circulating DNA isolation kits. The procedure is able to deplete substantially all mRNA from plasma input, and is equal or better in mRNA/miRNA yield when compared to ultracentrifugation or direct lysis. In contrast to commercially available kits and/or previous isolation methods, the methods and/or kits enrich for the microvesicle bound fraction of miRNAs, and they are easily scalable to large amounts of input material. This ability to scale up enables research on interesting, low abundant transcripts. In comparison with other commercially available products on the market, the methods and kits of the disclosure provide unique capabilities that are demonstrated by the examples provided herein.

The methods and kits isolate and extract nucleic acids, e.g., DNA and/or DNA and nucleic acids including at least RNA from a biological sample using the following general procedure. First, the sample, including the cfDNA and the extracellular vesicle fraction, is bound to a membrane filter, and the filter is washed. Then, a GTC-based reagent is used to perform on-membrane lysis and release of the nucleic acids. e.g., DNA and/or DNA and RNA. Protein precipitation is then performed. The nucleic acids, e.g., DNA and/or DNA and RNA, is then bound to a silica column, washed and then eluted. The extracted nucleic acids, e.g., DNA and/or DNA and RNA, can then be further analyzed, for example, using any of a variety of downstream assays.

In some embodiments, the nucleic acid is isolated according to the following steps. After addition of the lysis reagent, a protein precipitation buffer is then added to the homogenate, and the solution is mixed vigorously for a brief time period. The solution is then centrifuged for 3 min at 12,000×g at room temperature. The solution can then be processed using any of a variety of art-recognized methods for isolating and/or extracting nucleic acids.

The isolated nucleic acids, e.g., DNA and/or DNA and RNA, can then be subject to further analysis using any of a variety of downstream assays. In some embodiments, the combined detection of DNA and RNA is used to increase the sensitivity for actionable mutations. There are multiple potential sources of detectable mutations in circulating nucleic acids. For example, living tumor cells are a potential source for RNA and DNA isolated from the extracellular vesicle fraction of a sample, and dying tumor cells are potential sources for cell-free DNA sources such as, for example, apoptotic vesicle DNA and cell-free DNA from necrotic tumor cells. As mutated nucleic acids are relatively infrequent in circulation, the maximization of detection sensitivity becomes very important. Combined isolation of DNA and RNA delivers comprehensive clinical information to assess progression of disease and patient response to therapy. However, in contrast to the methods and kits provided herein, commercially available kits for detecting circulating nucleic acids are only able to isolate cfDNA from plasma. i.e., from dying cells. Those of ordinarily skill in the art will appreciate that more copies of a mutation or other biomarker leads to enhanced sensitivity and accuracy in identifying mutations and other biomarkers.

The methods of the disclosure can be used to isolate all DNA from plasma samples. The methods of the disclosure separate RNA and DNA at similar levels for the same sample volume, and the RNA and DNA can be separated from each other. These methods of the disclosure capture the same or more cell-free DNA (cfDNA), the same or more mRNA and much more miRNA than a commercially available isolation kit.

The methods of the disclosure can also be used for co-purification of RNA and DNA. The methods of the disclosure (also referred to herein as procedures) can be used to isolate RNA and DNA from exosomes and other extracellular vesicles using 0.2-4 mL, such as 0.5-4 mL of plasma or serum. The list of compatible plasma tubes includes plasma with the additives EDTA, sodium citrate, and citrate-phosphate-dextrose. Plasma containing heparin can inhibit RT-qPCR.

The sample, alone or diluted with a binding buffer, is then loaded onto the spin column having a capture membrane and spun for 1 min at 500×g. The flow-through is discarded, and the column is then placed back into the same collection tube. Wash buffer is then added and the column is spun for 5 min at 5000×g to remove residual volume from the column. Note: After centrifugation, the spin column is removed from the collection tube so that the column does not contact the flow-through. The spin column is then transferred to a fresh collection tube, and the GTC-based elution buffer is added to the membrane. Then, the spin column is spun for 5 min at 5000×g to collect the homogenate containing the lysed exosomes. Protein precipitation is then performed.

The methods provided herein are useful for isolating and detecting DNA from biological samples. Vesicle RNA is thought to be derived from living cells in e.g. the diseased tissue. Cell-free DNA cfDNA) is thought to be derived from dying cells e.g. necrotic cells in the disease tissue. Thus, cfDNA is useful as an indicator of therapeutic response, while the RNA is an indicator of resistance mutations on the rise.

The methods provided herein are useful for detection of rare mutations in blood, as the method provides a sufficiently sensitive method that can be applied on nucleic acids of sufficient amount. The amount of actual DNA and RNA molecules in biofluids is very limited, and the methods provide an isolation method that extracts all molecules of the blood that are relevant for mutation detection in a volume small enough for effective downstream processing and/or analysis.

In some embodiments, the sample isolation and analysis techniques encompass the methods referred to as EXO50 and/or EXO52 as described in, e.g., WO 2014/107571 and WO 2016/007755, each incorporated by reference herein in the entirety. Also contemplated are the commercially available liquid biopsy platforms sold under the trademarks EXOLUTION™, EXOLUTION PLUS™, EXOLUTION™ UPREP, EXOLUTION HT™, UPREP™, EXOEASY™, EXORNEASY™, each available from Exosome Diagnostics, Inc., as well as the QIAamp Circulating Nucleic Acids Kit, DNeasy Blood & Tissue Kits, AllPrep DNA/RNA Mini Kit, and the AllPrep DNA/RNA/Protein Mini Kit, each available from Qiagen.

As used herein, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

As used herein, the term "biological sample" refers to a sample that contains biological materials such as DNA, RNA and protein.

In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some embodiments, the biological sample may suitably comprise cell culture supernatant.

In some embodiments, the biological sample may suitably comprise a tissue sample from a subject. The tissue sample can be isolated from anywhere in the body of the subject.

A suitable sample volume of a bodily fluid is, for example, in the range of about 0.1 ml to about 30 ml fluid. The volume of fluid may depend on a few factors, e.g., the type of fluid used. For example, the volume of serum samples may be about 0.1 ml to about 4 ml, for example, in some embodiments, about 0.2 ml to about 4 ml. The volume of plasma samples may be about 0.1 ml to about 4 ml, for example, in some embodiments, 0.5 ml to 4 ml. The volume of urine samples may be about 10 ml to about 30 ml, for example, in some embodiments, about 20 ml.

While the examples provided herein used plasma samples, the skilled artisan will appreciate that these methods are applicable to a variety of biological samples.

The methods and kits of the disclosure are suitable for use with samples derived from a human subject. In addition, the methods and kits of the disclosure are suitable for use with samples derived from a non-human subject such as, for example, a rodent, a non-human primate, a companion animal (e.g., cat, dog, horse), and/or a farm animal (e.g., chicken).

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. Etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

While the working examples provided herein use a membrane as the capture surface, it should be understood that the format of the capturing surface, e.g., beads or a filter (also referred to herein as a membrane), does not affect the ability of the methods provided herein to efficiently capture extracellular vesicles from a biological sample.

A wide range of surfaces are capable of capturing extracellular vesicles according to the methods provided herein, but not all surfaces will capture extracellular vesicles (some surfaces do not capture anything).

The present disclosure also describes a device for isolating and concentrating extracellular vesicles from biological or clinical samples using disposable plastic parts and centrifuge equipment. For example, the device comprises a column comprising a capture surface (i.e., a membrane filter), a holder that secures the capture surface between the outer frit and an inner tube, and a collection tube. The outer frit comprises a large net structure to allow passing of liquid, and is preferably at one end of the column. The inner tube holds the capture surface in place, and preferably is slightly conus-shaped. The collection tube may be commercially available, i.e., 50 ml Falcon tube. The column is preferably suitable for spinning, i.e., the size is compatible with standard centrifuge and micro-centrifuge machines.

In embodiments where the capture surface is a membrane, the device for isolating the extracellular vesicle fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that capture by filtering through a pore size smaller than the extracellular vesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapurex Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In embodiments where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). In some embodiments, the charged filter is not housed in a syringe filtration apparatus, as nucleic acid can be harder to get out of the filter in these embodiments. In some embodiments, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, $R-CH_2-SO_3-$. In some embodiments, the capture surface is a D membrane, which is a weak basic anion exchanger with diethylamine groups. $R-CH_2-NH^+(C_2H_5)_2$. In some embodiments, the capture surface is a metal chelate membrane. For example, the membrane is an IDA membrane, functionalized with minodiacetic acid $-N(CH_2COOH^-)_2$. In some embodiments, the capture surface is a microporous membrane, functionalized with aldehyde groups, $-CHO$. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In embodiments where the capture surface is charged, extracellular vesicles can be isolated with a positively charged filter.

In embodiments where the capture surface is charged, the pH during extracellular vesicle capture is a pH ≤7. In some embodiments, the pH is greater than 4 and less than or equal to 8.

In embodiments where the capture surface is a positively charged Q filter, the buffer system includes a wash buffer comprising 250 mM Bis Tris Propane, pH6.5-7.0. In embodiments where the capture surface is a positively charged Q filter, the lysis buffer is a GTC-based reagent. In embodiments where the capture surface is a positively charged Q filter, the lysis buffer is present at one volume. In embodiments where the capture surface is a positively charged Q filter, the lysis buffer is present at more than one volume.

Depending on the membrane material, the pore sizes of the membrane range from 3 μm to 20 nm. For example, in embodiments where the capture surface is a commercially available PES membrane, the membrane has a pore size of 20 nm (Exomir), 0.65 μm (Millipore) or 0.8 μm (Pall). In embodiments where the capture surface is a commercially available RC membrane, the membrane has a pore size in the range of 3-5 am (Sartorius, Pierce).

The surface charge of the capture surface can be positive, negative or neutral. In some embodiments, the capture surface is a positively charged bead or beads.

The methods provided herein include a lysis reagent. In some embodiments, the agent used for on-membrane lysis is a GTC-based reagent. In some embodiments, the lysis reagent is a high salt based buffer.

The methods provided herein include a variety of buffers including loading and wash buffers. Loading and wash buffers can be of high or low ionic strength. The salt concentration, e.g., NaCl concentration, can be from 0 to 2.4M. The buffers can include a variety of components. In some embodiments, the buffers include one or more of the following components: Tris, Bis-Tris, Bis-Tris-Propane, Imidazole, Citrate, Methyl Malonic Acid, Acetic Acid, Ethanolamine, Diethanolamine, Triethanolamine (TEA) and Sodium phosphate. In the methods provided herein, the pH of loading and wash buffers is important. Filters tend to clog when plasma samples at set to pH ≤5.5 before loading (the plasma will not spin through the column at all), and at higher pH extracellular vesicle RNA recovery is lower due to instability of the extracellular vesicles. At neutral pH, the RNA recovery from extracellular vesicles is optimal. In some embodiments, the buffer used is at 1× concentration, 2× concentration, 3× concentration, or 4× concentration. For example, the loading or binding buffer is at 2× concentration while the wash buffer is at 1× concentration.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure extracellular vesicle fraction. Detergents suitable for use include, but are not limited to, sodium dodecyl sulfate (SDS), Tween-20, Tween-80, Triton X-100, Nonidet P-40 (NP-40). Brij-35, Brij-58, octyl glucoside, octyl thioglucoside, CHAPS or CHAPSO.

In some embodiments, the capture surface, e.g., membrane, is housed within a device used for centrifugation; e.g. spin columns, or for vacuum system e.g. vacuum filter holders, or for filtration with pressure e.g. syringe filters. In some embodiments, the capture surface is housed in a spin column or vacuum system.

The isolation of extracellular vesicles from a biological sample prior to extraction of nucleic acids is advantageous for the following reasons: 1) extracting nucleic acids from extracellular vesicles provides the opportunity to selectively analyze disease or tumor-specific nucleic acids obtained by isolating disease or tumor-specific extracellular vesicles apart from other extracellular vesicles within the fluid sample; 2) nucleic acid-containing extracellular vesicles produce significantly higher yields of nucleic acid species with higher integrity as compared to the yield/integrity obtained by extracting nucleic acids directly from the fluid sample without first isolating extracellular vesicles; 3) scalability, e.g., to detect nucleic acids expressed at low levels, the sensitivity can be increased by concentrating extracellular vesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated extracellular vesicle fractions can be of a smaller volume than that of the starting sample volume, making it possible to extract nucleic acids from these fractions or pellets using small volume column filters.

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

An object of the present invention is therefore to provide a method for quick and easy isolation of nucleic acid-containing particles from biological samples such as body fluids and extraction of high quality nucleic acids from the isolated particles. The method of the invention may be suitable for adaptation and incorporation into a compact device or an semi- or fully-automated instrument for use in a laboratory or clinical setting, or in the field.

In some embodiments, the sample is not pre-processed prior to isolation and extraction of nucleic acids, e.g., DNA and/or DNA and RNA, from the biological sample.

In some embodiments, the sample is subjected to a pre-processing step prior to isolation, purification or enrichment of the extracellular vesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. Alternatively, or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 µm filter.

In some embodiments, the sample is pre-filtered to exclude particles larger than 0.8 µm. In some embodiments, the sample includes an additive such as EDTA, sodium citrate, and/or citrate-phosphate-dextrose. In some embodiments, the sample does not contain heparin, as heparin can negatively impact RT-qPCR and other nucleic acid analysis. In some embodiments, the sample is mixed with a buffer prior to purification and/or nucleic acid isolation and/or extraction. In some embodiments, the buffer is a binding buffer.

In some embodiments, one or more centrifugation steps are performed before or after contacting the biological sample with the capture surface to separate extracellular vesicles and concentrate the extracellular vesicles isolated from the biological fraction. To remove large unwanted particles, cells, and/or cell debris, the samples may be centrifuged at a low speed of about 100-500 g, for example, in some embodiments, about 250-300 g. Alternatively or in addition, the samples may be centrifuged at a higher speed. Suitable centrifugation speeds are up to about 200,000 g; for example, from about 2,000 g to less than about 200,000 g. Speeds of above about 15,000 g and less than about 200,000 g or above about 15,000 g and less than about 100,000 g or above about 15,000 g and less than about 50,000 g are used in some embodiments. Speeds of from about 18,000 g to about 40,000 g or about 30,000 g; and from about 18,000 g to about 25,000 g are more preferred. In some embodiments, a centrifugation speed of about 20,000 g. Generally, suitable times for centrifugation are from about 5 minutes to about 2 hours, for example, from about 10 minutes to about 1.5 hours, or from about 15 minutes to about 1 hour. A time of about 0.5 hours may be used. It is sometimes useful, in some embodiments, to subject the biological sample to centrifugation at about 20,000 g for about 0.5 hours. However, the above speeds and times can suitably be used in any combination (e.g., from about 18.000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., for example, about 1-5° C., e.g., about 3° C. or about 4° C.

In some embodiments, one or more filtration steps are performed before or after contacting the biological sample with the capture surface. A filter having a size in the range about 0.1 to about 1.0 µm may be employed, for example, about 0.8 µm or 0.22 µm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the extracellular vesicles. This may consist of a series of differential centrifugations. The extracellular vesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the extracellular vesicle fraction. In another embodiment, the filtration is an ultrafiltration, for example, a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, for example, in some embodiments, between 100 kDa and 1000 kDa, or for example, in some embodiments, between 100 kDa and 600 kDa, is advantageous.

In some embodiments, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are used in some embodiments. For example, such supports include, but are not limited to: SUPERDEX, 200HR (Pharmacia), TSK G6000 (TosoHaas) or SEPHACRYL® S (Pharmacia).

In some embodiments, one or more affinity chromatography steps are performed before or after contacting the biological sample with the capture surface. Some extracellular vesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008, Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of lung, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

In some embodiments, one or more control particles or one or more nucleic acid(s) may be added to the sample prior to extracellular vesicle isolation and/or nucleic acid extraction to serve as an internal control to evaluate the efficiency or quality of extracellular vesicle purification and/or nucleic acid extraction. The methods described herein provide for the efficient isolation and the control nucleic acid(s) along with the extracellular vesicle fraction. These control nucleic acid(s) include one or more nucleic acids from Q-beta bacteriophage, one or more nucleic acids from virus particles, or any other control nucleic acids (e.g., at least one control target gene) that may be naturally occurring or engineered by recombinant DNA techniques. In some embodiments, the quantity of control nucleic acid(s) is known before the addition to the sample. The control target gene can be quantified using real-time PCR analysis. Quantification of a control target gene can be used to determine the efficiency or quality of the extracellular vesicle purification or nucleic acid extraction processes.

In some embodiments, the control nucleic acid is a nucleic acid from a Q-beta bacteriophage, referred to herein as "Q-beta control nucleic acid." The Q-beta control nucleic acid used in the methods described herein may be a naturally-occurring virus control nucleic acid or may be a recombinant or engineered control nucleic acid. Q-beta is a member of the leviviridae family, characterized by a linear, single-stranded RNA genome that consists of 3 genes encoding four viral proteins: a coat protein, a maturation protein, a lysis protein, and RNA replicase. When the Q-beta particle itself is used as a control, due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. When the Q-beta particle itself is used as a control, after addition of the Q-beta particles to the biological sample, the nucleic acids from the Q-beta particle are extracted along with the nucleic acids from the biological sample using the extraction methods described herein. When a nucleic acid from Q-beta, for example, RNA from Q-beta, is used as a control, the Q-beta nucleic acid is extracted along with the nucleic acids from the biological sample using the extraction methods described herein. Detection of the Q-beta control target gene can be determined by RT-PCR analysis, for example, simultaneously with the biomarker(s) of interest A standard curve of at least 2, 3, or 4 known concentrations in 10-fold dilution of a control target gene can be used to determine copy number. The copy number detected and the quantity of Q-beta particle added or the copy number detected and the quantity of Q-beta nucleic acid, for example, Q-beta RNA, added can be compared to determine the quality of the isolation and/or extraction process.

In some embodiments, 50, 100, 150, 200, 250, 300, 350, 400, 450, 500, 1,000 or 5,000 copies of Q-beta particles or Q-beta nucleic acid, for example, Q-beta RNA, added to a bodily fluid sample. In some embodiments, 100 copies of Q-beta particles or Q-beta nucleic acid, for example, Q-beta RNA, are added to a bodily fluid sample. When the Q-beta particle itself is used as control, the copy number of Q-beta particles can be calculated based on the ability of the Q-beta bacteriophage to infect target cells. Thus, the copy number of Q-beta particles is correlated to the colony forming units of the Q-beta bacteriophage.

Optionally, control particles may be added to the sample prior to extracellular vesicle isolation or nucleic acid extraction to serve as an internal control to evaluate the efficiency or quality of extracellular vesicle purification and/or nucleic acid extraction. The methods described herein provide for the efficient isolation and the control particles along with the extracellular vesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. Quantification of a control target gene can be used to determine the efficiency or quality of the extracellular vesicle purification or nucleic acid extraction processes.

In some embodiments, the Q-beta particles are added to the urine sample prior to nucleic extraction. For example, the Q-beta particles are added to the urine sample prior to ultrafiltration and/or after the pre-filtration step.

In some embodiments, the methods and kits described herein include one or more in-process controls. In some embodiments, the in-process control is detection and analysis of a reference gene that indicates sample quality (i.e., an indicator of the quality of the biological sample, e.g., biofluid sample). In some embodiments, the in-process control is detection and analysis of a reference gene that indicates plasma quality (i.e., an indicator of the quality of the plasma sample). In some embodiments, the reference gene(s) is/are analyzed by additional qPCR.

In some embodiments, the in-process control is an in-process control for reverse transcriptase and/or PCR performance. These in-process controls include, by way of non-limiting examples, a reference RNA (also referred to herein as ref.RNA), that is spiked in after RNA isolation and prior to reverse transcription. In some embodiments, the ref.RNA is a control such as Qbeta. In some embodiments, the ref.RNA is analyzed by additional PCR.

Nucleic Acid Extraction

The present invention is directed towards the use of a capture surface for the improved isolation, purification, or enrichment of extracellular vesicles. The methods disclosed herein provide a highly enriched extracellular vesicle fraction for extraction of high quality nucleic acids from said extracellular vesicles. The nucleic acid extractions obtained by the methods described herein may be useful for various applications in which high quality nucleic acid extractions are required or preferred, such as for use in the diagnosis, prognosis, or monitoring of diseases or medical conditions.

Recent studies reveal that nucleic acids within microvesicles have a role as biomarkers. For example, WO 2009/100029 describes, among other things, the use of nucleic acids extracted from microvesicles in GBM patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al., 2008).

The quality or purity of the isolated extracellular vesicles can directly affect the quality of the extracted extracellular vesicle nucleic acids, which then directly affects the efficiency and sensitivity of biomarker assays for disease diagnosis, prognosis, and/or monitoring. Given the importance of accurate and sensitive diagnostic tests in the clinical field, methods for isolating highly enriched extracellular vesicle fractions from biological samples are needed. To address this need, described herein are methods for isolating extracellular vesicles from biological sample for the extraction of high quality nucleic acids from a biological sample. As shown herein, highly enriched extracellular vesicle fractions are isolated from biological samples by methods described herein, and wherein high quality nucleic acids subsequently extracted from the highly enriched extracellular vesicle fractions. These extracted high quality nucleic acids are useful for measuring or assessing the presence or absence of biomarkers for aiding in the diagnosis, prognosis, and/or monitoring of diseases or other medical conditions.

As used herein, the term "high quality" in reference to nucleic acid extraction means an extraction in which one is able to detect 18S and 28S rRNA, for example, in some embodiments, in a ratio of approximately 1:1 to approximately 1:2; and/or for example, in some embodiments, approximately 1:2. Ideally, high quality nucleic acid extractions obtained by the methods described herein will also have an RNA integrity number of greater than or equal to 5 for a low protein biological sample (e.g., urine), or greater than or equal to 3 for a high protein biological sample (e.g., serum), and a nucleic acid yield of greater than or equal to 50 pg/ml from a 20 ml low protein biological sample or a 1 ml high protein biological sample.

High quality RNA extractions are desirable because RNA degradation can adversely affect downstream assessment of the extracted RNA, such as in gene expression and mRNA analysis, as well as in analysis of non-coding RNA such as small RNA and microRNA. The methods described herein enable one to extract high quality nucleic acids from extracellular vesicles isolated from a biological sample so that an accurate analysis of nucleic acids within the extracellular vesicles can be performed.

Following the isolation of extracellular vesicles from a biological sample, nucleic acid may be extracted from the isolated or enriched extracellular vesicle fraction. To achieve this, in some embodiments, the extracellular vesicles may first be lysed. The lysis of extracellular vesicles and extraction of nucleic acids may be achieved with various methods known in the art, including those described in PCT Publication Nos. WO 2016/007755 and WO 2014/107571, the contents of each of which are hereby incorporated by reference in their entirety. In some embodiments, the nucleic acid extraction may be achieved using protein precipitation according to standard procedures and techniques known in the art. Such methods may also utilize a nucleic acid-binding column to capture the nucleic acids contained within the extracellular vesicles. Once bound, the nucleic acids can then be eluted using a buffer or solution suitable to disrupt the interaction between the nucleic acids and the binding column, thereby eluting the nucleic acids.

In some embodiments, the nucleic acid extraction methods also include the step of removing or mitigating adverse factors that prevent high quality nucleic acid extraction from a biological sample. Such adverse factors are heterogeneous in that different biological samples may contain various species of adverse factors. In some biological samples, factors such as excessive DNA may affect the quality of nucleic acid extractions from such samples. In other samples, factors such as excessive endogenous RNase may affect the quality of nucleic acid extractions from such samples. Many agents and methods may be used to remove these adverse factors. These methods and agents are referred to collectively herein as an "extraction enhancement operations." In some instances, the extraction enhancement operation may involve the addition of nucleic acid extraction enhancement agents to the biological sample. To remove adverse factors such as endogenous RNases, such extraction enhancement agents as defined herein may include, but are not limited to, an RNase inhibitor such as Superase-In (commercially available from Ambion Inc.) or RnaseINplus (commercially available from Promega Corp.), or other agents that function in a similar fashion; a protease (which may function as an Rnase inhibitor); DNase; a reducing agent; a decoy substrate such as a synthetic RNA and/or carrier RNA; a soluble receptor that can bind RNase; a small interfering RNA (siRNA); an RNA binding molecule, such as an anti-RNA antibody, a basic protein or a chaperone protein; an RNase denaturing substance, such as a high osmolarity solution, a detergent, or a combination thereof.

For example, the extraction enhancement operation may include the addition of an Rnase inhibitor to the biological sample, and/or to the isolated extracellular vesicle fraction, prior to extracting nucleic acid; for example, in some embodiments, the RNase inhibitor has a concentration of greater than 0.027 AU (1×) for a sample equal to or more than 1 µl in volume; alternatively, greater than or equal to 0.135 AU (5×) for a sample equal to or more than 1 µl; alternatively, greater than or equal to 0.27 AU (10×) for a sample equal to or more than 1 µl; alternatively, greater than or equal to 0.675 AU (25×) for a sample equal to or more than 1 µl; and alternatively, greater than or equal to 1.35 AU (50×) for a sample equal to or more than 1 µl; wherein the 1× concentration refers to an enzymatic condition wherein 0.027 AU or more RNase inhibitor is used to treat extracellular vesicles isolated from 1 µl or more bodily fluid, the 5× concentration refers to an enzymatic condition wherein 0.135 AU or more RNase inhibitor is used to treat extracellular vesicles isolated from 1 µl or more bodily fluid, the 10× protease concentration refers to an enzymatic condition wherein 0.27 AU or more RNase inhibitor is used to treat particles isolated from 1 µl or more bodily fluid, the 25× concentration refers to an enzymatic condition wherein 0.675 AU or more RNase inhibitor is used to treat extracellular vesicles isolated from 1 µl or more bodily fluid, and the 50× protease concentration refers to an enzymatic condition wherein 1.35 AU or more RNase inhibitor is used to treat particles isolated from 1 µl or more bodily fluid. In some embodiments, the RNase inhibitor is a protease, in which case, 1 AU is the protease activity that releases folin-positive amino acids and peptides corresponding to 1 µmol tyrosine per minute.

These enhancement agents may exert their functions in various ways, e.g., through inhibiting RNase activity (e.g., RNase inhibitors), through a ubiquitous degradation of proteins (e.g., proteases), or through a chaperone protein (e.g., an RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

In some embodiments, the quantification of 18S and 28S rRNAs extracted can be used to determine the quality of the nucleic acid extraction.

Detection of Nucleic Acid Biomarkers

In some embodiments, the extracted nucleic acid comprises DNA and/or DNA and RNA. In embodiments where the extracted nucleic acid comprises DNA and RNA, the RNA is reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct values are inversely proportional to the amount of target nucleic acid, or control nucleic acid, in the sample (i.e., the lower the Ct value, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

In some embodiments, one or more biomarkers can be or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated extracellular vesicles, whether wild type or variants, are identified with methods known in the art.

The present invention also includes various uses of methods of isolating extracellular vesicles and sequencing nucleic acids from a biological sample for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

In some embodiments, it may be beneficial or otherwise desirable to amplify the nucleic acid of the extracellular vesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a genetic or expression profile.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006), or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extract nucleic acids are analyzed directly (e.g., through next-generation sequencing).

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGEXFischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations/modifications thereof. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of a biomarker or combination of biomarkers in a nucleic acid extraction from isolated particles, according to the methods disclosed herein, aid diagnosis of a disease or other medical condition in the subject.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject.

Many biomarkers have also been found to influence the effectiveness of treatment in a particular patient. Therefore, the detection of the presence or absence of such biomarkers in a nucleic acid extraction from isolated particles, according to the methods disclosed herein, may aid in evaluating the efficacy of a given treatment in a given patient. The identification of these biomarkers in nucleic acids extracted from isolated particles from a biological sample from a patient may guide the selection of treatment for the patient.

In certain embodiments of the foregoing aspects of the invention, the disease or other medical condition is a neoplastic disease or condition (e.g., cancer or cell proliferative disorder).

In some embodiments, the extracted nucleic acids, e.g., exosomal RNA, also referred to herein as "exoRNA," are further analyzed based on detection of a biomarker or a combination of biomarkers. In some embodiments, the further analysis is performed using machine-learning based modeling, data mining methods, and/or statistical analysis. In some embodiments, the data is analyzed to identify or predict disease outcome of the patient. In some embodiments, the data is analyzed to stratify the patient within a patient population. In some embodiments, the data is analyzed to identify or predict whether the patient is resistant to treatment. In some embodiments, the data is used to measure progression-free survival progress of the subject.

In some embodiments, the data is analyzed to select a treatment option for the subject when a biomarker or combination of biomarkers is detected. In some embodiments, the treatment option is treatment with a combination of therapies.

Sequencing Techniques

In some embodiments, "next-generation" sequencing (NGS) or high-throughput sequencing experiments are performed according to the methods of the invention. These sequencing techniques allow for the identification of nucleic acids present in low or high abundance in a sample, or which are otherwise not detected by more conventional hybridization methods. NGS typically incorporate the addition of nucleotides followed by washing steps.

Commercially available kits for total RNA SEQUENCING which preserves the strand information, meant for mammalian RNA and very low input RNA are useful in this regard, and include, without limitation, Clontech: SMARTer stranded total RNASeq kit; Clontech: SMARTSeq v4 ultra low input RNASeq kit; Illumina: Truseq stranded total RNA library prep kit; Kapa Biosystems: Kapa stranded RNASeq library preparation kit; New England Biolabs: NEBNext ultra directional library prep kit; Nugen: Ovation Solo RNASeq kit; and Nugen: Nugen Ovation RNASeq system v2.

EXAMPLES

While the Examples provided herein use a variety of membranes and devices used for centrifugation and/or filtration purposes, it is to be understood that these methods can be used with any capture surface and/or housing device that allows for the efficient capture of extracellular vesicles and release of the nucleic acids, particularly RNA, contained therein.

Example 1

Sample Isolation

Samples are generally obtained from commercial sources and isolated by EXO50 and/or EXO52 methods, as described in e.g., WO 2014/107571 and WO 2016/007755.

Long RNASea Workflow Method 1:

After sample isolation, samples are treated with DNase I enzyme and/or modified DNase I enzymes following manufacture's guidelines: generally by incubating from about 10 minutes to about 2 hours, such as about 10 minutes to about 60 minutes, and at a temperature of from about 30° C. to about 40° C., such as about 35° C. to about 37° C.

Following DNase treatment, exogenous synthetic RNA spike-ins are added to the sample at a dilution adjusted according to the sample. The synthetic spike-ins may be added to the sample either prior to DNase treatment or post DNase treatment. Subsequently, the sample is subjected either to RNA fragmentation using commercial reagents/protocol, or sample is left unfragmented.

Then the sample is subjected to first strand cDNA synthesis (reverse transcription) using commercially available reagents, following manufacture's guidelines.

Then Illumina based NGS adapters are added to the cDNA using PCR based techniques and commercially available reagents according to manufacturer's guidelines.

Following PCR based addition of NGS adapters, sample is subjected to one or two rounds of paramagnetic bead based library clean up using commercially available reagents in general following manufacture's guidelines.

Following AMPure cleanup, samples are subjected to ribodepletion using commercially available reagents and protocol.

Then the sample is subjected to multiple cycles of PCR amplification, using commercially available reagents and protocol. PCR based amplification cycles may range from 10 to 30 cycles.

Following PCR amplification, sample is subjected to one or two rounds of paramagnetic bead based library clean up using commercially available reagents and protocols.

At this stage, the final NGS library and the sample are subjected to standard NGS QC measurements including BioAnalyzer (fragment size analysis and concentration) and Qubit (concentration). Samples are diluted to 1-4 nM concentration and then pooled prior to preparation for sequencing. Standard sequencing preparation includes sample denaturation and dilution to the pM concentration used for clustering on the sequencing instrument.

Long RNASeq Workflow Method 3:

After isolation, samples are treated with DNase I enzymes generally following manufacture's guidelines, generally by incubating from about 10 minutes to about 2 hours, such as about 10 minutes to about 60 minutes, or about 30 minutes, and at a temperature of from about 30° C. to about 40° C., such as about 35° C. to about 37° C.

After DNase treatment, exogenous synthetic RNA spike-ins are added to the sample at a dilution adjusted according to the sample.

Next, the sample is subjected to another round of DNase treatment and primer annealing using commercially available reagents and protocols.

Then the sample is subjected to first strand cDNA synthesis (reverse transcription) using commercially available reagents following manufacture's guidelines.

The sample is then subjected to a series of cDNA processing steps using commercially available NGS reagents.

Then the sample is subjected to second strand cDNA synthesis (reverse transcription), End Repair, and Adapter ligation using commercially available reagents and guidelines. Following adapter ligation, sample is subjected to one or more rounds of paramagnetic bead based library clean up using commercially available reagents. The standard protocol has been modified to change the beads hydration time and elution volumes for our workflow, as set forth in the Examples.

Next, quantitative PCR (qPCR) is performed to determine optimal amplification cycles for the samples being tested using commercially available reagents.

Then the sample is subjected to PCR amplification based on the number of cycles identified in the previous step using commercially available reagents and protocol.

Following PCR amplification, sample is subjected to one or two rounds of paramagnetic bead based library clean up using commercially available reagents and protocol although standard kit protocol has been modified to additionally provide a bead hydration step for our workflow.

Next the sample is subjected to standard BioAnalyzer or Qubit analysis to determine sample concentration. Up to 10 ng of library is taken forward to the next step of the workflow.

Samples are then subjected to ribodepletion using commercially available reagents and protocol. The standard kit protocol has been modified for our workflow by adding an additional cycle of primer annealing.

Then the sample is subjected to a second round of PCR amplification, by completing multiple cycles of PCR amplification using commercially available reagents and protocol.

Following PCR amplification, sample is subjected to one or two rounds of paramagnetic bead based library clean up using commercially available reagents and protocol. The protocol has been modified to change the hydration time for our workflow, as detailed in the Examples.

At this stage, we now have final NGS library and the sample is subjected to standard NGS QC measurements including BioAnalyzer (fragment size analysis and concentration) and Qubit (concentration). Samples are diluted to 1-4 nM concentration and then pooled prior to preparation for sequencing. Standard sequencing preparation includes sample denaturation and dilution to the pM concentration used for clustering on the sequencing instrument.

Enrichment Workflow

RNA, DNA, or RNA and DNA combined are subjected to the workflow below. The sample is treated with DNase I using commercially available reagents and guidelines or left untreated.

Then, the sample is subjected to fragmentation or left unfragmented. First strand cDNA synthesis (reverse transcription) is performed on the samples, and where necessary, second strand cDNA synthesis (i.e. DNA polymerase reaction) is performed on the sample after first strand cDNA synthesis.

The sample is subjected to End Repair and Adapter ligation following commercially available reagents and guidelines. Following adapter ligation, the sample is subjected to a round of paramagnetic bead based library clean up using commercially available reagents and guidelines.

The sample is subjected to first PCR amplification according to the commercially available reagents and guidelines. Following PCR the sample is subjected to hybridization-based target enrichment and/or the final NGS library generated from Method 1 or Method 3 (RNA, DNA, or RNA and DNA) is subjected to hybridization-based target enrichment. Probes are biotinylated with specific sequences with sizes of 60 bp, 80 bp, or 120 bp. The tiling density or overlap of probes at sequence specific sites can be 1×, 2×, 3×, 4×, and more.

Probes are hybridized to specific sequences of interest in the sample using commercially available reagents and guidelines. Following hybridization, the sample is subjected to streptavidin conjugated paramagnetic beads to capture specific sequences and remove unwanted sequences. Cleaning of unwanted sequences, buffers, and enzymes are removed by washing, while specific sequences of interested in the sample are bound to streptavidin conjugated paramagnetic beads.

Hybridization of specific sequences and capture by streptavidin conjugated paramagnetic beads are performed once or multiple times, with a hybridization time ranging from about two to about 24 hours.

Following hybridization, the sequence specific captured sample is subjected to second PCR amplification according to the manufacturer's guidelines, but with increased amplification cycles to improve yield.

In some embodiments, the sample is subjected to one clean-up round by paramagnetic bead based library or using a filter spin column. The sample is eluted in a lower volume of elution buffer to increase final concentration (i.e. ng/ul, nM).

At this stage, we now have final enriched NGS library and the sample is subjected to standard NGS QC measurements including BioAnalyzer (fragment size analysis and concentration) and Qubit (concentration). Samples are diluted to 1-4 nM concentration and then pooled prior preparation for sequencing. Standard sequencing preparation includes sample denaturation and dilution to the pM concentration used for clustering on the sequencing instrument.

Example 2

We have developed a novel platform specifically designed to include both short and long RNA transcripts from exosomes into the RNA sequencing workflow. Using ExoLution or ExoLution Plus available from Exosome Diagnostics and starting with human plasma, we isolated and subjected the high quality total exosomal RNA obtained to our Long RNASeq Workflow Method 1.

Briefly, the workflow starts with exosome RNA isolation and is then followed by DNase treatment for applications where DNA could interfere in the analysis. Sometimes a spike-in of synthetic RNA standard is done, either before or after the DNase step as a quality control metric.

RNA is reverse transcribed using mixed oligos and using a reverse transcriptase with a template switching activity. This is followed by addition of DNA oligo adapters with or without bar-codes using PCR. The cDNA is cleaned up from smaller oligos using paramagnetic beads. Ribosomal sequences can sometimes affect the detection of low abundant transcripts and can therefore be selectively removed using a ribosomal depletion step. After cleavage or removal of ribosomal sequences, the uncleaved library molecules are enriched by PCR. This is followed by another cleanup using paramagnetic beads. The libraries can then be quantified and subjected to sequencing.

The objective of the experiment is to develop a stranded, total long RNASeq platform optimal for plasma exosomes.

Sample: 2 mL, normal human plasma, pool of 48 individuals, gender balanced. Synthetic spike-ins are added to the samples as controls for sensitivity, technical reproducibility and stranded-ness.

Identification and optimization variables/combination of variables suitable for exosomal RNASeq: DNase treatment, RNA/cDNA fragmentation, amplification, ribosomal RNA depletion.

Figure 1:
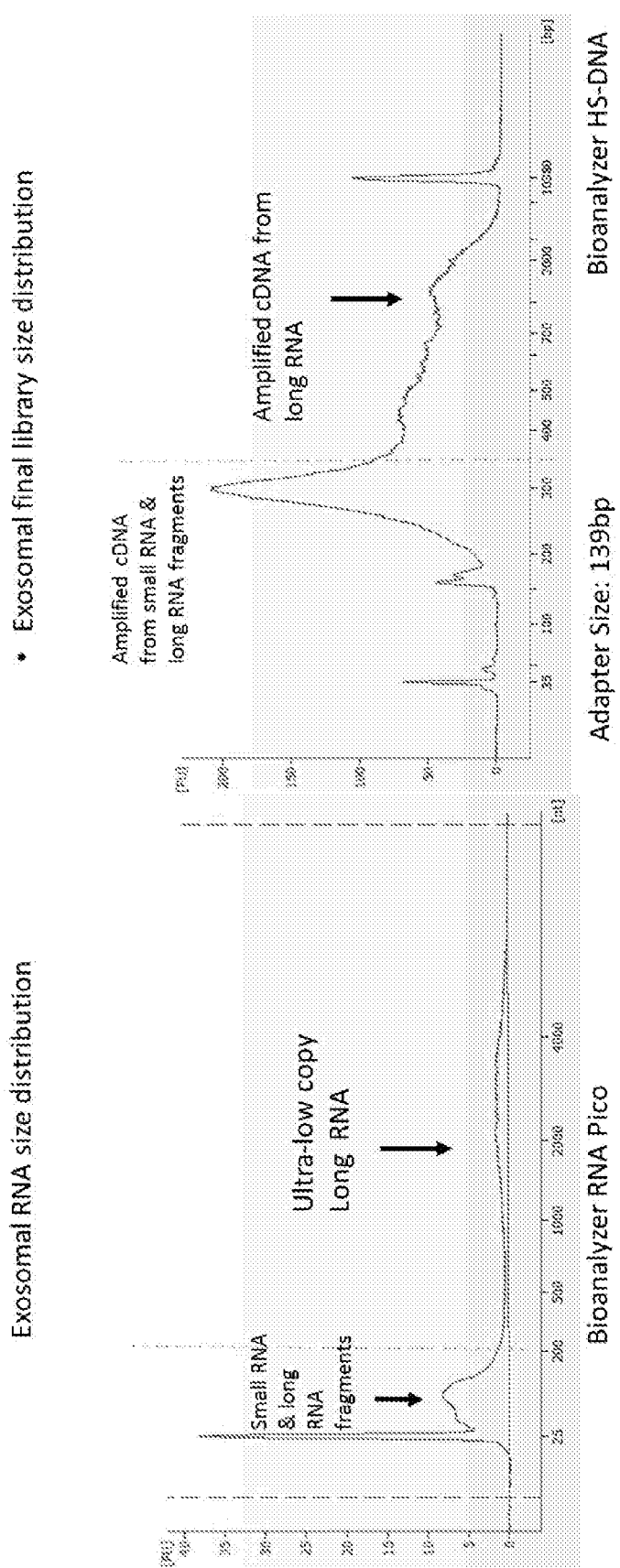
FIG. 1 is a series of bioanalyzer plots showing the RNA profiles resulting from amplification and incorporation of long RNA transcripts in RNASeq libraries.

The figures demonstrate the surprising results of the methods. In particular, FIG. 1 provides bioanalyzer scans showing the resulting amplification and incorporation of long RNA transcripts in RNASeq libraries, including exosomal RNA size distribution and exosomal final library size distribution. Amplified cDNA is seen from both small RNA and long RNA fragments.

Figure 2:
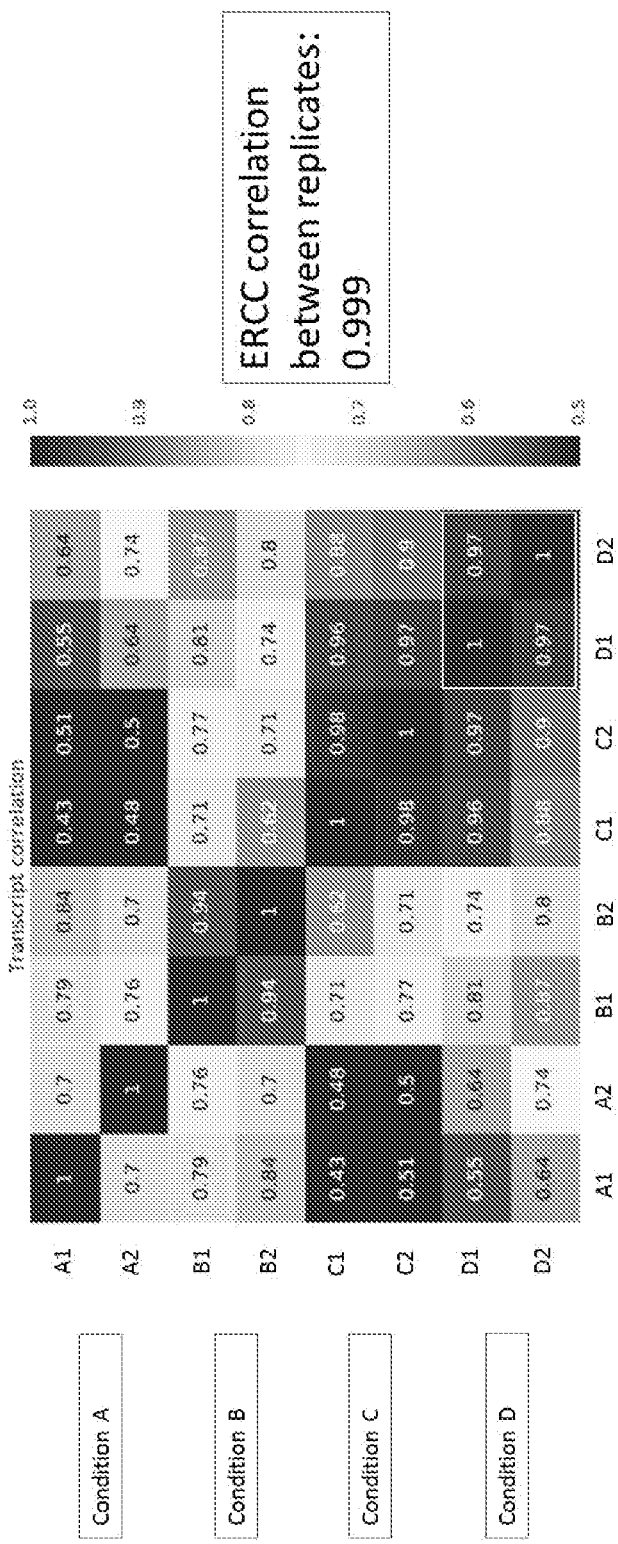
FIG. 2 is a plot showing the transcript correlation of various conditions. Use of synthetic spike-ins shows a correlation between replicates of 0.999, demonstrating the excellent correlation and reproducibility between library replicates.
Figure 3:
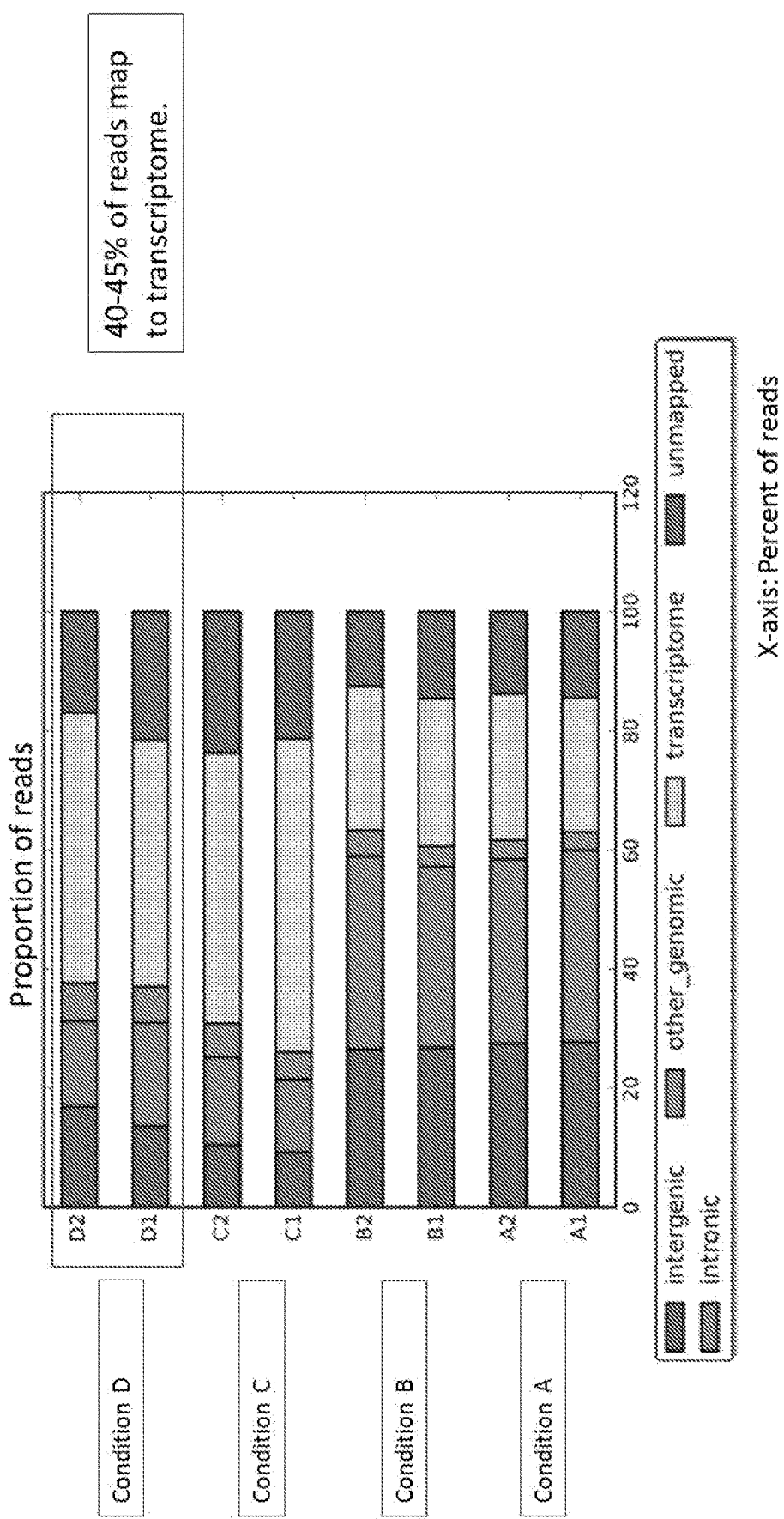
FIG. 3 illustrates the proportion of reads broken out as (left to right) intergenic, intronic, other genomic, transcriptome and unmapped, where the x-axis provides percent of reads.
Figure 4:
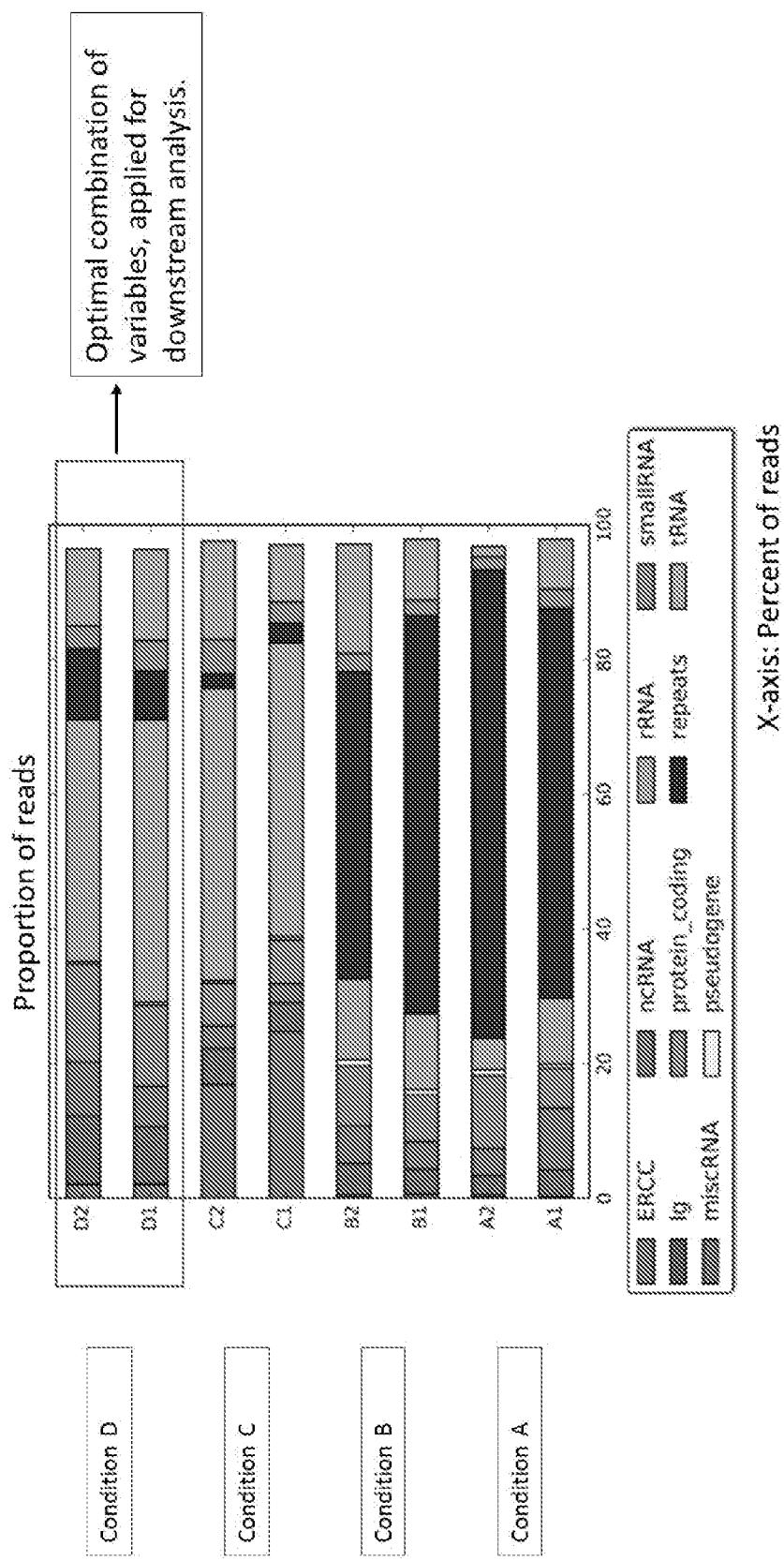
FIG. 4 also illustrates the proportion of reads broken out as (left to right) ERCC, Ig, miscRNA, ncRNA, protein coding genes, pseudogene, rRNA, repeats, smallRNA and tRNA, where the x-axis provides percent of reads.

FIG. 2 shows the excellent correlation and reproducibility between library replicates according to the method. By identifying appropriate conditions for plasma exosomal RNA, we improved the reproducibility between library replicates from 0.7 to 0.97. The technical reproducibility between replicates as determined by correlation of exogenous RNA spike-ins is 0.999. 97% to 99% of the transcripts retained the correct strand information. FIG. 3 shows that optimization of variables increases the proportion of reads map to transcriptome. In particular, modifying these parameters enables 40-45% of reads map to transcriptome. Similarly, FIG. 4 shows that optimization of variables minimizes repeats reads and increases protein coding reads.

Figure 5:
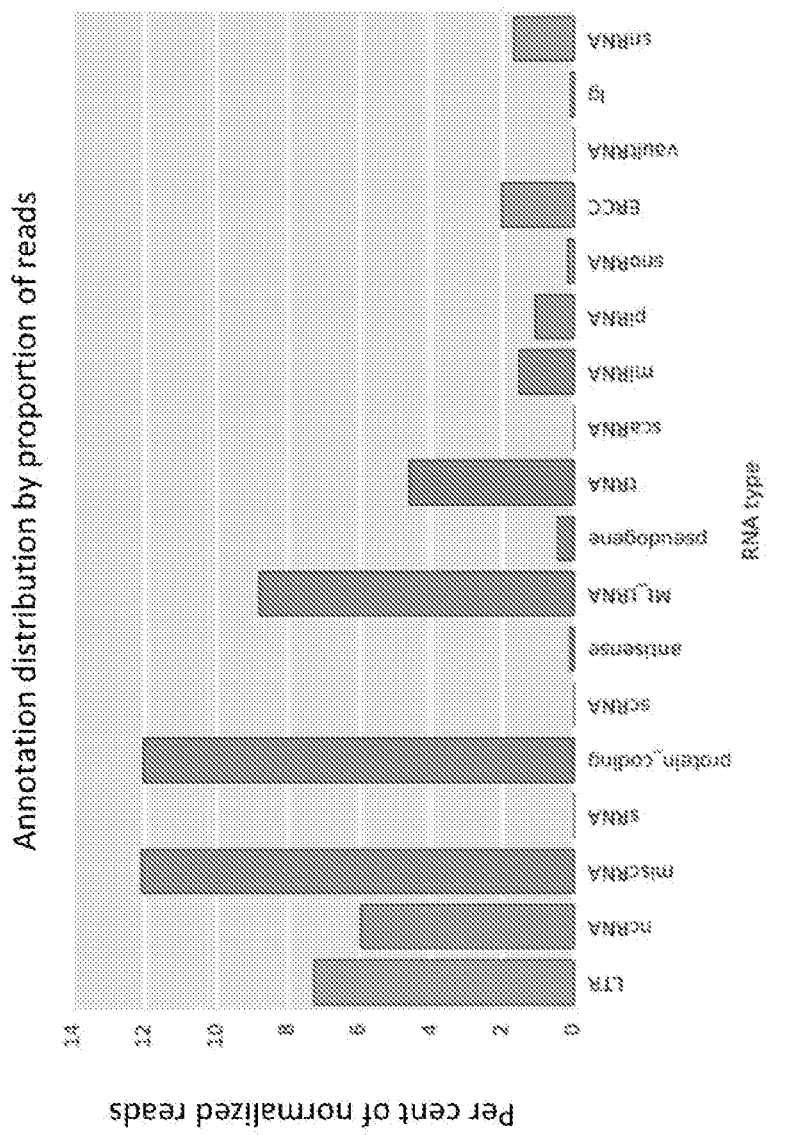
FIG. 5 is a graph plotting the annotation distribution by proportion of reads, not including ribosomal RNA, where the y-axis indicates percent of reads and the x-axis indicates RNA type.

FIG. 5 shows the wide diversity of RNA in plasma exosomes by RNA type (but excluding ribosomal RNA).

Figure 6:
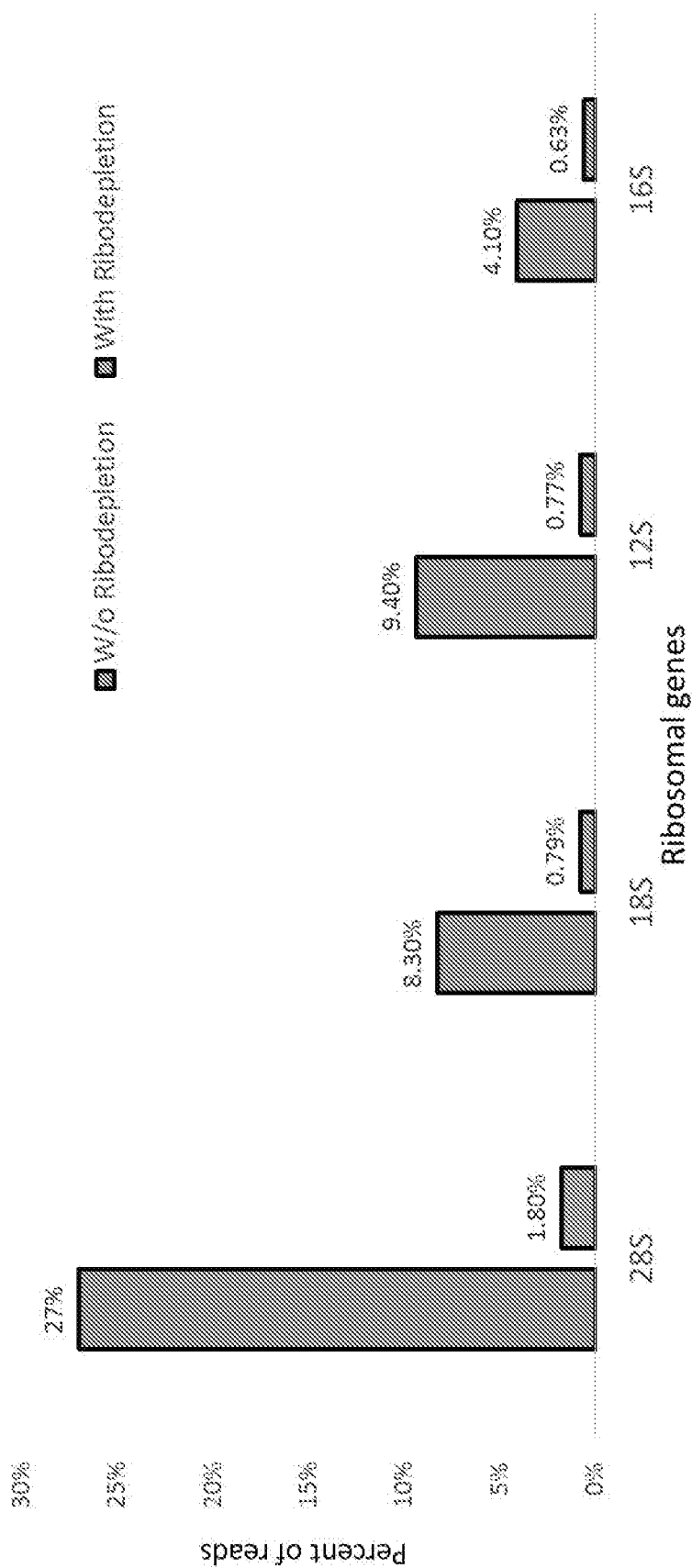
FIG. 6 is a graph plotting ribosomal genes 28S, 18S, 12S and 16S as percent of reads both without (left) and with (right) ribodepletion.

FIG. 6 shows the highly efficient depletion of ribosomal RNAs both without (left) and with (right) ribodepletion for 28S, 18S, 12S and 16S ribosomal genes.

Figure 7:
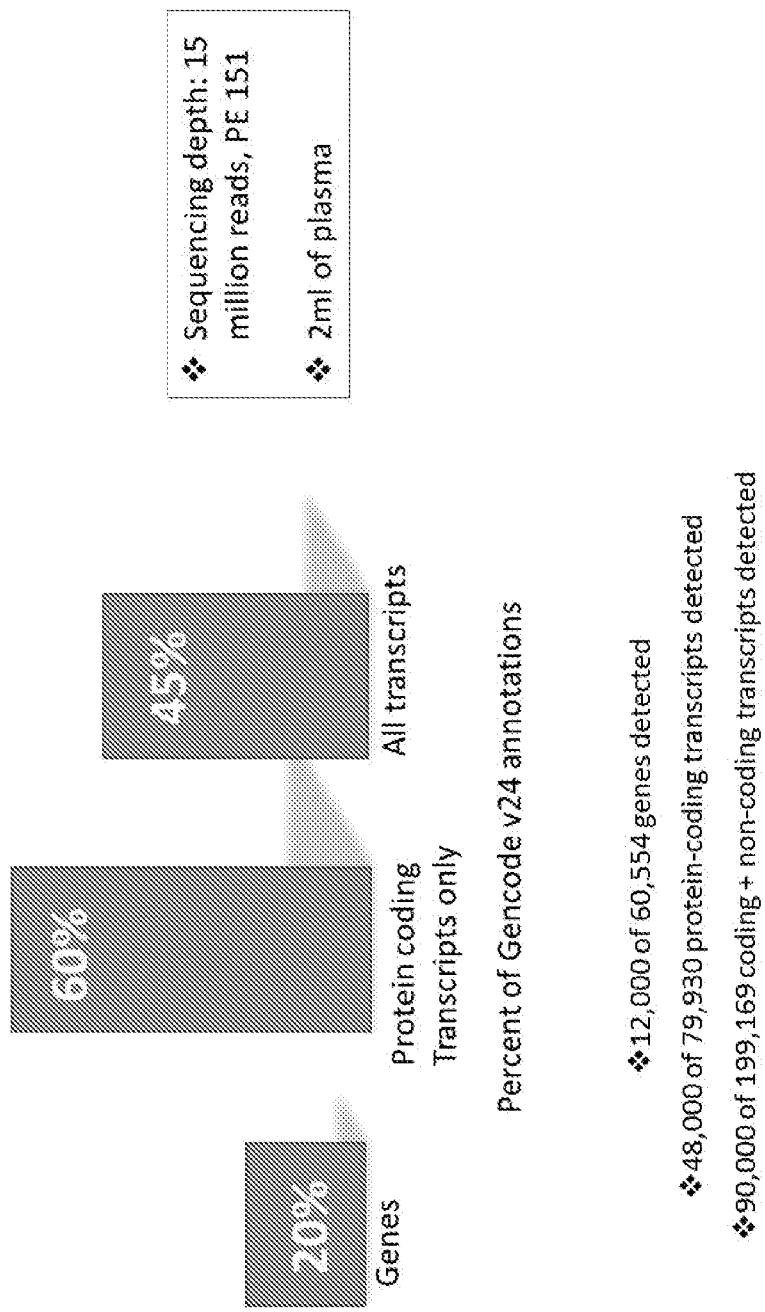
FIG. 7 illustrates the percent of Gencode v24 annotations comparing genes, protein coding transcripts only, and all transcripts.

FIG. 7 shows transcriptome coverage of plasma exosomes.

Figure 8:
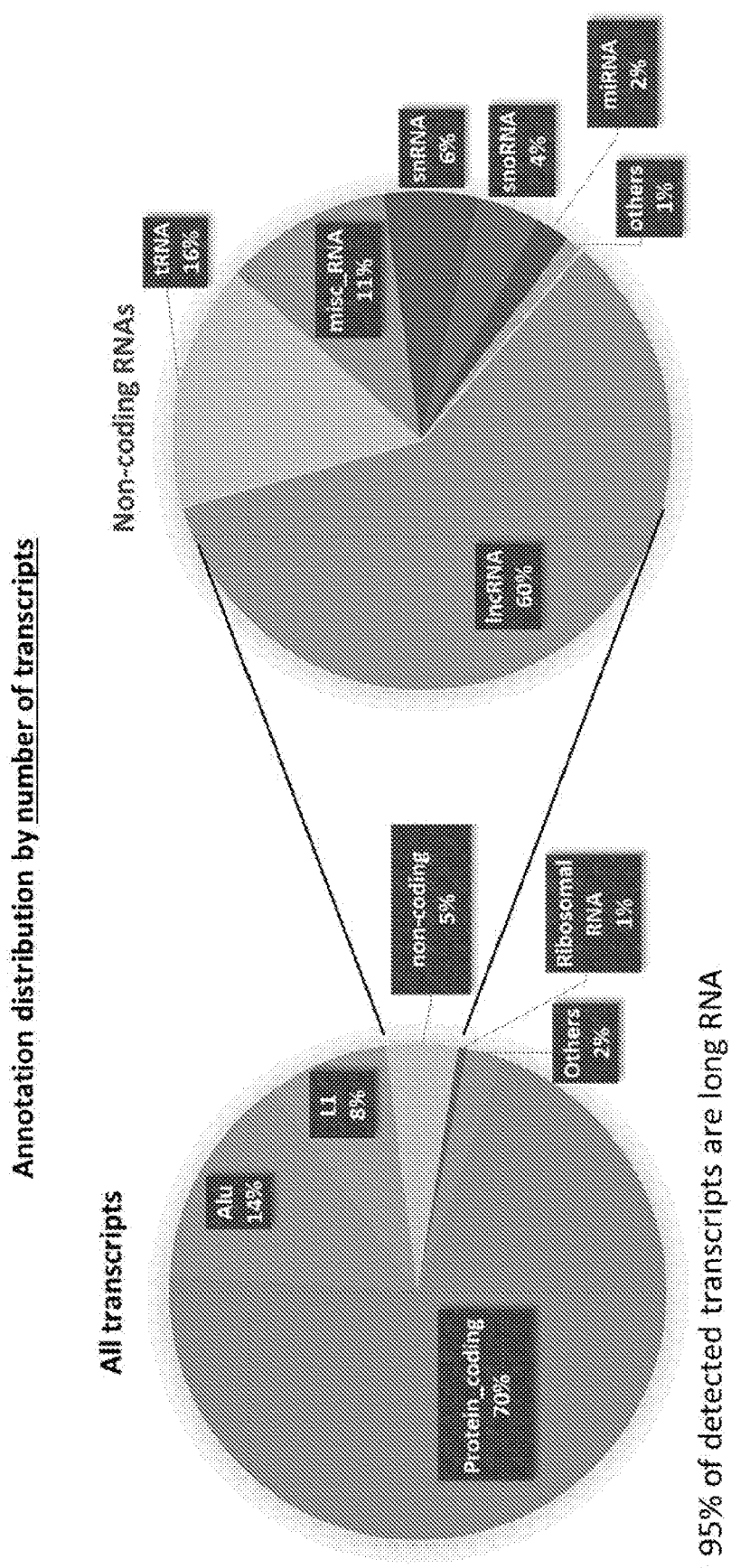
FIG. 8 plots the annotation distribution by number of transcripts for all transcripts (left) as well as expanding the non-coding RNAs (right).

FIG. 8 shows diversity of plasma exosomal RNA cargo.

Figure 9:
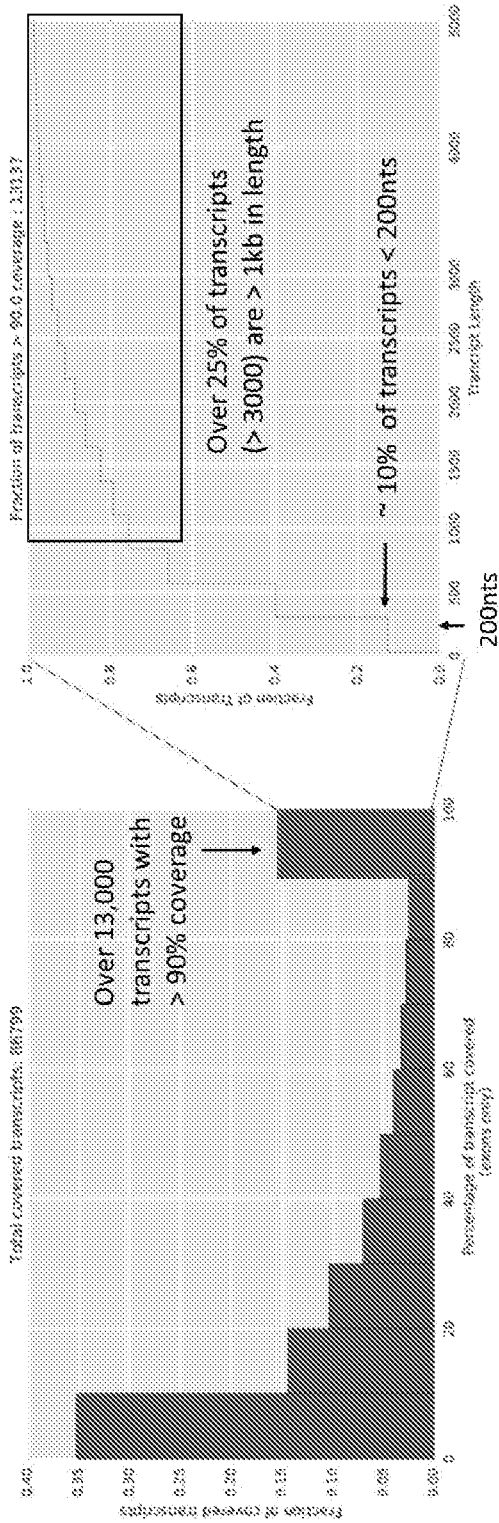
FIG. 9. is a graph plotting the 86,799 total covered transcripts as percentage of transcript covered (exons only) on the x-axis and fraction of covered transcripts on the y-axis.

FIG. 9. shows the abundance of long RNAs with full transcript coverage in exosomes and bimodal distribution of transcript coverage in exosomes.

Figure 10:
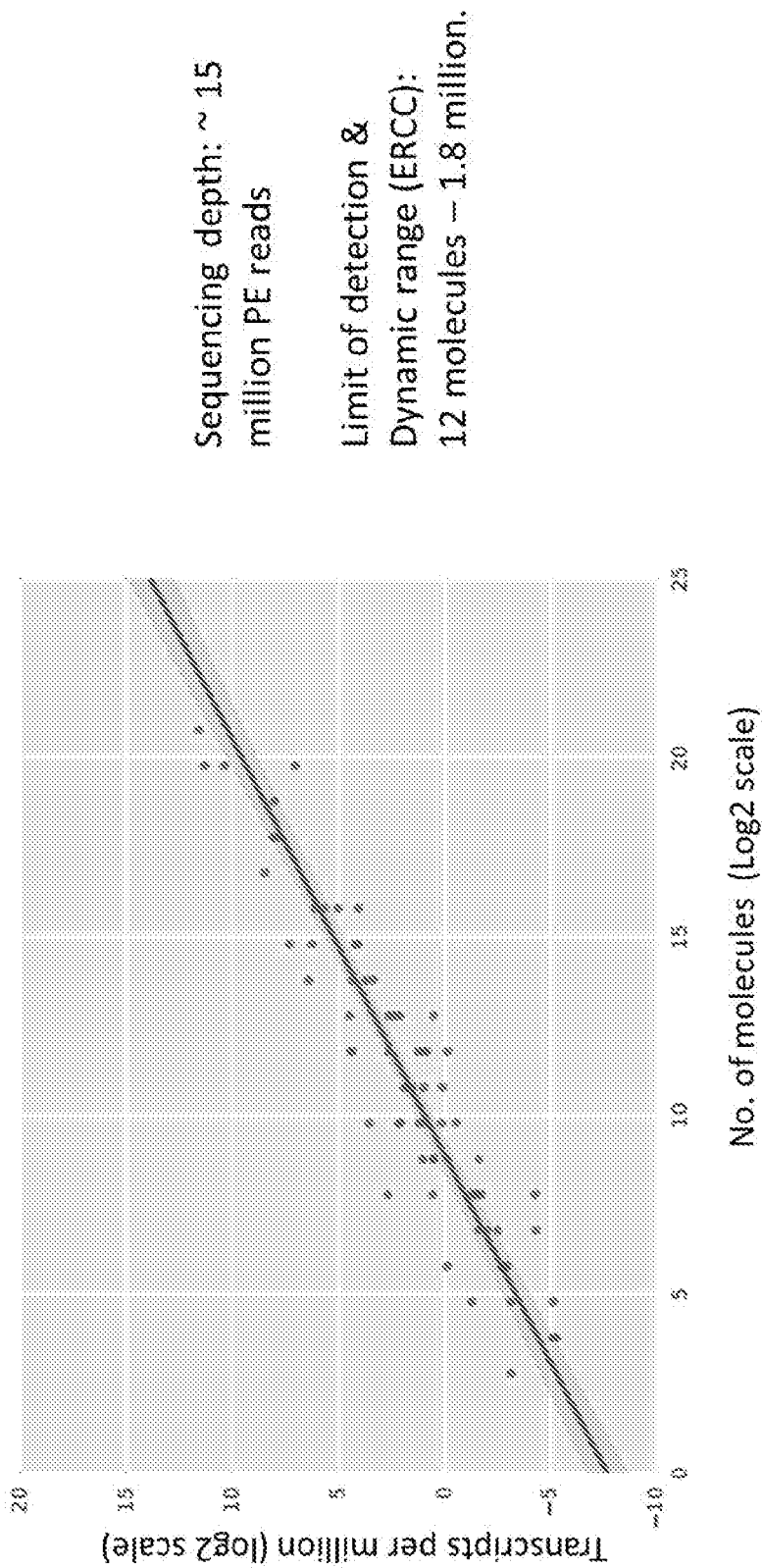
FIG. 10 is a graph plotting the number of molecules in log 2 scale on the x-axis versus transcripts per million also on the log 2 scale on the y-axis.

FIG. 10 shows that the methods provide a highly sensitive detection of molecules in exosomes.

Figure 12:
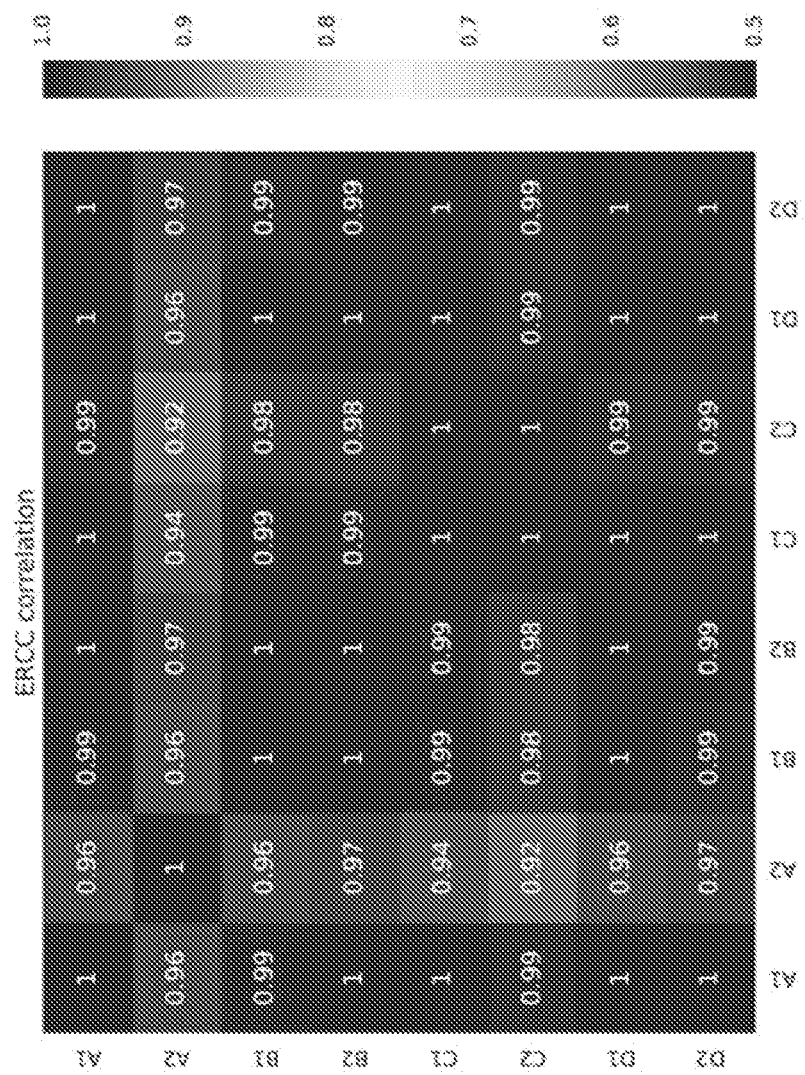
FIG. 12 is a plot demonstrating ERCC correlation of various examined conditions according to the improved workflow provided herein.
Figure 13:
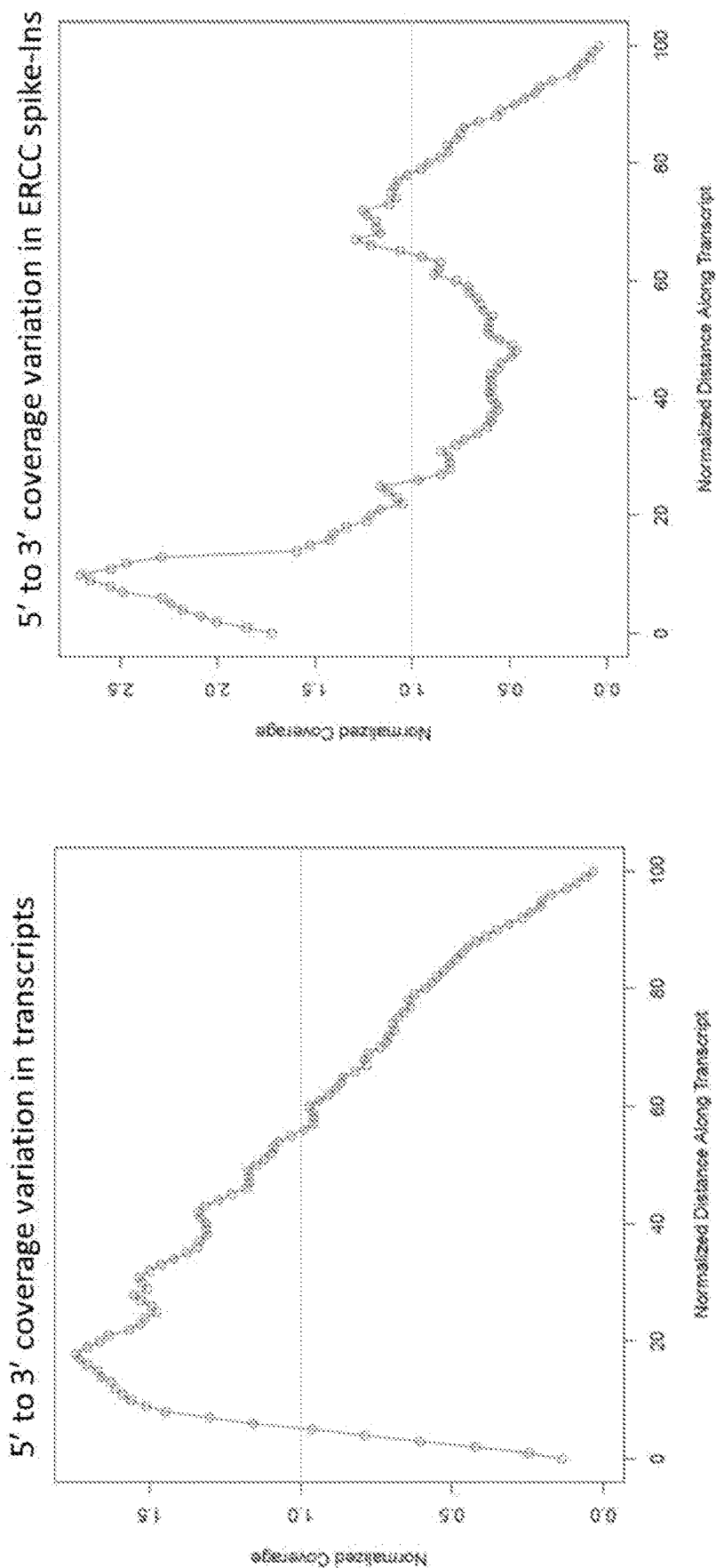
FIG. 13 is a plot of 5' to 3' coverage variation in transcripts (left) and 5' to 3' coverage variation in ERCC spike-ins (right), where the x-axis is normalized distance along transcript and the y-axis is normalized coverage.
Figure 14:
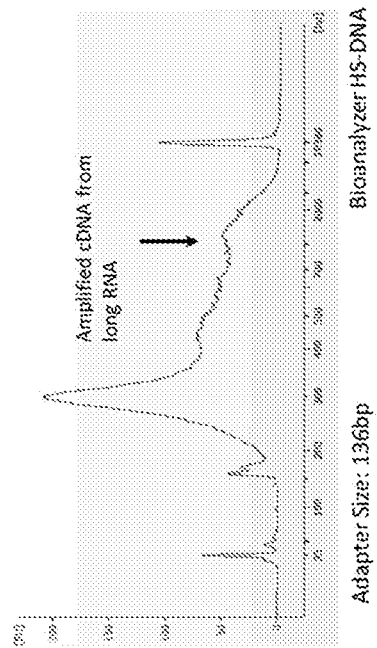
FIG. 14 is a bioanalyzer plot providing plasma exosomal final library size distribution.
Figure 15:
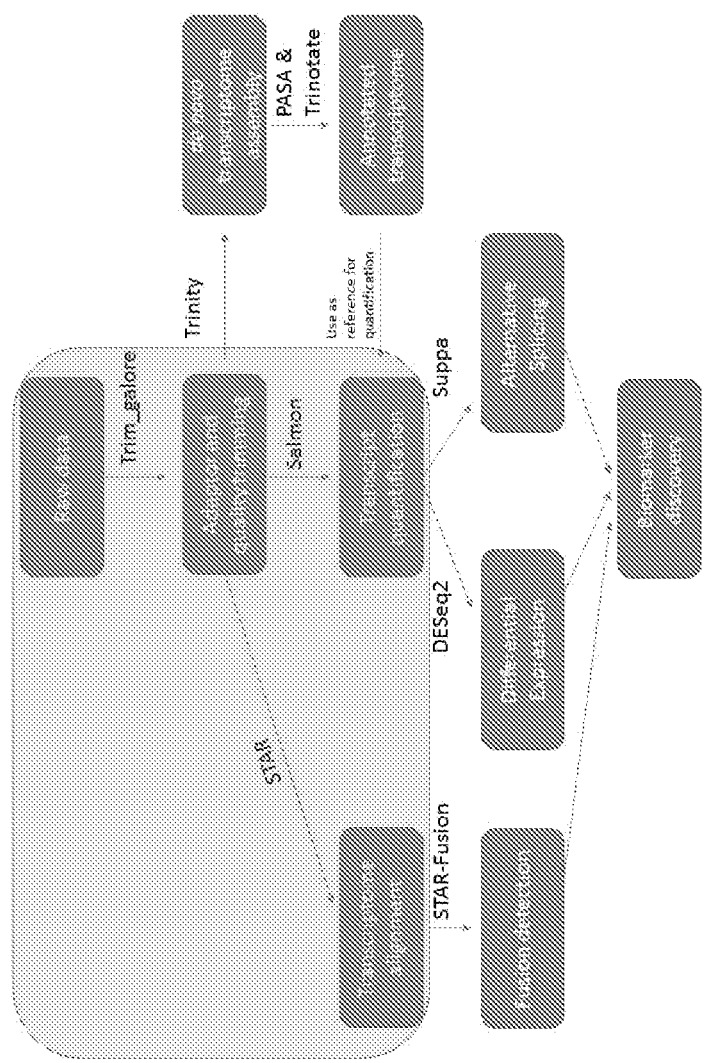
FIG. 15 is a schematic of an exemplary algorithm implemented according to the improved workflow provided herein.

Additional data generated according to the method is provided in FIGS. 11-15. FIG. 12 shows the excellent correlation of spike-ins between library replicates, while FIG. 13 demonstrates that 5' end of transcripts has higher coverage. Amplification and incorporation of long RNA transcripts in RNASeq libraries are provided as a plasma exosomal final library size distribution in FIG. 14

In summary, the method provides a novel approach for long RNASeq on exosomes. It demonstrates excellent reproducibility of detection of RNA transcripts (R>0.97), highly sensitive detection of transcripts (LOD (@15M reads=12 molecules), and highly efficient depletion of ribosomal transcripts. In addition, a wide diversity of protein coding and long non-coding RNAs are detected in exosomes according to the method. The method identifies an abundance of long transcripts with full coverage in exosomes.

Example 3

We have developed a novel platform specifically designed to include both short and long RNA transcripts from exosomes into a sequencing workflow. We have further extended these workflows to also process DNA, either alone or in mixture with RNA. We have further extended these workflows to specifically enrich the samples for targets of interest enabling deeper sequence coverage. Using ExoLution™, ExoLution HT™, UPrep™, ExoEasy™, ExoRNeasy™, or ExoLution Plus™, available from Exosome Diagnostics. and starting with human plasma, we isolated and subjected the high quality total exosomal nucleic acids obtained to our Long RNASeq Workflow Method 1 and/or Method 3.

The sequencing workflow described begins after nucleic acids have been isolated from a biofluid (FIG. 16). The volume of the biofluid serving as input for the sequencing workflow can be as low as ≥0.5 ml with no upper limit (FIG. 16). The nucleic acids can originate from exosomes and/or other cell free sources.

An aliquot of the sample can be taken to a hybridization-based enrichment process (refer to FIGS. 17-19). This process utilizes hybridization of nucleotide probes complementary to genome sequence regions of interest contained within the sample followed by a series of washes utilizing buffers that select for the sequence of interest, while washing away unwanted material. Probe-sequence hybrids can be selected for utilizing, but not limited to, streptavidin-biotin chemistries. The process can be used to enrich any portion or mixture of genomic sequence including but not limited to exonic regions and intronic regions, which can cover the full gene coding region or specific hotspot location within the gene. Hybridization probe panels can be used to enrich any number of target sequences from small numbers of targets (1 to 20) to many targets (>1,000) including, but not limited to, the total protein coding transcriptome with ~20,000 genes (see FIG. 19), large panels targeting broad disease or disease related pathways with >1,000 genes (see FIGS. 17-18), and moderate panels targeted focuses diseases or disease related pathways with 50-500 genes (e.g. solid tumor).

FIG. 17 demonstrates sample enrichment using a Pan Cancer panel. Samples were subjected to library preparation followed by enrichment for a panel of 1,387 targets implicated in cancer. Samples containing only RNA or a mixture of RNA and cfDNA from liquid biopsy were investigated. Commercially available RNA (UHR) was included as a control sample. FIG. 17A shows mapping metrics for the libraries illustrates the extremely high percentage of on target reads produced. FIG. 17B shows base coverage metrics shows that the majority of the nucleotides in the panel are covered >1× across all three samples. FIG. 17C plots the number of reads mapped per target illustrates the ability to process samples containing RNA only and RNA+cfDNA, as well as a gain in read counts when both RNA and cfDNA are analyzed in the same sample.

FIG. 18 demonstrates enrichment using a Pan Cancer capture panel. Samples were subjected to library preparation followed by enrichment for a panel of 1,387 targets implicated in cancer. Samples containing only cfDNA or a mixture of RNA and cfDNA from liquid biopsy were investigated. FIG. 18A shows mapping metrics for the libraries illustrates the extremely high percentage of on target reads produced. FIG. 18B shows base coverage metrics shows that when the same amount of starting plasma is used, cfDNA+RNA provides superior coverage of the targets compared to cfDNA alone. FIG. 17C plots the number of reads mapped per target illustrates the ability to process samples containing cfDNA only and RNA+cfDNA, as well as a gain in depth of coverage when RNA contribution is included with the cfDNA.

FIG. 19 demonstrates enrichment using a Whole Exome capture panel. Samples were subjected to library preparation followed by enrichment for a panel of ~20,000 targets representing the total protein coding transcriptome. Samples containing only cfDNA or a mixture of RNA and cfDNA from liquid biopsy were investigated. Commercially available RNA (UHR) was included as a control sample. FIG. 19A shows mapping metrics for the libraries illustrates the extremely high percentage of on target reads produced. FIG. 19B demonstrates base coverage metrics are shown. FIG. 19C shows the number of reads mapped per target and illustrates the ability to process samples containing cfDNA only and RNA+cfDNA.

Example 4

In cases where the samples have not been enriched, the total sample will be sequenced (FIGS. 20-22).

FIG. 20 demonstrates two independent RNAseq library preparation workflows that have been optimized for exosomal liquid biopsy. To minimize variability, replicate RNA extractions were isolated from a control plasma pool. Replicates (6 per method) were then processed using one of the two optimized workflows. Samples were not subjected to ribosomal depletion. All samples were subjected to deep sequencing and were downsampled to normalize read counts for analysis. FIG. 20A shows the highly reproducible detection of transcripts between library replicates. FIG. 20B shows that the proportion of reads that map to the transcriptome illustrate high on target metrics. FIG. 20C shows the proportion of reads per biotype.

When total sample is being analyzed, ribosomal sequence (cDNA, RNA, dsDNA or cfDNA) can sometimes affect the detection of low abundant transcripts, in which case it is desirable to remove or deplete the sample of ribosomal sequences (see FIG. 21). The selective removal of ribosomal sequences can be accomplished at level of RNA sequence, cDNA level or at the dsDNA (library) level. Ribosomal sequence specific depletion can be accomplished using enzymatic reagents similar but not limited to RNase H or restriction enzyme digest. Depletion can also be achieved utilizing hybridization-based biotinylated probe enrichment and streptavidin conjugated paramagnetic beads to specifically capture and remove ribosomal sequences.

Figure 21B:
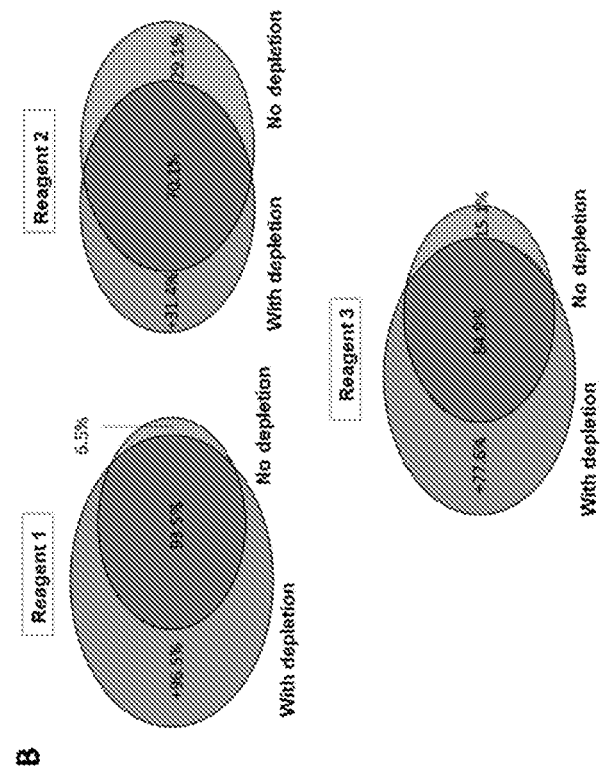
FIG. 21 demonstrates various ribosomal RNA depletion approaches.
Figure 21A:
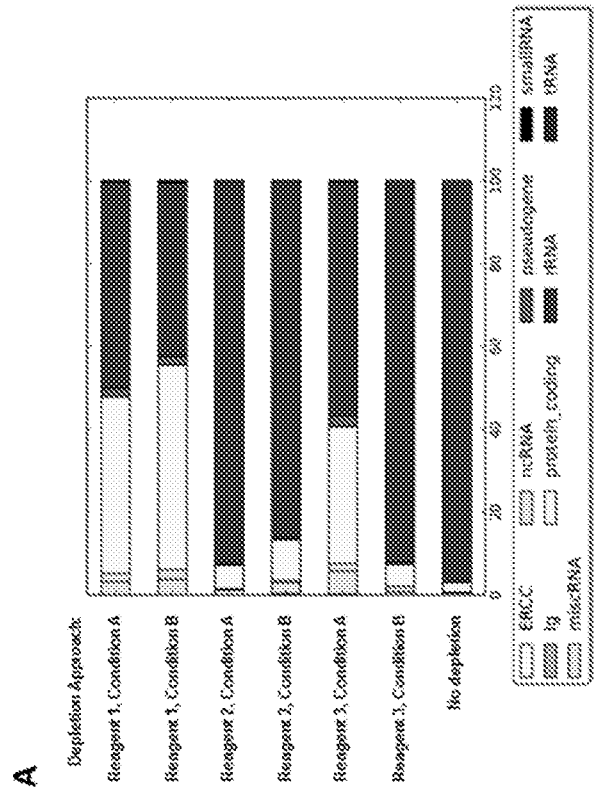
Figure 22:
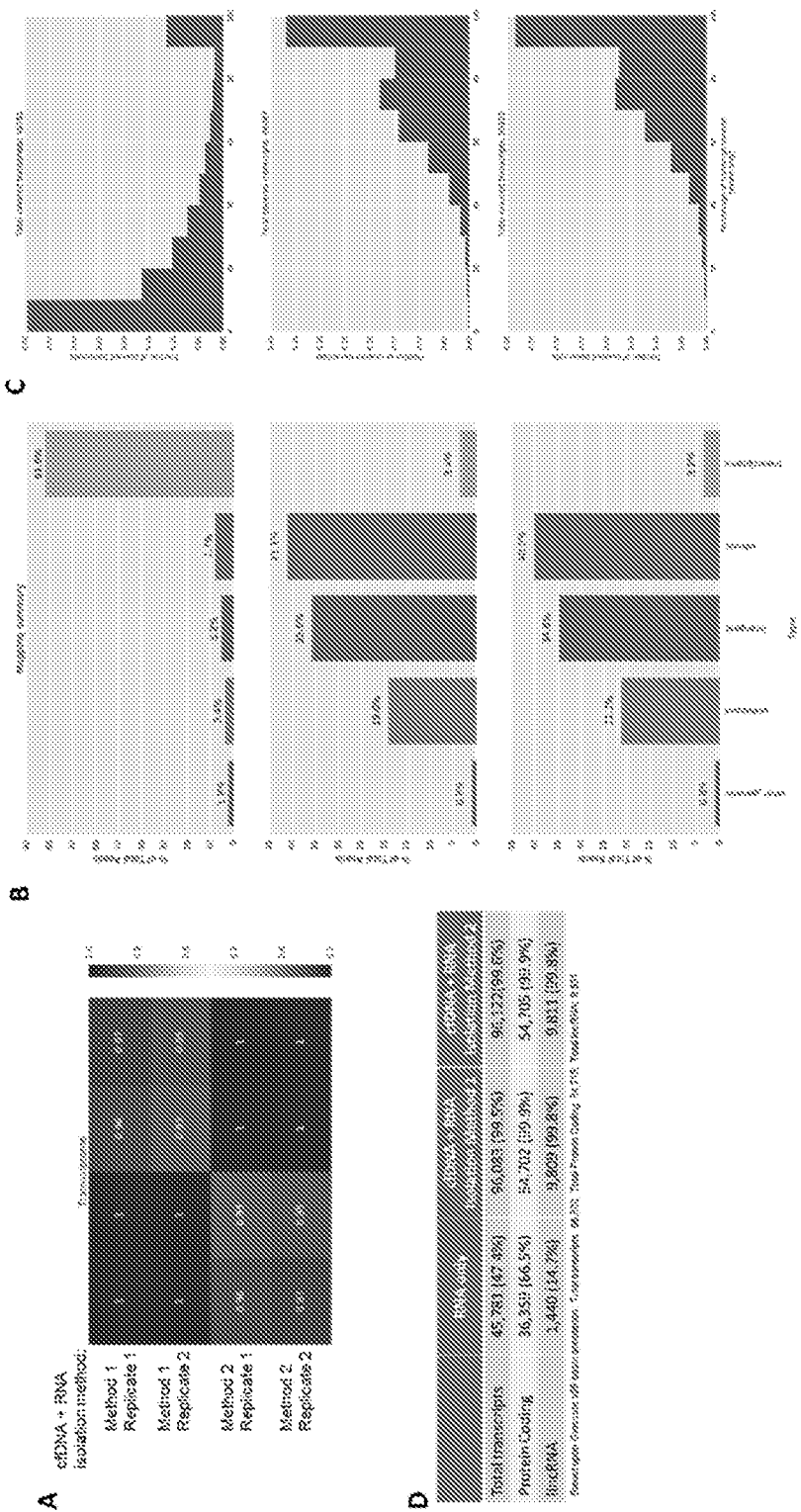
FIG. 22 demonstrates library preparation methods for total RNA and total nucleic acid (cfDNA+RNA).

FIG. 21 demonstrates various ribosomal RNA depletion approaches. To minimize variability, replicate RNA extractions were isolated from a control plasma pool. To further avoid variability, all samples were prepared utilizing the same RNAseq library procedure. Individual samples were subjected to one of three commercially available ribosomal sequences depletion approaches (referred to as Reagent 1, Reagent 2 and Reagent 3), for which depletion could occur either at the level of RNA or cDNA. For Reagent 1. Condition A refers to commercially available protocol while Condition B refers to identified optimal protocol. A sample that was not depleted of ribosomal RNA was included as a no treatment control. All samples were subjected to deep sequencing and were downsampled to normalize read counts for analysis. FIG. 21A shows that the proportion of transcriptome reads illustrates how selection of optimal condition can drastically impact the efficacy of depletion and the subsequent recovery of RNAs of interest. FIG. 21B provides a comparison of depleted versus non-depleted sample further illustrates the importance of selecting the optimal condition that has the most efficient depletion of unwanted ribosomal RNAs while preserving the initial library diversity (purple) and minimizing losses (pink), as well as allowing for elucidation of additional RNAs (blue) as compared to treatment. Here, Condition B using Reagent 1 was found to result in most optimal ribodepletion leading to 17-fold improvement in protein coding reads, 93.5% overlap with no depletion and 96.5% new transcripts detected.

FIG. 22 demonstrates both total RNA and total nucleic acid (cfDNA+RNA) library preparation methods. Nucleic acids were isolated from control plasma using one of three methods: one that isolates high quality RNA only and two different methods that isolate cfDNA in addition to RNA. To minimize variability, samples from each of these libraries were prepared for sequencing using the same approach. FIG. 22A shows that highly reproducible libraries are produced using this library method and both isolation methods produce highly similar starting material. FIG. 22B provides mapping metrics, while FIG. 22C provides transcript coverage which demonstrates increased transcript coverage as detected by combining RNA and cfDNA compared with RNA only. FIG. 22D provides the transcripts identified for RNA only (top), cfDNA+RNA Method 1 (middle) and Method 2 (bottom). By combining the RNA and DNA from the sample and subjecting them to the same workflow, the detection of total transcripts (coding and non-coding) increased from 47.4% (RNA only) to 99.6% (RNA+cfDNA), protein coding transcripts detection from 66.5% (RNA only) to 99.9% (RNA+cfDNA) and lincRNA detection from 14.7% (RNA only) to >99% (RNA+cfDNA).

Figure 23:
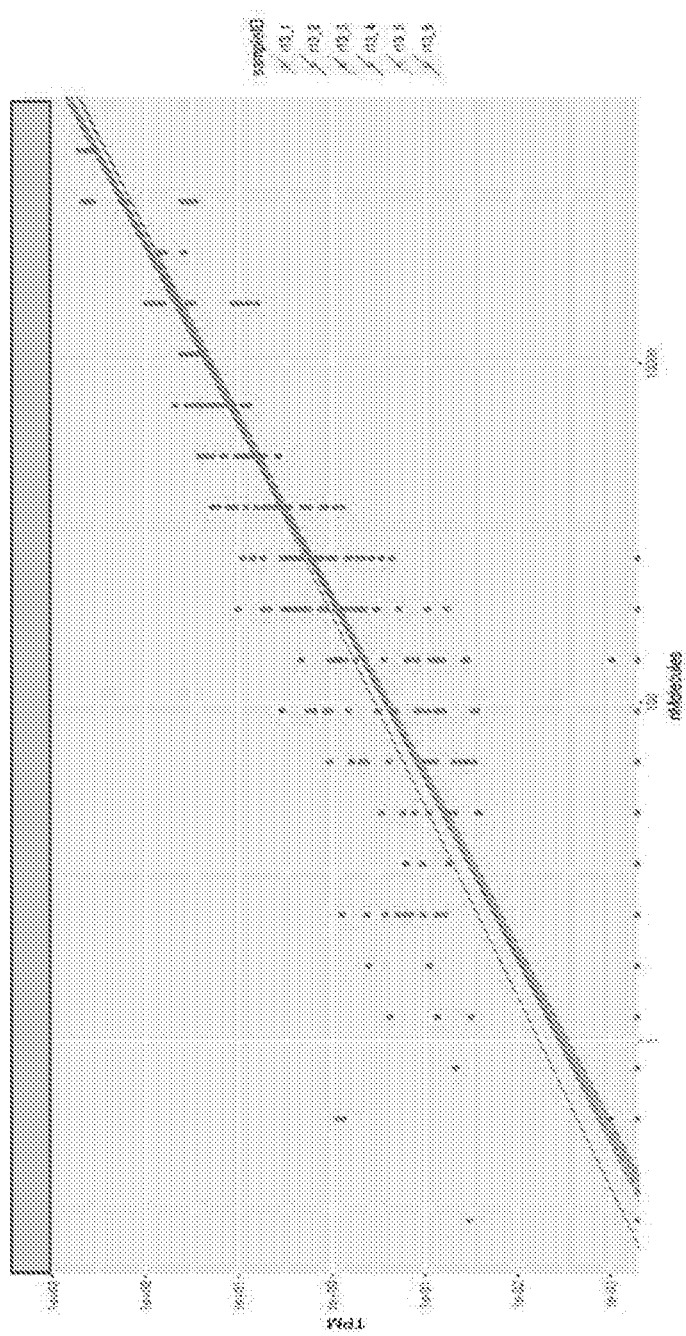
FIG. 23 is a plot demonstrating the limit of detection of total RNASeq assay based ERCC exogenous RNA spike-ins for six independent library replicates constructed from plasma.

FIG. 23 demonstrates the limit of detection of total RNASeq assay based exogenous RNA spike-ins in six independent library replicates constructed from plasma. The figure demonstrates consistent detection of RNA down to 10 molecules or less. The dynamic range of this assay spans across five orders of magnitude, from 10 to 1.8 million molecules.

Following library quantification, the libraries are normalized, multiplexed and subjected to sequencing using a next generation sequencing platform. The sequencing data is then demultiplexed if necessary and transcript/gene counts are generated by either mapping against an existing genome or transcriptome reference sequence or against de novo assembled genomes or transcripts (see FIG. 16, FIG. 24).

FIG. 24 provides an exemplary RNASeq browser to display QC metrics and analysis results.

The UMI tags on each sequence can then be used to identify fragments that arise due to PCR duplication. The counts are normalized among others for library size, GC-bias, sequence-bias, sequencing depth. These counts can then be used to perform a differential expression analysis between samples pertaining to different conditions (e.g. tumor/normal) to generate a list of biomarkers that can discriminate between the sample types, as in FIG. 25, which provides an exemplary differential expression browser to display and evaluate the results of differential expression analyses.

The reference aligned data can be used for profiling sequence variation such as but not limited to single nucleotide polymorphisms, insertions/deletions, fusions, inversions and repeat expansions.

Example 5

A hybridization-based target enrichment off-the-shelf commercially available kit, created for tissue analysis including formalin-fixed paraffin embedded (FFPE) tissue was used to test for applicability to extracellular vesicle samples (exoRNA and cfDNA). The kit contains targets the detection of fusions, insertions/deletions, single nucleotide polymorphisms, and copy number variations.

Figure 26:
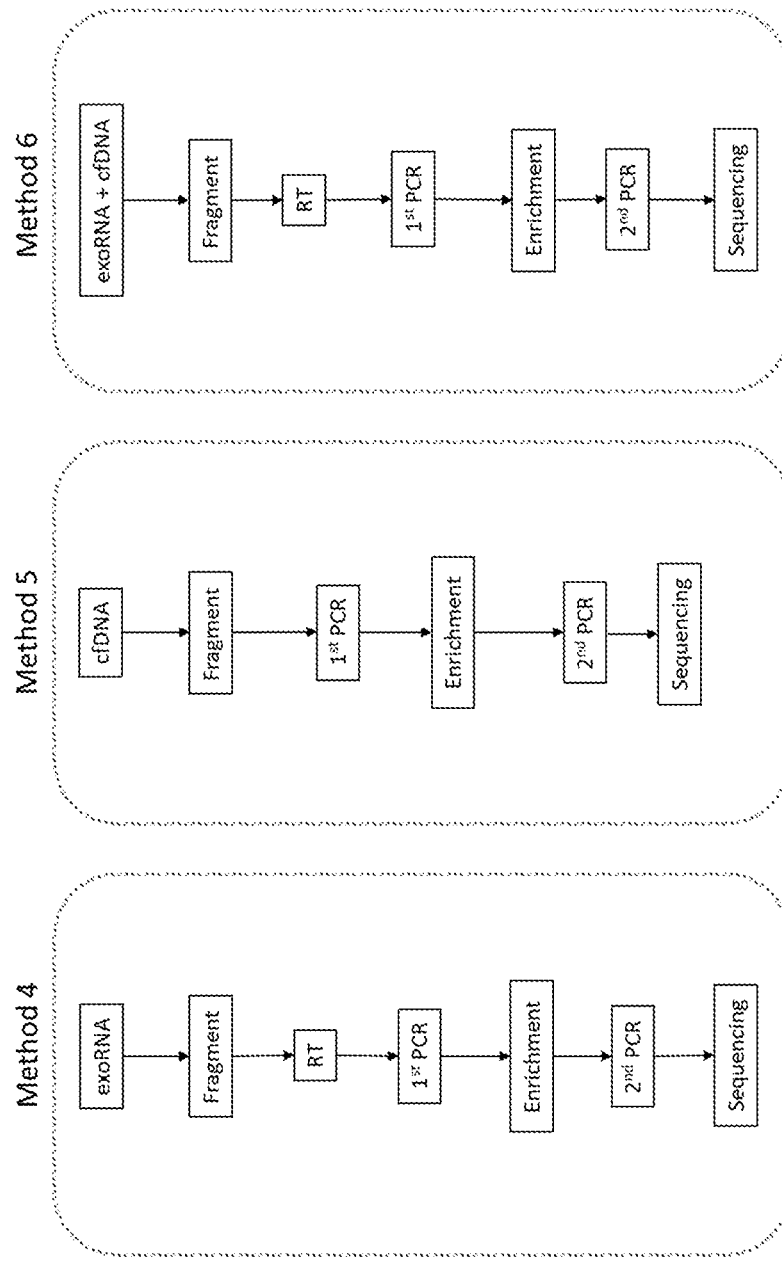
FIG. 26 is a schematic comparing two off-the-shelf processes for exosomal samples (Method 4 and Method 5) with an improved process combining these separate streams into a single method (Method 6).

To test the feasibility of adapting the off-the-shelf process for exosomal samples, we examined the two processes of Method 4 and Method 5, as depicted in FIG. 26. The targeted enrichment parameters outlined in Table 1 were investigated, and we found that ExoRNA, and cfDNA are comparable to low input control RNA (Universal Human Reference RNA) and DNA (Normal Genomic DNA). The expected range for target enrichment (reads mapped to the target specific sequences) is 70%-99% for exoRNA and cfDNA.

TABLE 1

| Sample Type | Target Enrichment |
| --- | --- |
| Universal Human Reference RNA Control-Standard Input | 91.4% |
| Universal Human Reference RNA Control-Low Input | 88.1% |
| Normal Genomic DNA Control - Standard Input | 90.1% |
| Normal Genomic DNA Control -Low input | 83.0% |
| exoRNA only | 95.1% |
| cfDNA only | 83.2% |

The percent of reads mapped for exo RNA and cfDNA to the transcriptome is 30%0/to 95%, intronic regions is 5% to 60%, and intergenic regions is 0.2% to 10%.

In exoRNA and cfDNA, sequence bases of targets are covered between at >90% with one read.

We found an average depth of coverage of greater than 30,000× is required to detect low frequency mutations.

Example 6

The experimental goal is to investigate the feasibility of exosomal samples (exoRNA and cfDNA combined) through a Pan-cancer commercially available kit (Method 6 in FIG. 26). The kit is created for the detection of RNA transcripts and fusions in FFPE and cancer samples.

We investigated the target enrichment for exoRNA, cfDNA, and exoRNA and cfDNA combined. The target enrichment results for exosomal samples are comparable to the Universal Human Reference RNA Control used.

TABLE 2

| Sample Type | Target Enrichment |
| --- | --- |
| Universal Human Preference RNA Control- Standard Input | 94.89% |
| exoRNA | 95.9% |
| cfDNA | 78.0% |
| exoRNA and cfDNA combined | 90.7% |

The expected range for target enrichment (reads mapped to the target specific sequences) is 75%-99% for exoRNA, cfDNA, and exoRNA and cfDNA combined.

The percent of reads mapped for exoRNA and cfDNA combined to the transcriptome is 35% to 95%, intronic regions are 8% to 45%, and intergenic regions are 0.4% to 5%.

In exoRNA and cfDNA combined, sequence bases of targets are fully covered at >80% with one read.

The combination of exoRNA and cfDNA provides more read coverage per gene and greater target enrichment as seen in FIG. 17.

Example 7

The objective of this study is to investigate: (1) the effect of different fragmentation times on total RNASeq data; (2) the effect of DNase treatment; (3) the effect of ribodepletion; and (4) the effect of synthetic spike-ins. The method is Long RNASeq Workflow Method 1 as outlined above, following RNA isolation from a 2 mL sample of normal human plasma using the EXO-50 method.

Generally, samples are subjected to DNase treatment, followed by synthetic spike-in, and a single ribodepletion step. Samples are as in Table 3.

TABLE 3

| Sample | Sample Description |
| --- | --- |
| 1 | No fragmentation |
| 2 | No fragmentation |
| 3 | Short fragmentation |
| 4 | Short fragmentation |
| 5 | Medium fragmentation time |
| 6 | Medium fragmentation time |
| 7 | Long fragmentation time |
| 8 | Long fragmentation time |
| 9 | Standard fragmentation time |
| 10 | Standard fragmentation time |
| 11 | Synthetic spike-ins 2 |
| 12 | Synthetic spike-ins 2 |
| 13 | DNase 2 |
| 14 | DNase 2 |
| 15 | DNase- Short Fragmentation Ribodepletion 2 |
| 16 | DNase- Short Fragmentation Ribodepletion 2 |

Figure 27:
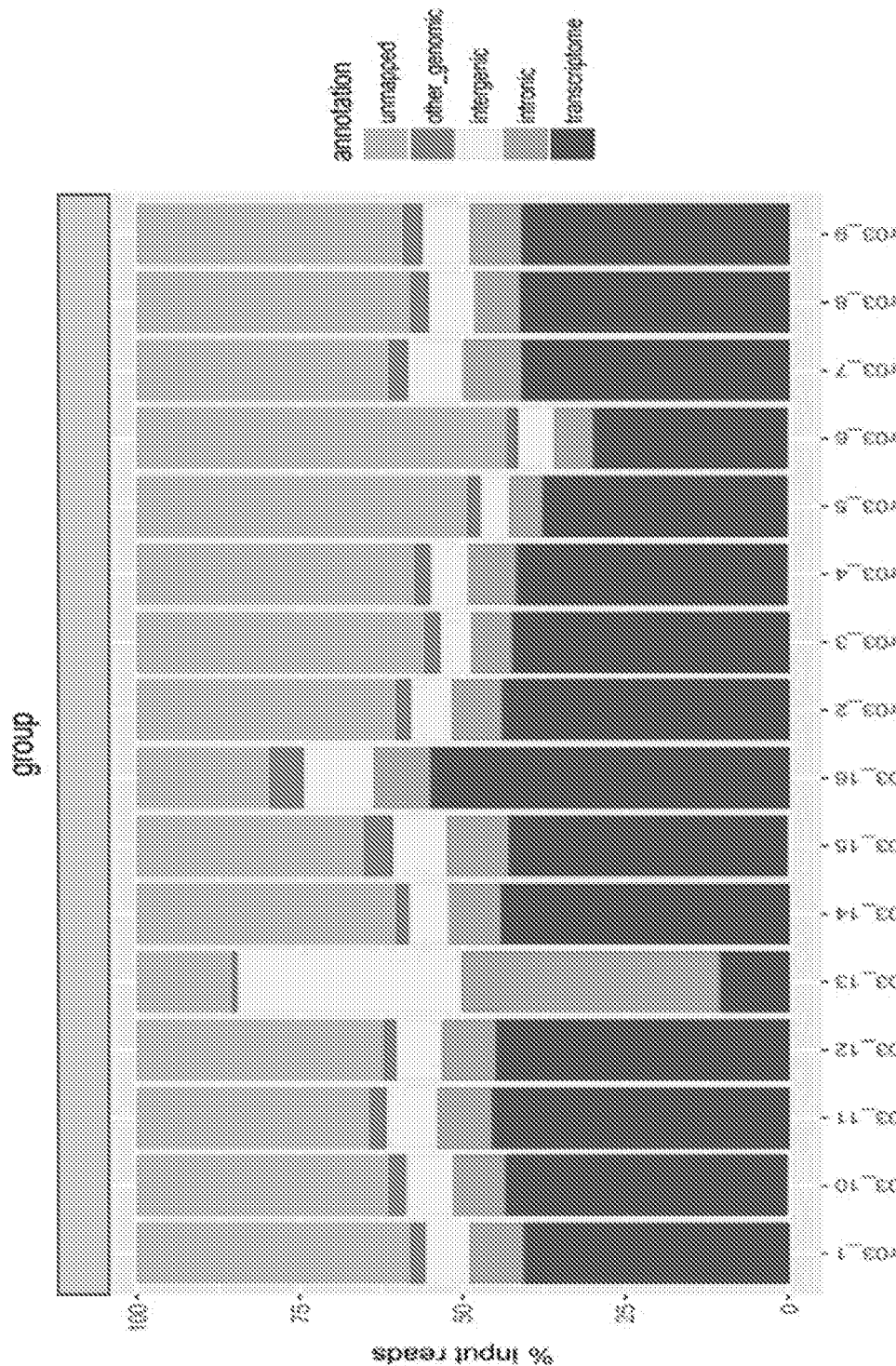
FIG. 27 annotates the unmapped, other genomic, intergenic, intronic and transcriptome coverages as a measure of percent input reads per sample.
Figure 28:
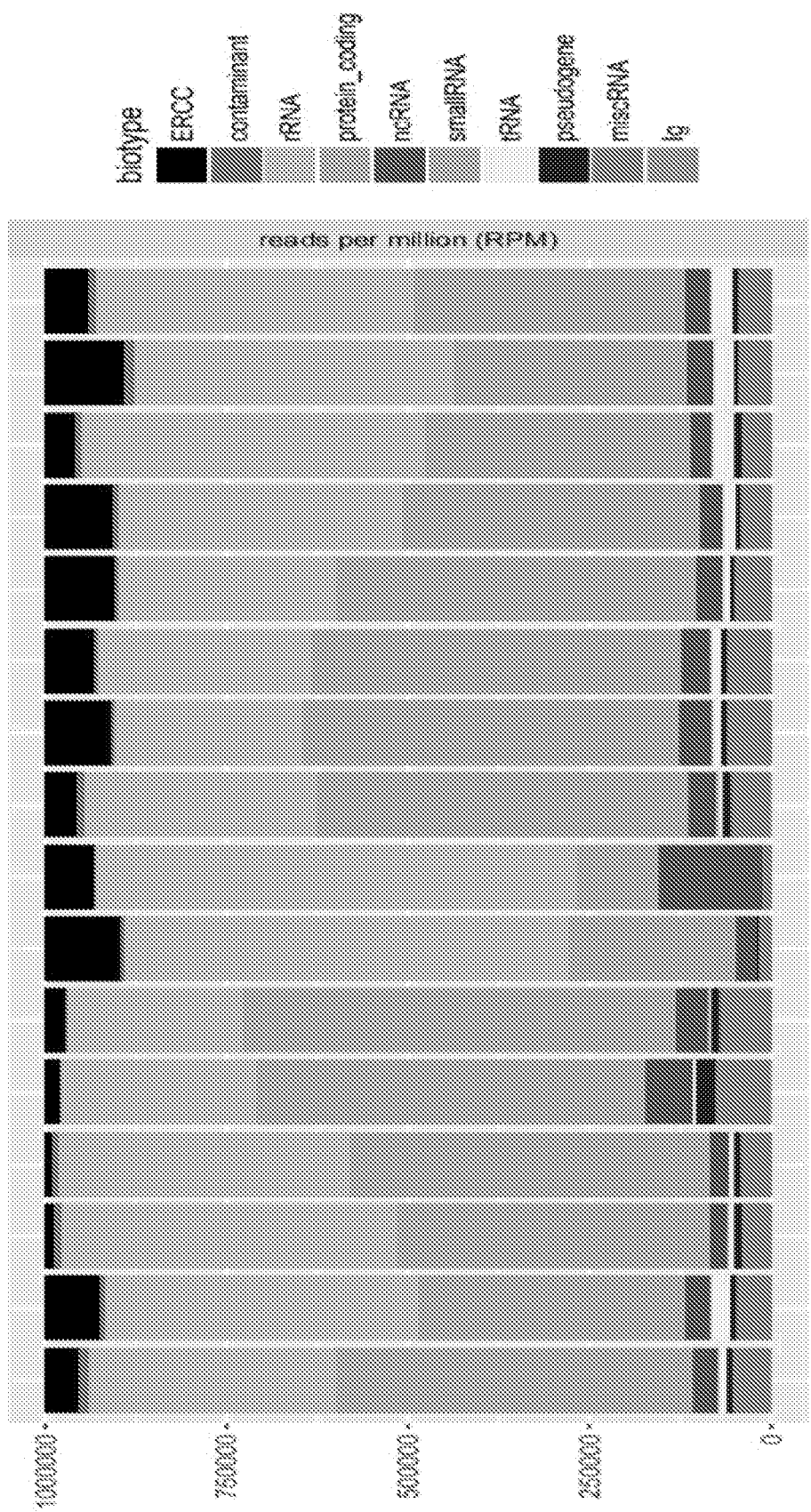
FIG. 28 annotates each of the biotypes ERCC, contaminant, rRNA, protein coding genes, ncRNA, small RNA, tRNA, pseudogene, miscRNA and Ig as reads per million.

Mapping statistics of the analyzed samples are as in FIGS. 27-28, and show consistency between replicates. With reference to FIG. 27, it can be seen that approximately 40-50% of reads map to transcriptome in all samples.

As evident from FIG. 28, 30-40% of reads map to ribosomal RNAs and 40-50% of reads map to protein coding RNA.

Figure 29:
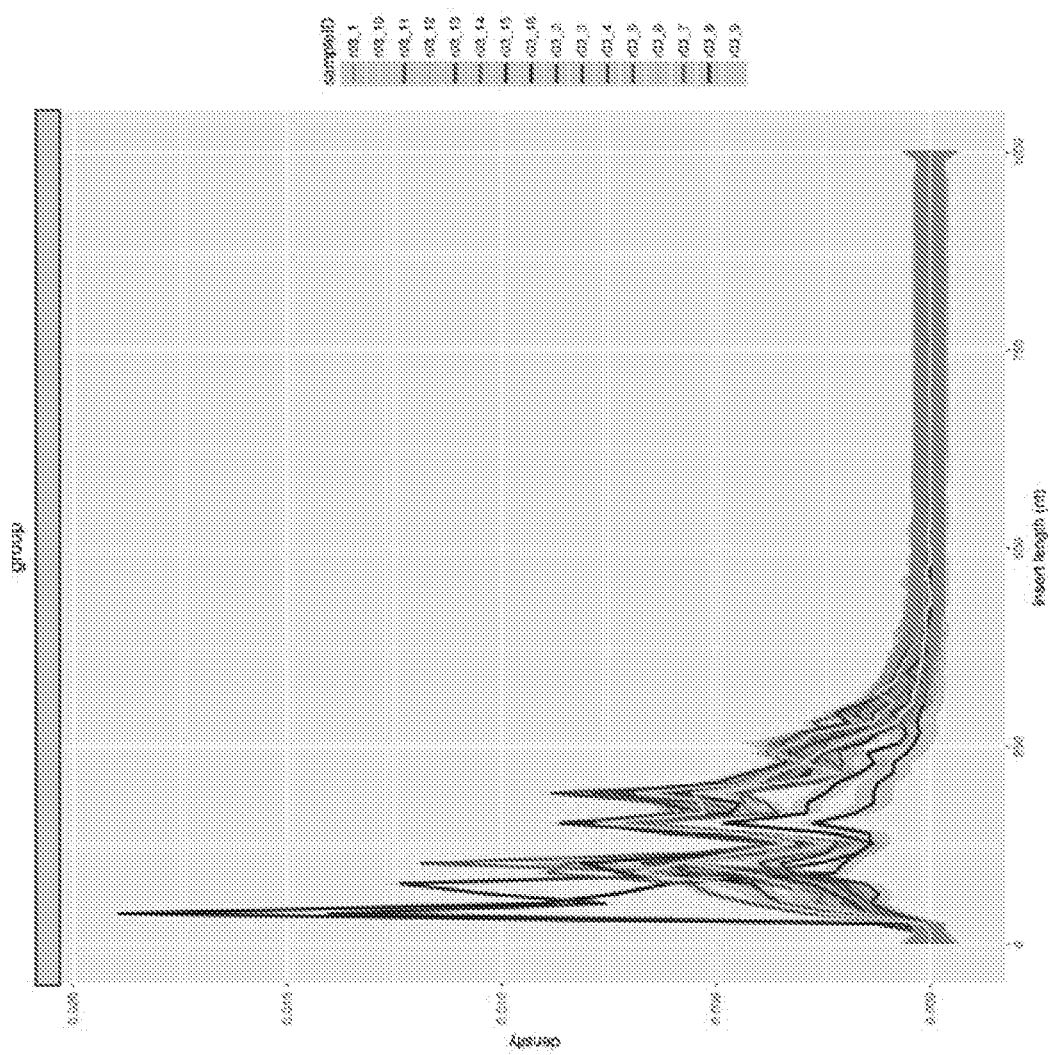
FIG. 29 is a plot showing insert length (number of nucleotides) versus density.

Insert size distribution is relatively consistent between replicates of different libraries, as shown in FIG. 29.

Figure 30:
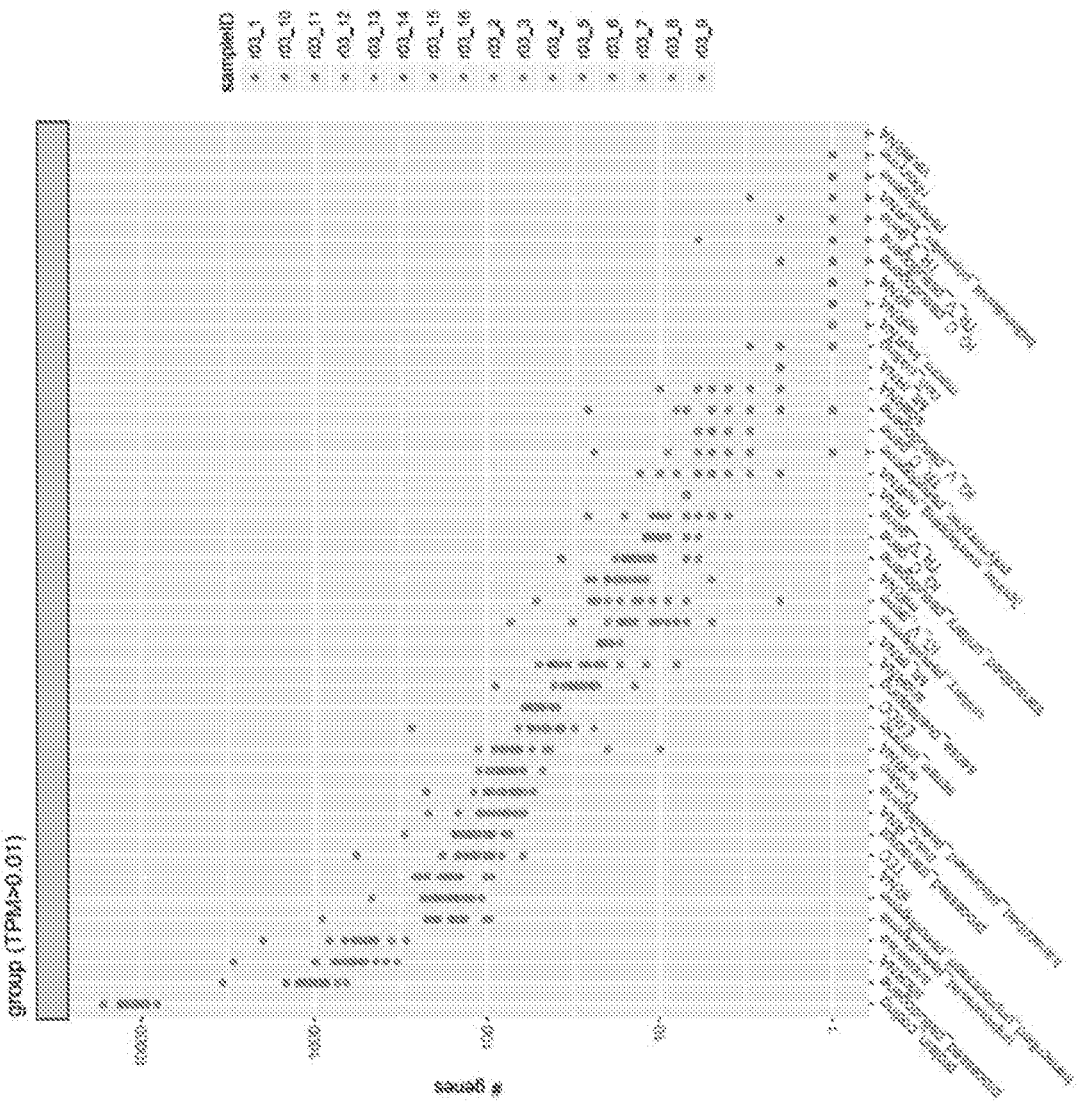
FIG. 30 plots gene biotype on the x-axis by number of genes on the y-axis.
Figure 31:
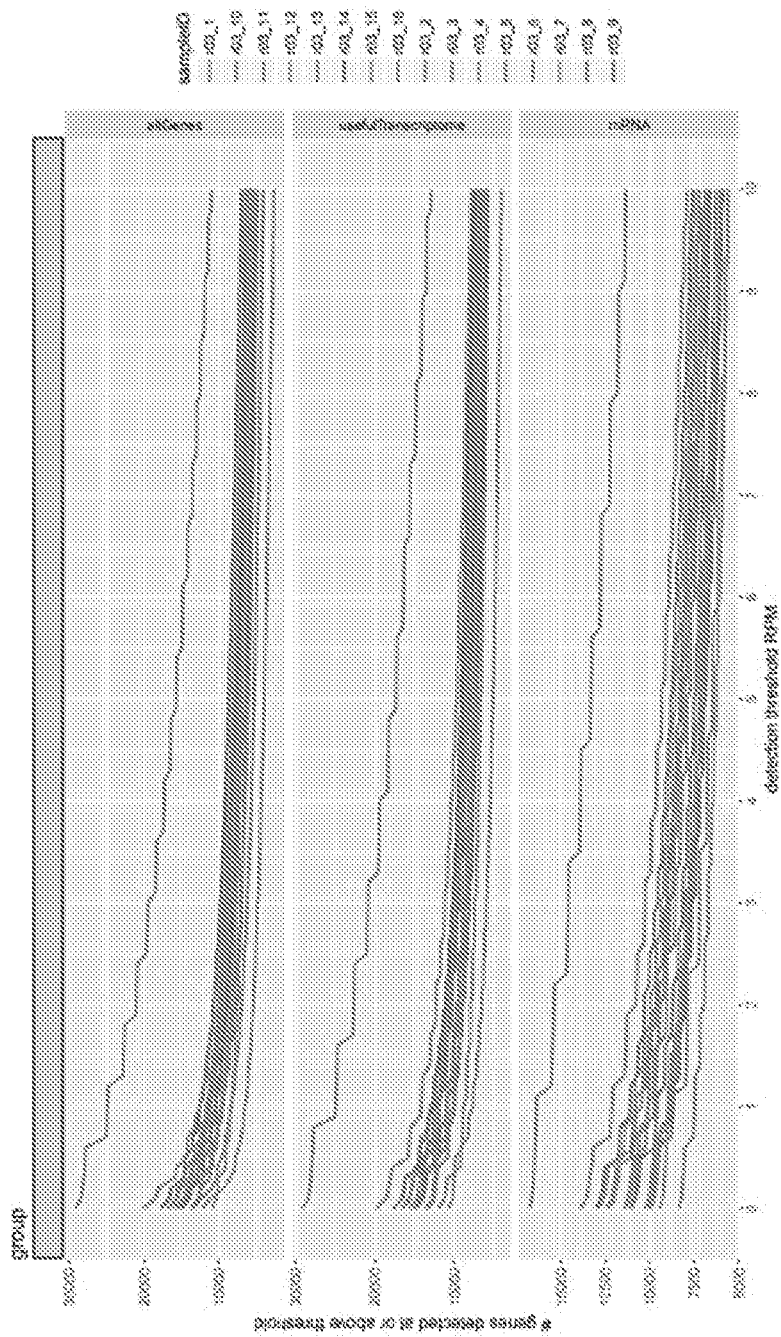
FIG. 31 provides a plot of detection threshold RPM per number of genes detected at or above threshold for all genes (top), useful transcriptome (middle), and mRNA (bottom).

Transcriptome coverage is also investigated, as shown in FIG. 30 and FIG. 31. Libraries detect more than 10,000 protein coding genes. Protein coding genes are most abundant in exosomes, followed by processed pseudogenes and lincRNA.

Figure 32:
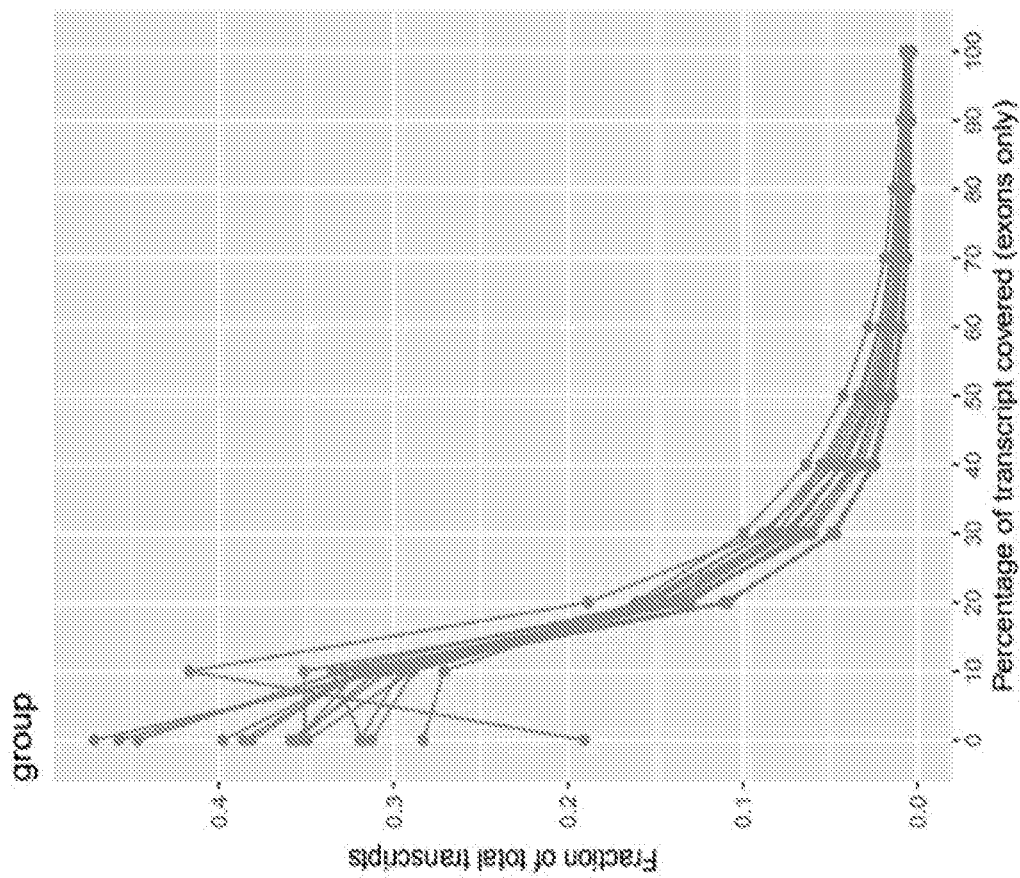
FIG. 32 plots percentage of transcript covered (exons only) on the x-axis versus the fraction of total transcripts on the y-axis.

Transcript coverage is also relatively consistent across all samples and replicates as show in FIG. 32.

Figure 33:
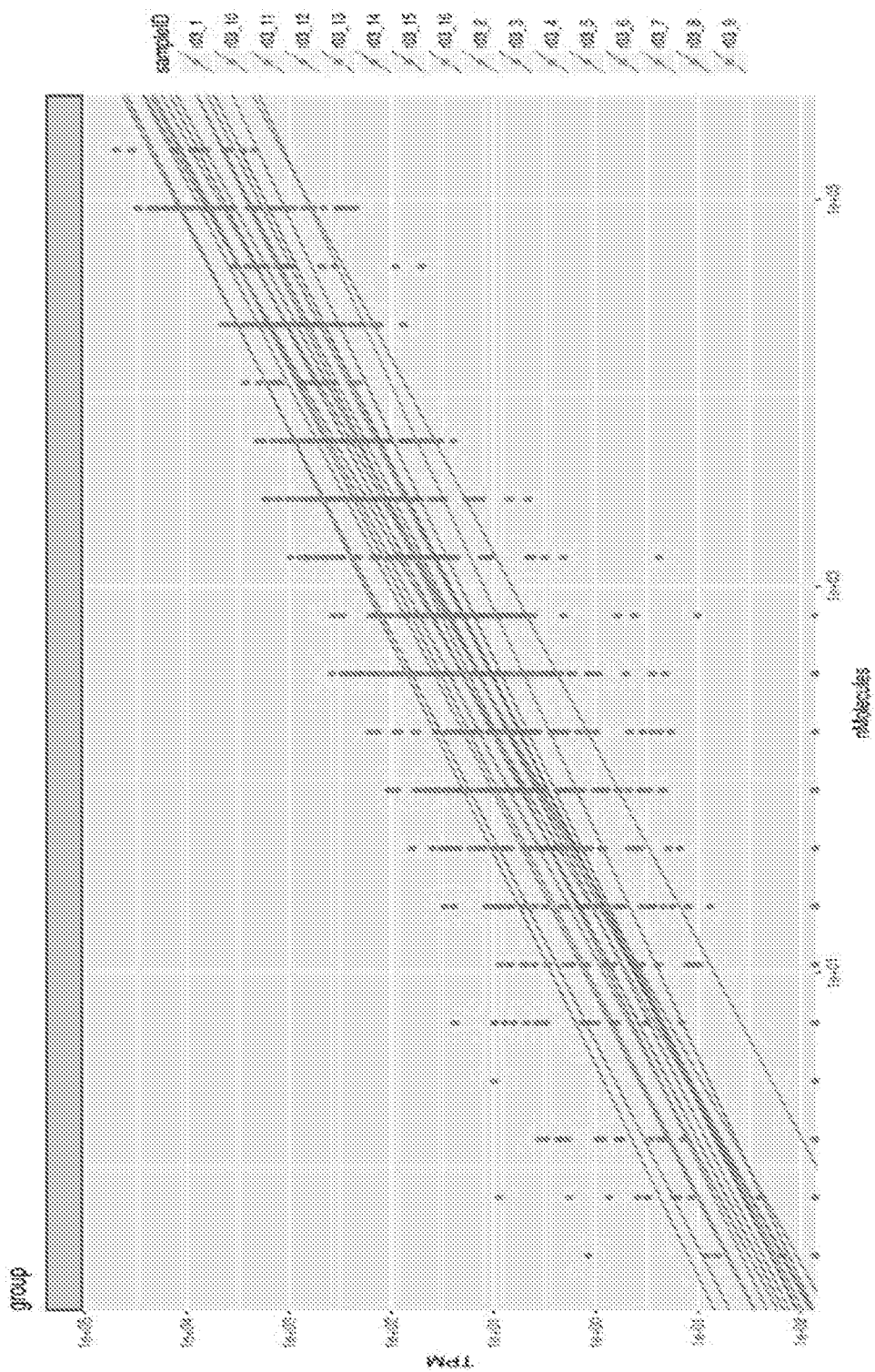
FIG. 33 demonstrates the limit of detection for ERCC transcripts.

FIG. 33 demonstrates the limit of detection for synthetic spike-ins transcripts. The dynamic range of synthetic spike-ins is over five orders of magnitude.

Figure 34:
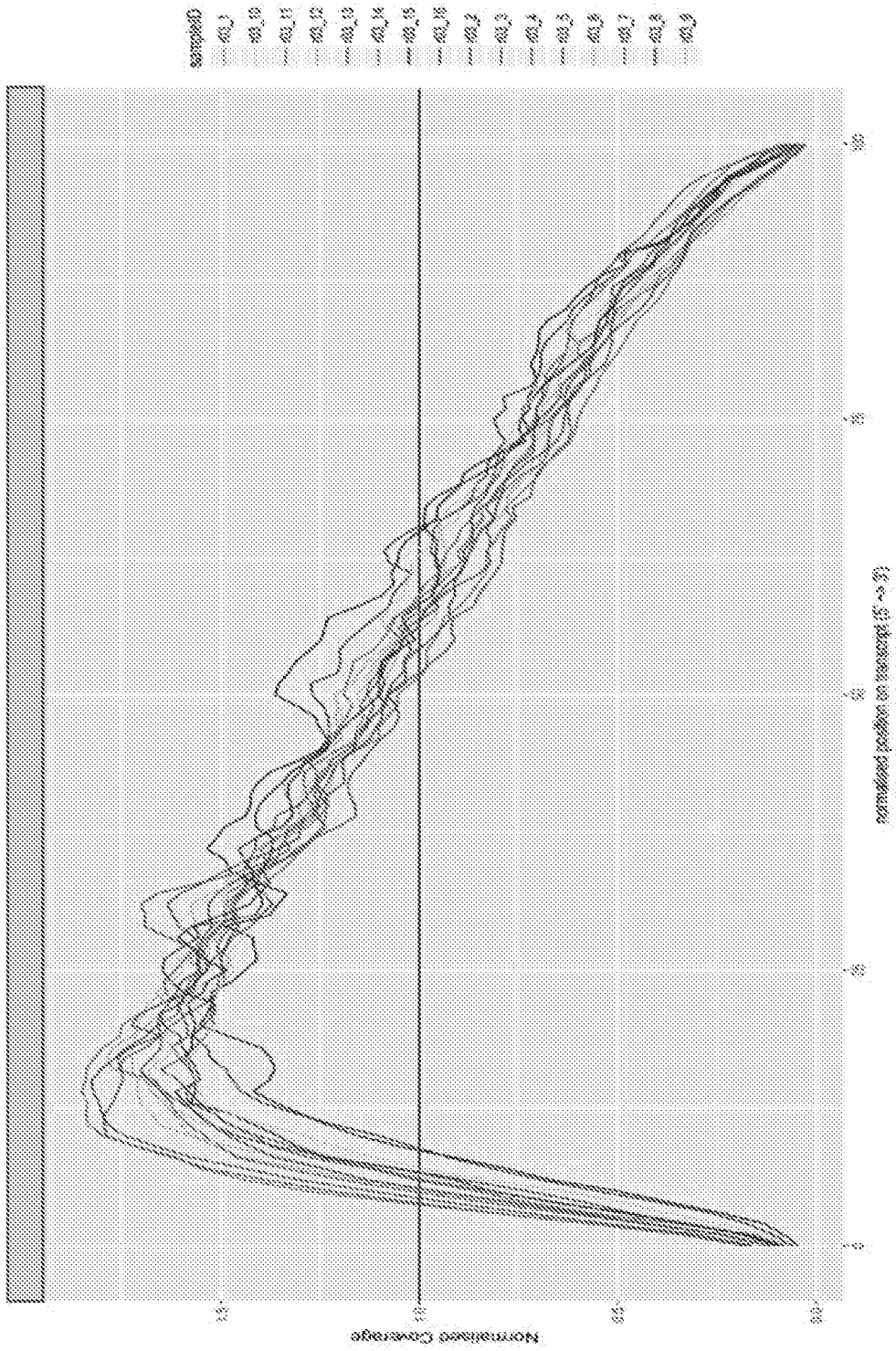
FIG. 34 plots the normalized position on the transcript (5' to 3') versus normalized coverage.

FIG. 34 demonstrates 5' to 3' transcript coverage shown in all libraries.

Example 8

The objective of this example is to construct RNASeq libraries from normal human plasma exosomes using Long RNASeq Workflow Method 3 and investigate (1) the number of amplification cycles; (2) the effect of ribodepletion. The method is the Long RNASeq Workflow Method 3 as above, with synthetic spike-in, following RNA isolation from a 2 mL sample of normal human plasma using the EXO-50 method.

Generally, samples are subjected to DNase treatment, ribodepletion, addition of synthetic spike-ins, reverse transcription, a variable number of cycles of amplification, and further processing (including cleanup steps) according to the Workflow Method 3. Samples are identified as in Table 4.

TABLE 4

| Sample | Sample Description |
|---|---|
| 1 | Amplification 1 |
| 2 | Amplification 1 |
| 3 | Amplification 2 |
| 4 | Amplification 3 |
| 5 | Amplification 3 |
| 6 | Amplification 4 |
| 7 | Amplification 4 |
| 8 | Ribodepletion 2 |
| 9 | Ribodepletion 2 |

Figure 35:
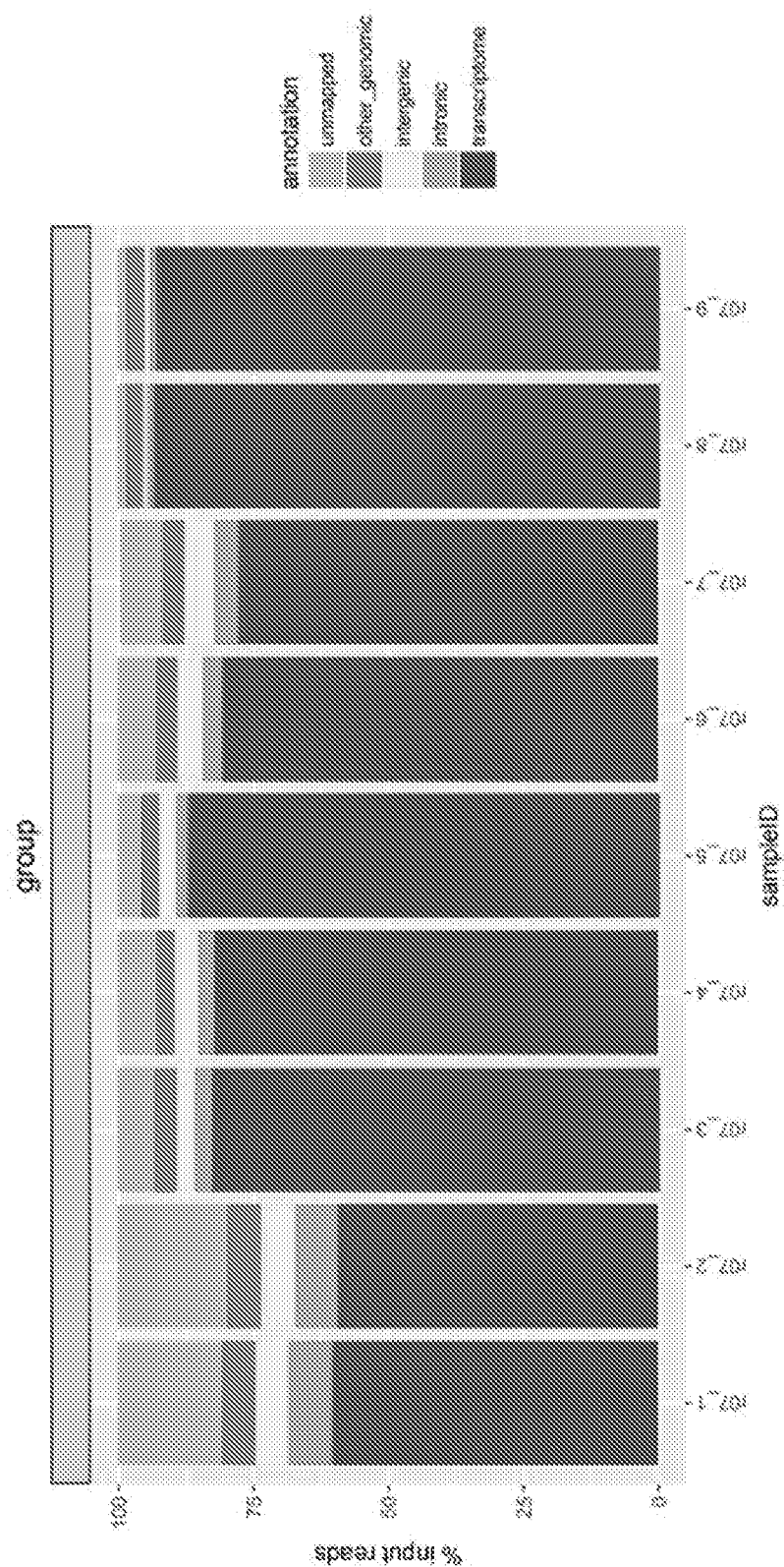
FIG. 35 annotates the unmapped, other genomic, intergenic, intronic and transcriptome coverages as a measure of percent input reads per sample.
Figure 36:
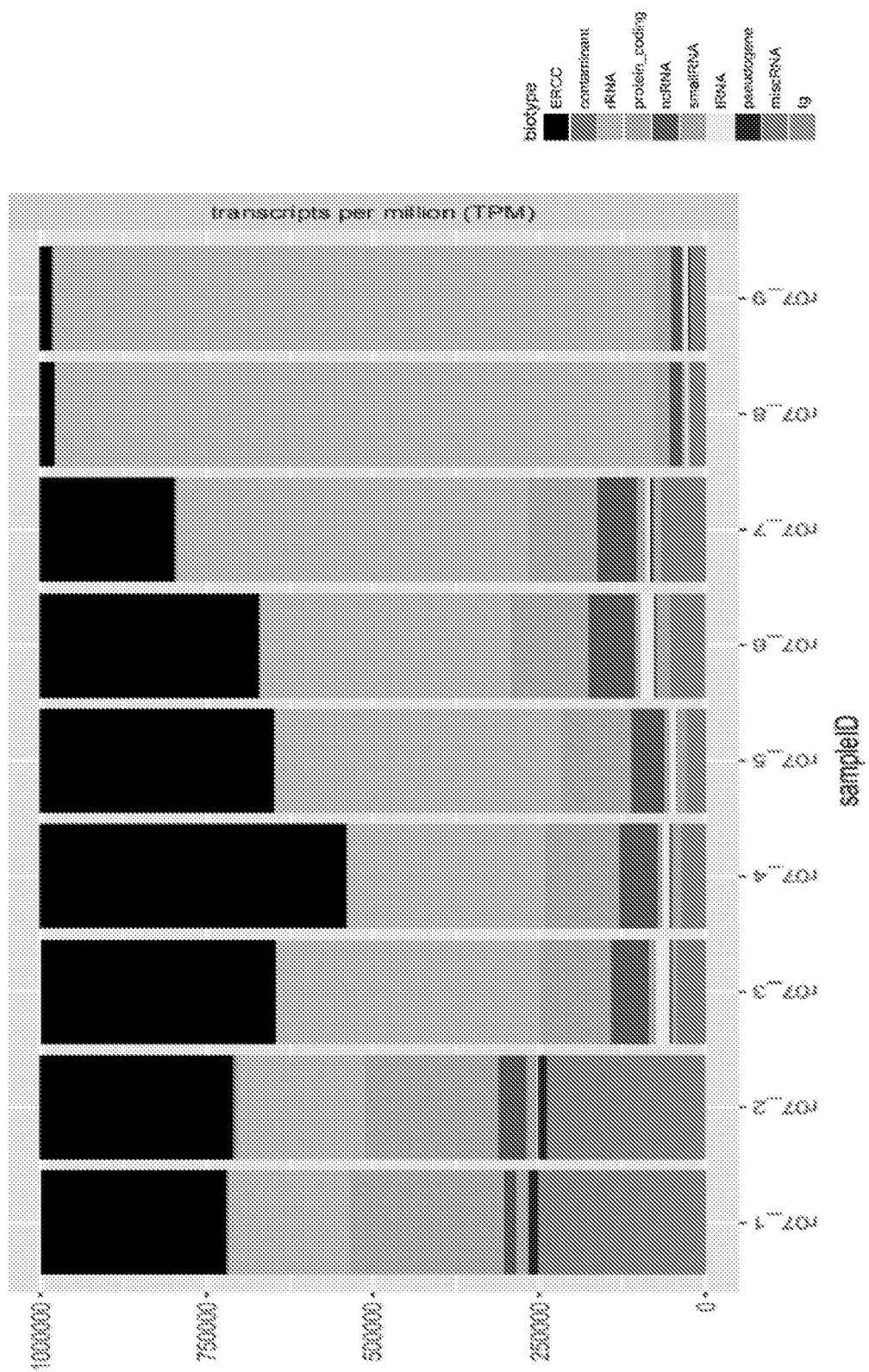
FIG. 36 annotates each of the biotypes ERCC, contaminant, rRNA, protein coding genes, ncRNA, small RNA, tRNA, pseudogene, miscRNA and Ig as reads per million.

Mapping statistics of the analyzed samples are as in FIGS. 35-36. As shown in FIG. 35, the majority of reads map to transcriptome in all samples.

As evident from FIG. 36, the lowest proportion of ribosomal reads in libraries is observed in sample 1 and 2 and the highest proportion of protein coding and misc RNA reads are also observed in sample 1 and 2.

Figure 37:
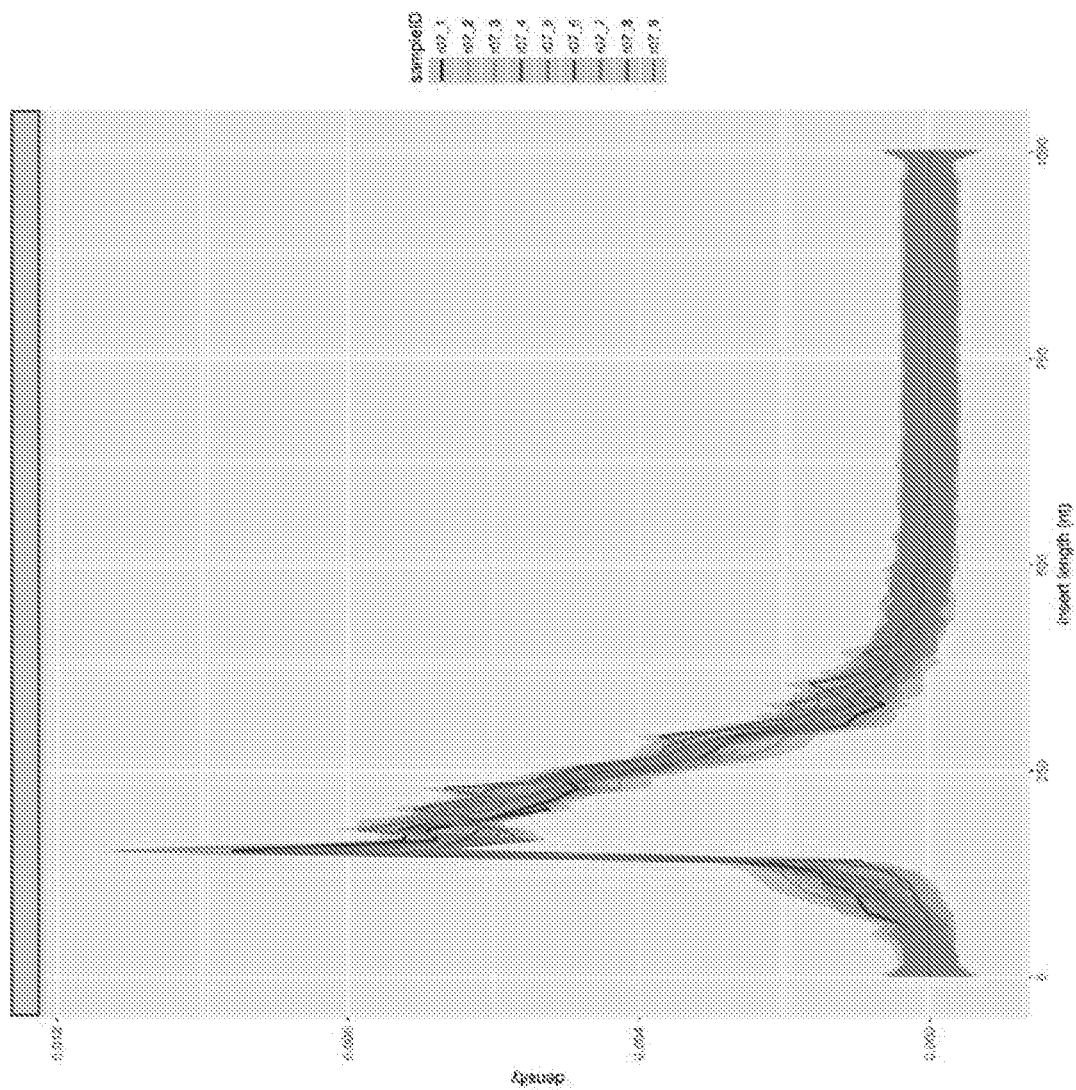
FIG. 37 is a plot showing insert length (number of nucleotides) versus density.

Insert size distribution is highly consistent across replicates and across all samples, as shown in FIG. 37.

Figure 38:
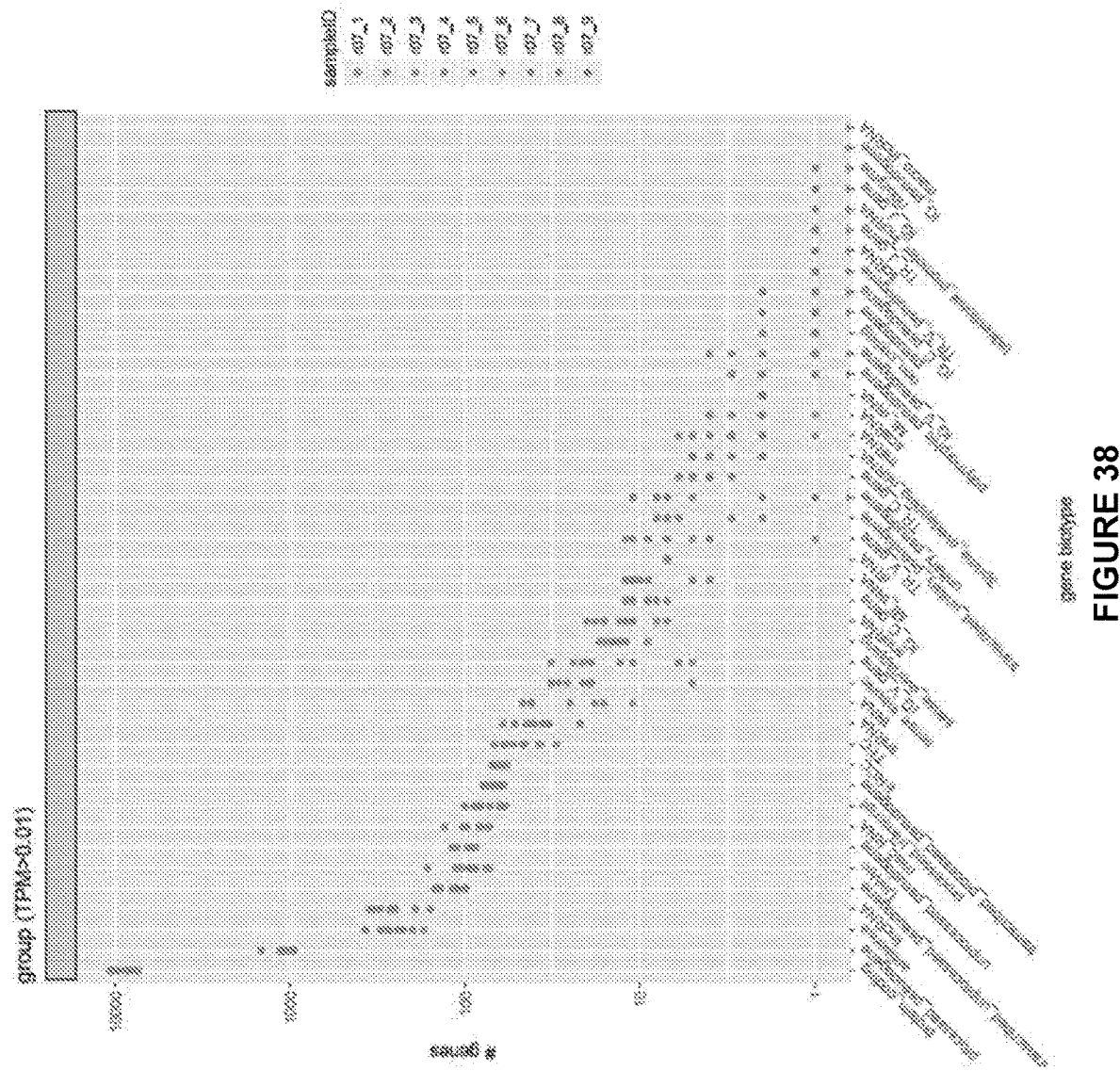
FIG. 38 plots gene biotype on the x-axis by number of genes on the y-axis.

Transcriptome coverage is investigated, as shown in FIG. 38. Overall, transcriptome coverage is consistent across replicates and across all samples.

Figure 39:
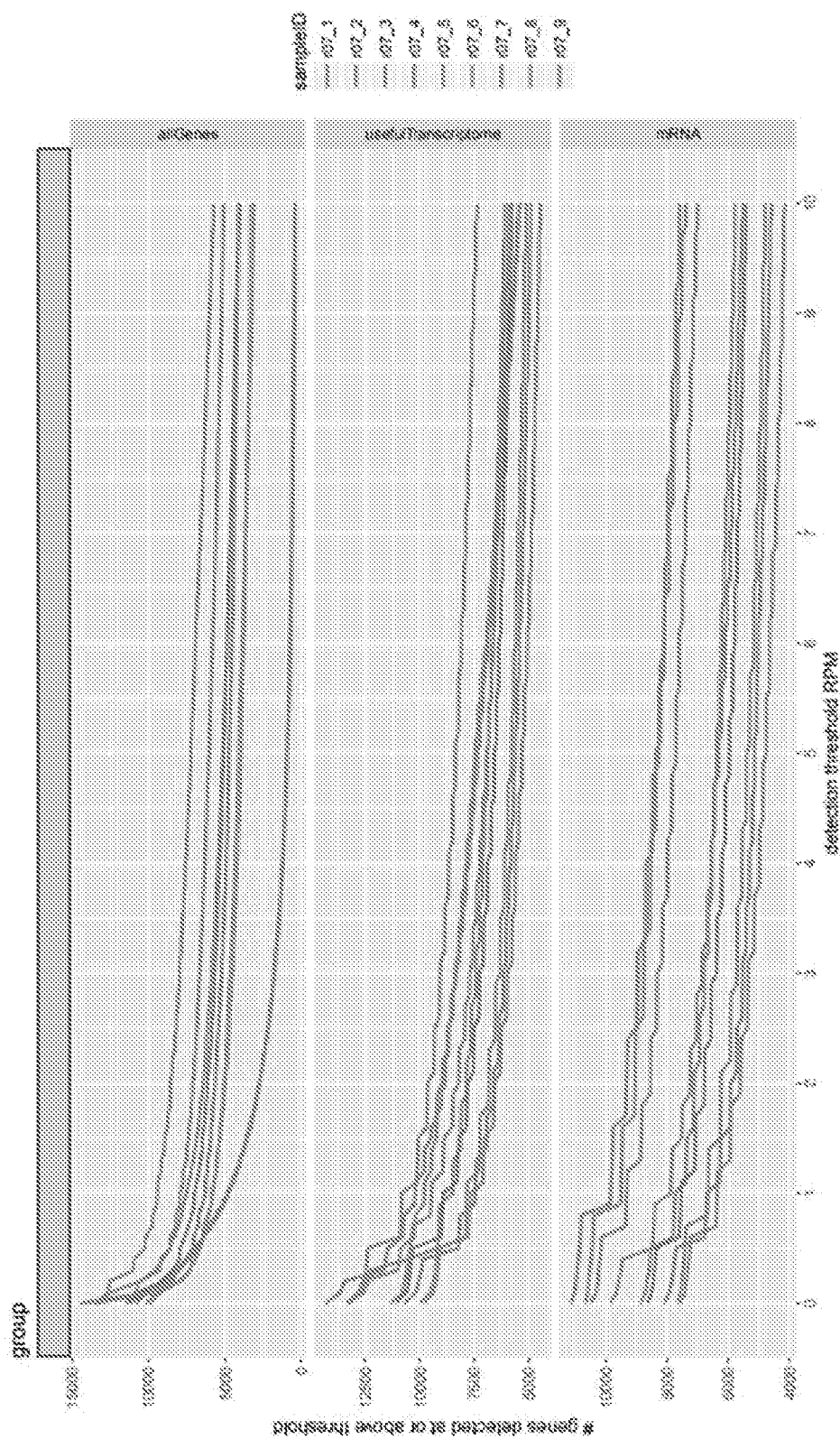
FIG. 39 provides a plot of detection threshold RPM per number of genes detected at or above threshold for all genes (top), useful transcriptome (middle), and mRNA (bottom).

FIG. 39 shows that overall, there is consistent detection of genes across samples at different detection thresholds.

Figure 40:
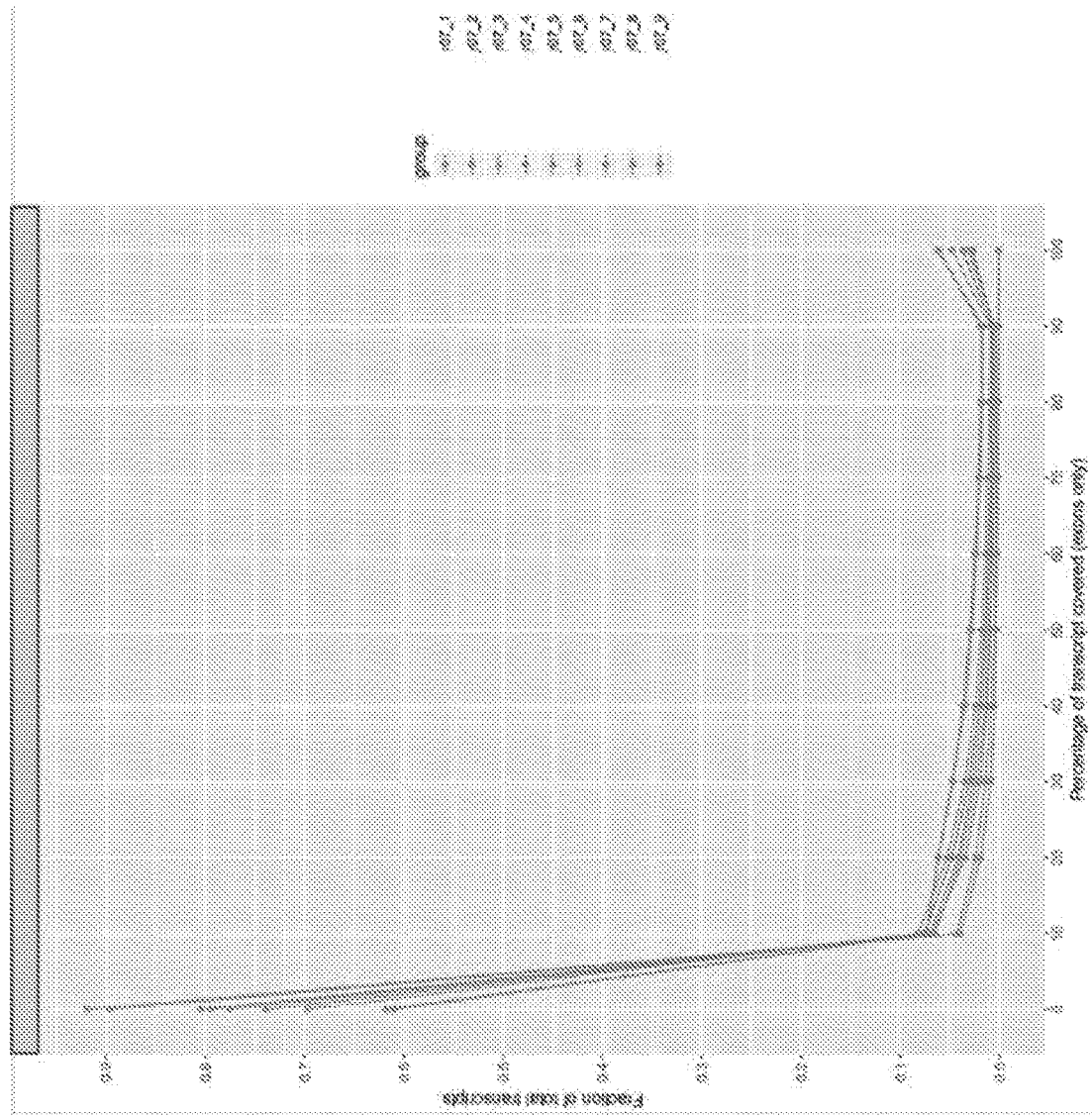
FIG. 40 plots percentage of transcript covered (exons only) on the x-axis versus the fraction of total transcripts on the y-axis.

Transcript coverage is overall consistent across samples at different detection thresholds as show in FIG. 40.

Figure 41:
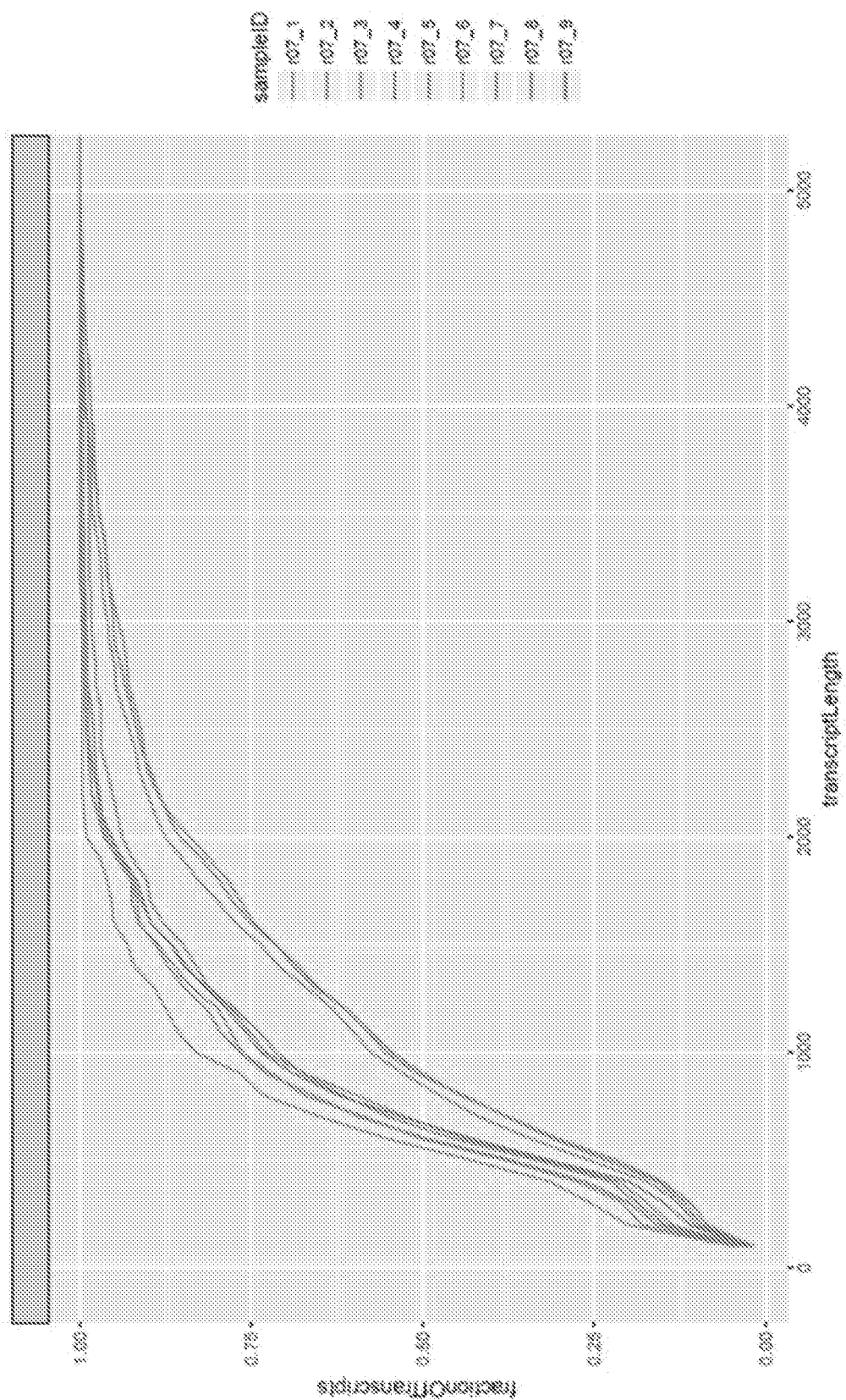
FIG. 41 highlights the size of transcripts having >80% coverage, by plotting transcript length versus fraction of transcripts.

FIG. 41 highlights the size of transcripts with >80% coverage.

Figure 42:
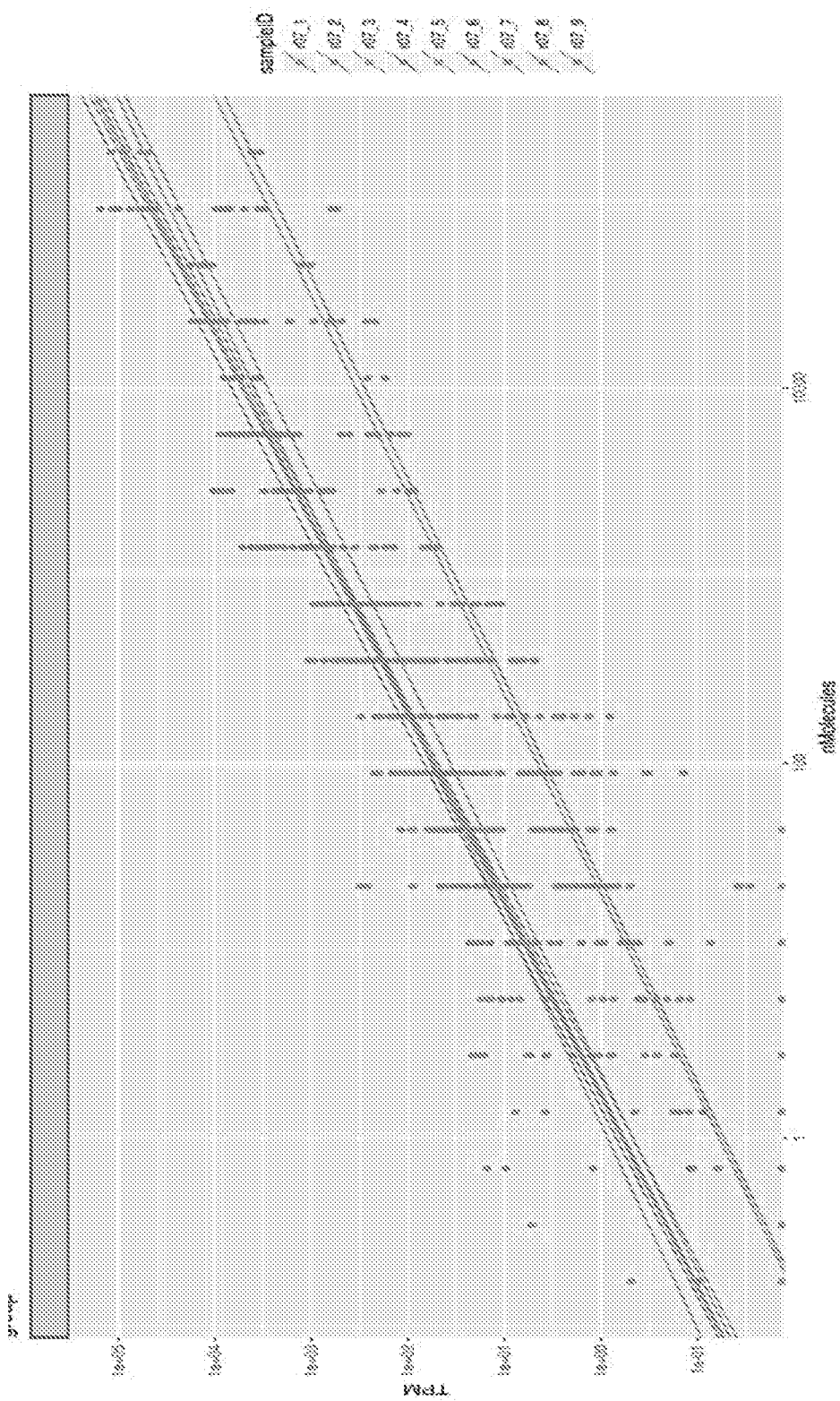
FIG. 42 demonstrates the limit of detection for ERCC transcripts.
Figure 43:
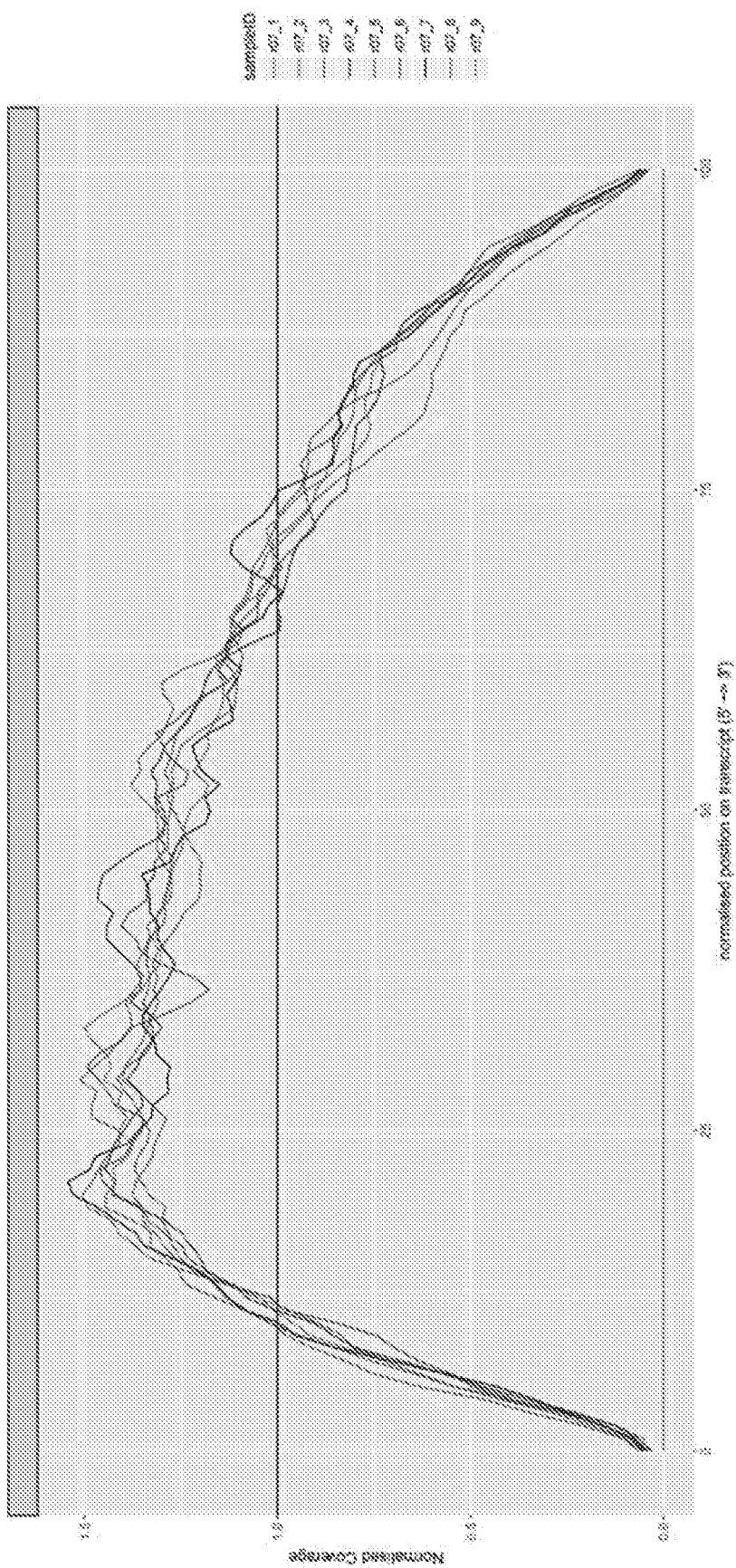
FIG. 43 plots the normalized position on the transcript (5' to 3') versus normalized coverage.

FIG. 42 demonstrates that the ERCC spike-ins detection levels observed in samples 1-7 are different from samples 8-9 samples, FIG. 43 shows the relatively uniform coverage of the transcript length observed with Long RNASeq Workflow Method 3 libraries, which is consistent between replicates and across all samples.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

REFERENCES

Abravaya, K., J. J. Carrino, S. Muldoon, and H. H. Lee. 1995 Detection of point mutations with a modified ligase chain reaction (Gap-LCR). *Nucleic Acids Res.* 23:675-82.

Al-Nedawi, K., B. Meehan, J. Micallef. V. Lhotak, L. May, A. Guha. and J. Rak. 2008. Intercellular transfer of the oncogenic receptor EGFRvIII by microvesicles derived from tumour cells. *Nat Cell Biol.* 10:619-24.

Balzar. M., M. J. Winter, C. J. de Boer, and S. V. Litvinov. 1999. The biology of the 17-1A antigen (Ep-CAM). *J Mol Med.* 77:699-712.

Cheruvanky, A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. *Am J Physiol Renal Physiol.* 292: F1657-61.

Cotton, R. G., N. R. Rodrigues, and R. D. Campbell. 1988. Reactivity of cytosine and thymine in single-base-pair mismatches with hydroxylamine and osmium tetroxide and its application to the study of mutations. *Proc Natl Acad Sci USA.* 85:4397-401.

Fischer, S. G., and L. S. Lerman 1979a. Length-independent separation of DNA restriction fragments in two-dimensional gel electrophoresis. *Cell.* 16:191-200.

Fischer, S. G., and L. S. Lerman 1979b. Two-dimensional electrophoretic separation of restriction enzyme fragments of DNA. *Methods Enzymol.* 68:183-91.

Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. *Proc Natl Acad Sci USA.* 87:1874-8.

Hahn, P. J. 1993. Molecular biology of double-minute chromosomes. *Bioessays.* 15:477-84.

Kwoh, D. Y., G. R Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. *Proc Natl Acad Sci U S A.* 86:1173-7.

Landegren, U., R. Kaiser, J. Sanders, and L. Hood. 1988. A ligase-mediated gene detection technique. *Science.* 241: 1077-80.

Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. *Nat Med.* 14:579-84.

Miele, E. A., D. R. Mills, and F. R Kramer. 1983. Autocatalytic replication of a recombinant RNA. *J Mol Biol.* 171:281-95.

Myers, R. M., Z. Larin, and T. Maniatis. 1985. Detection of single base substitutions by ribonuclease cleavage at mismatches in RNA:DNA duplexes. *Science.* 230:1242-6.

Nagrath, S., L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber, and M. Toner. 2007. Isolation of rare circulating tumour cells in cancer patients by microchip technology. *Nature.* 450:1235-9.

Nakazawa, H. D. English, P. L. randell, K. Nakazawa, N. Martel, B. K. Armstrong, and H. Yamasaki. 1994. UV and skin cancer: specific p53 gene mutation in normal skin as a biologically relevant exposure measurement. *Proc Natl Acad Sci USA*. 91:360-4.

Orita, M., H. Iwahana, H. Kanazawa, K. Havashi, and T. Sekiya. 1989. Detection of polymorphisms of human DNA by gel electrophoresis as single-strand conformation polymorphisms. *Proc Natl Acad Sci USA*. 86:2766-70.

Raposo, G., H. W. Nijman, W. Stoorvogel. R. Liejendekker, C. V. Harding, C. J. Melief, and H. J. Geuze. 1996. B lymphocytes secrete antigen-presenting vesicles. *J Exp Med*. 183:1161-72.

Skog, J. T. Wurdinger, S. van Rijn, D. H. Meijer, L. Gainche, M. Sena-Esteves, W. T. Curry, Jr., B. S. Carter, A. M. Krichevsky, and X. O. Breakefield. 2008. Glioblastoma microvesicles transport RNA and proteins that promote tumour growth and provide diagnostic biomarkers. *Nat Cell Biol*. 10:1470-6.

Steemers, F. J., W. Chang, G. Lee, D. L. Barker, R. Shen, and K. L. Gunderson. 2006. Whole-genome genotyping with the single-base extension assay. *Nat Methods*. 3:31-3.

Taylor, D. D., and C. Gercel-Taylor. 2008. MicroRNA signatures of tumor-derived exosomes as diagnostic biomarkers of ovarian cancer. *Gynecol Oncol*. 110:13-21.

Went. P. T., A. Lugli, S. Meier, M. Bundi, M. Mirlacher, G. Sauter, and S. Dirnhofer. 2004. Frequent EpCam protein expression in human carcinomas. *Hum Pathol*. 35:122-8.

What is claimed is:

1. A method for sequencing at least one long non-ribosomal microvesicular RNA transcript from a biological sample, wherein the long non-ribosomal microvesicular RNA transcripts comprises more than 200 nucleotides and comprises long non-coding RNA, mRNA, circular RNA or any combination thereof, the method comprising:
(a) contacting the biological sample with a solid capture surface comprising an affinity membrane that binds microvesicles to retain extracellular vesicles comprising long non-ribosomal microvesicular RNA transcripts from the biological sample on or in the capture surface;
(b) contacting the capture surface with a lysis reagent while the extracellular vesicles are on or in the capture surface, thereby releasing the long non-ribosomal microvesicular RNA transcripts from the capture surface and producing a homogenate;
(c) extracting the long non-ribosomal microvesicular RNA transcripts from the homogenate;
(d) reverse transcribing the extracted long non-ribosomal microvesicular RNA transcripts into cDNA;
(e) constructing a double-stranded DNA library from the reverse-transcribed cDNA;
(f) selectively removing ribosomal RNA or RNA sequences from the double-stranded DNA library;
(g) selectively enriching for nucleic acid sequences from the double-stranded DNA library; and
(h) sequencing the selectively enriched nucleic acid sequences from the double-stranded DNA library, thereby sequencing the long non-ribosomal microvesicular RNA transcripts.

2. The method of claim 1, further comprising before or after step (c), pretreating the homogenate or the extracted long microvesicular non-ribosomal RNA transcripts with DNase, wherein the DNase is DNase I or modified DNase I.

3. The method of claim 1, wherein the step of selectively removing ribosomal DNA or RNA sequences from the double-stranded DNA library comprises using enzymatic reagents, RNase H, restriction enzyme digest, hybridization-based biotinylated probe enrichment and streptavidin conjugated paramagnetic beads, or any combination thereof.

4. The method of claim 1, wherein the step of selectively enriching for nucleic acid sequences from the double-stranded DNA library comprises using PCR-based approaches, complementary oligonucleotides, hybridization-based biotinylated probe enrichment and streptavidin conjugated paramagnetic beads, or any combination thereof.

5. The method of claim 1, wherein the long non-ribosomal microvesicular RNA transcripts comprises more than 300 nucleotides, or more than 500 nucleotides.

6. The method of claim 1, wherein the biological sample has a volume of about 0.5 mL to about 20 mL, about 0.5 mL to about 10 mL, about 0.5 mL to about 5 mL, about 0.5 mL to about 4 mL, or about 0.5 mL to about 2 mL.

7. The method of claim 1, wherein the biological sample is selected from the group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

8. The method of claim 1, wherein the solid capture surface comprises a membrane or a bead.

9. The method of claim 1, wherein the solid capture surface comprises more than one membrane, at least two membranes, at least three membranes.

10. The method of claim 1, wherein the solid capture surface is magnetic.

11. The method of claim 1, wherein the solid capture surface comprises a bead which is a positively charged ion exchange (IEX) bead, a negatively charged IEX bead, a high capacity IEX bead, a strong ferromagnetic high capacity IEX bead, a strong ferromagnetic high capacity iron oxide-containing polymer IEX bead or any combination thereof.

12. The method of claim 1, wherein the solid capture surface is functionalized with quaternary ammonium, quaternary amine, sulfate, sulfonate, tertiary amine, or any combination thereof.

13. The method of claim 1, wherein the solid capture surface comprises an IEX bead having a high ratio of bead charge to exposed surface.

14. The method of claim 1, wherein step (c) further comprises adding protein precipitation buffer to the homogenate prior to extraction of the long non-ribosomal microvesicular RNA transcripts.

15. The method of claim 1, wherein step (c) further comprises performing an enzymatic digestion, performing a proteinase digestion, performing a digestion using DNase, performing a digestion using RNase or any combination thereof.

16. The method of claim 1, wherein step (c) further comprises adding a protein precipitation buffer, wherein the protein precipitation buffer comprises a transition metal ion, a buffering agent, or both a transition metal ion and a buffering agent.

17. The method of claim 1, wherein step (a) further comprises filtering the biological sample.

18. The method of claim 1, wherein step (b) further comprises washing the capture surface after contacting the biological sample with the capture surface.

19. The method of claim 1, wherein step (c) comprises the addition of isopropanol, sodium acetate, glycogen or any combination thereof.

20. The method of claim 1, wherein after step (e), the double-stranded DNA library is amplified.

* * * * *